(12) United States Patent
Leclerc et al.

(10) Patent No.: US 9,833,504 B2
(45) Date of Patent: Dec. 5, 2017

(54) VIRUS-LIKE PARTICLES AND PROCESS FOR PREPARING SAME

(75) Inventors: Denis Leclerc, Fossambault-sur-le Lac (CA); Pierre Savard, Lévis (CA)

(73) Assignee: Folia Biotech Inc., Quebec (CA)

(*) Notice: Subject to any disclaimer, the term of this patent is extended or adjusted under 35 U.S.C. 154(b) by 0 days.

(21) Appl. No.: 14/117,365

(22) PCT Filed: May 1, 2012

(86) PCT No.: PCT/CA2012/050279
§ 371 (c)(1),
(2), (4) Date: Dec. 20, 2013

(87) PCT Pub. No.: WO2012/155262
PCT Pub. Date: Nov. 22, 2012

(65) Prior Publication Data
US 2014/0255439 A1    Sep. 11, 2014

Related U.S. Application Data

(60) Provisional application No. 61/485,955, filed on May 13, 2011.

(51) Int. Cl.
*A61K 39/12* (2006.01)
*A61K 39/39* (2006.01)

(52) U.S. Cl.
CPC .............. *A61K 39/12* (2013.01); *A61K 39/39* (2013.01); *C12N 2760/10011* (2013.01); *C12N 2760/16111* (2013.01); *C12N 2770/26023* (2013.01); *C12N 2770/26034* (2013.01); *C12N 2770/26042* (2013.01)

(58) Field of Classification Search
None
See application file for complete search history.

(56) References Cited

U.S. PATENT DOCUMENTS

| | | | |
|---|---|---|---|
| 5,443,969 A | 8/1995 | Wilson et al. | |
| 7,641,896 B2 | 1/2010 | Leclerc et al. | |
| 8,101,189 B2 | 1/2012 | Leclerc et al. | |
| 8,282,940 B2 | 10/2012 | Leclerc et al. | |
| 2007/0166322 A1* | 7/2007 | Leclerc et al. | 424/199.1 |
| 2008/0170966 A1 | 7/2008 | Dickey et al. | |
| 2009/0318337 A1 | 12/2009 | Lowell et al. | |
| 2011/0105383 A1 | 5/2011 | Hook et al. | |
| 2014/0134202 A1 | 5/2014 | Leclerc et al. | |
| 2014/0154288 A1 | 6/2014 | Lamarre | |
| 2014/0255439 A1 | 9/2014 | Leclerc | |

FOREIGN PATENT DOCUMENTS

| | | |
|---|---|---|
| CA | 2 434 000 A1 | 7/2012 |
| JP | 2009-513532 | 4/2009 |
| JP | 2010-508857 | 3/2010 |
| JP | 2010-508860 | 3/2010 |
| JP | 2010-516713 | 5/2010 |
| WO | 94/10329 A1 | 5/1994 |
| WO | 2004/004761 A2 | 1/2004 |
| WO | 2008/058369 A1 | 5/2008 |
| WO | 2008/058396 A1 | 5/2008 |
| WO | 2008/089569 A1 | 7/2008 |
| WO | 2010/012069 A1 | 2/2010 |
| WO | 2012/155261 A1 | 11/2012 |

OTHER PUBLICATIONS

Tremblay et al. Effect of mutations K97A and E128A on RNA binding and self assembly of papaya mosaic potexvirus coat protein. FEBS J. Jan. 2006;273(1):14-25.*
Sit et al. The minimal 5' sequence for in vitro initiation of papaya mosaic potexvirus assembly. Virology. Feb. 15, 1994;199(1):238-42.*
Shin et al. Replication and encapsidation of recombinant Turnip yellow mosaic virus RNA. BMB reports 2008; 41(10): 739-744.*
Lee et al. Subgenomic RNAs of bamboo mosaic potexvirus-V isolate are packaged into virions. J Gen Virol. Jul. 1998;79 ( Pt 7):1825-32.*
GenBank: D13957.1. Papaya mosaic virus genomic RNA, complete genome. Feb. 3, 1999.*
Leclerc et al. Proteasome-independent major histocompatibility complex class I cross-presentation mediated by papaya mosaic virus-like particles leads to expansion of specific human T cells. J Virol. Feb. 2007;81(3):1319-26. Epub Nov. 22, 2006.*
Abouhaidar, Mounir G., "The Polarity of Assembly of Papaya Mosaic Virus and Tobacco Mosaic Virus RNAs with PMV-Protein under Conditions of Nonspecificity," Virology 107(1), 202-207 (1980).
Cox et al., "Adjuvants modulating muscosal immune responses or directing systemic responses towards the mucosa," Vet. Res. 37, 511-539 (2006).
Diebold, et al., "Innate Antiviral Responses by means of TLR7-Mediated Recognition of Single-Stranded RNA," Science 303, 1529-1531 (2004).
Erickson, John W. and Bancroft, J.B., "The Self-Assembly of Papaya Mosaic Virus," Virology 90, 36-46 (1978).
Erickson, John W. and Bancroft, J.B., "The Kinetics of Papaya Mosaic Virus Assembly," Virology 90, 47-53 (1978).
Erickson, John W. and Bancroft, J.B., "The Assembly of Papaya Mosaic Virus Protein," Virology 72(2), 514-517 (1976).
"Papaya mosaic virus, complete genome," Genbank Accession No. NC_001748.1 (nucleotides 5889-6536).
"Capside protein [Papaya mosaic virus]," Genbank Accession No. NP_044334.1.
Giri, et al. "Is Intranasal Vaccination a Feasible Solution for Tuberculosis?", Expert Rev Vaccines 7(9), 1341-1356 (2008).
Lacasse et al., "Novel Plant Virus-Based Vaccine Induces Protective Cytotoxic T-Lymphocyte-Mediated Antiviral Immunity through Dendritic Cell Maturation," J. Virology 82, 785-794 (2008).

(Continued)

*Primary Examiner* — Nianxiang Zou
(74) *Attorney, Agent, or Firm* — Knobbe Martens Olson & Bear LLP

(57) ABSTRACT

An in vitro process of preparing virus-like particles (VLPs) from recombinant papaya mosaic virus coat protein and ssRNA, which allows for large scale production of VLPs in high yields, is provided. Also provided are VLPs comprising ssRNA prepared by the in vitro process. The VLPs can be used as adjuvants and when fused to an antigen, as vaccines. The use of the VLPs for stimulation of the innate immune response is also provided.

32 Claims, 34 Drawing Sheets

(56) References Cited

OTHER PUBLICATIONS

Laliberté-Gagné et al., "The F13 residue is critical for interaction among the coat protein subunits of papaya mosaic virus," FEBS J. 275, 1474-1484 (2008).
Lebel, et al, "Novel plant virus-like particle vaccine platform induces immune system activation through Toll-like receptor 7 signaling and interferon alpha production", Nov. 16-19, 2011, Cold Spring Harbor, New York, USA, Poster Presentation.
Mathieu, et al., "Induction of innate immunity in lungs with virus-like nanoparticles leads to protection against influenza and *Streptococcus pneumoniae* challenge," Nanomedicine: Nanotechnology, Biology and Medicine 9, 839-848 (2013).
Maurer, M. and Von Stebut, E., "Molecules in focus, Macrophage inflammatory protein-1", The International Journal of Biochemistry & Cell Biology 36, 1882-1886 (2004).
Menten et al., "Macrophage inflammatory protein-1," Cytokine Growth Factor Reviews 13, 455-481 (2002).
Noa-Carrazana, J.C. and Silva-Rosales, L., First Report of a Mexican Isolate of Papaya mosaic virus in Papaya (*Carica papaya*) and Pumpkin (*Cucurbita pepo*), Plant Science 85, p. 558 (2001).
Rampersaud, Anand, "Expression, Purification and Properties of Papaya Mosaic Virus Capsid Protein in *Excherichia coli*," Master Thesis, University of Britich Columbia, pp. 36-46 (1997).
Sit, et al., "The Minimal 5' Sequence for in Vitro Initiation of Papaya Mosaic Potexvirus Assembly," Virology, 199, 238-242 (1994).
Sit, et al., "Nucleotide Sequence of Papaya Mosaic Virus RNA," J. Gen. Virol, 70, 2325-2331 (1989).
Stowell et al., "Long-term activation of TLR3 by Poly(I:C) induces inflammation and impairs lung function in mice," Respir. Res., 10, p. 43 (2009).
Thompson et al., "Pattern Recognition Receptors and the Innate Immune Response to Viral Infection," Viruses, 3, 920-940 (2011).
Van Der Poll et al., "Interleukin-6 gene deficient mice show impaired defense against pneumococcal pneumonia," J. Infect. Dis., 176(2), 439-444 (1997).
Zepp, et al., "IL-17 receptor signaling and Th17-mediated autoimmune demyelinating disease," Trends Immunol. (2011) (epub ahead of print).
Aliberti et al., "CCR5 provides a signal for microbial induced production of IL-12 by CD8α+ dendritic cells," Natural Immunology 1, 83-87 (2000).
International Search Report and Written Opinion dated Aug. 16, 2012 for PCT/CA2012/050279.
Restriction Requirement for U.S. Appl. No. 14/117,363 dated Dec. 18, 2014.
Jegerlehner, et al. "TLR9 Signaling in B Cells Determines Class Switch Recombination to IgG2a," J. Immunol. 178, 2415-2420 (2007).
Leclerc et al., "Proteasome-Independent Major Histocompatibility Complex Class I Cross-Presentation Mediated by Papaya Mosaic Virus-Like Particles Leads to Expansion of Specific Human T Cells," J. Virol. 81(30),1319 (2007).
Metcalf, Donald, "The colony-stimulating factors and cancer," Nature Reviews Cancer, 10, 425-434 (2010).
International Search Report dated Sep. 13, 2012 for PCT/CA2012/050278.
Acosta-Ramirez et al., "Translating innate response into long-lasting antibody response by the intrinsic antigen-adjuvant properties of papaya mosaic virus" Immunology, 2007, vol. 124, pp. 186-197.
Akira, Shizuo, "Innate immunity and adjuvants", Phil. Trans. R. Soc. B, 366, pp. 2748-2755 (2011).
Barber, D.L. et al. "Restoring function in exhausted CD8 T cells during chronic viral infection," Nature, 439(7077), pp. 682-687 (2006).
Denis, J., et al., "Immunogenicity of papaya mosaic virus-like particles fused to a hepatitis C virus epitope: Evidence for the critical function of multimerization", Virology 363, pp. 59-68 (2007).
Denis, J. et al., "Development of a universal influenza A vaccine based on the M2e peptide fused to the papaya mosaic virus (PapMV) vaccine platform," Vaccine 26, pp. 3395-3403 (2008).
Holmgren & Czerkinsky, "Mucosal immunity and vaccines," Nature Medicine 11(4), pp. S45-S53 (2005).
Horton, C.G. et al., "Targeting Toll-Like Receptors for Treatment of SLE," Hindawi Publishing, vol. 2010, Article ID 498980, pp. 1-9 (2010).
Mukhamedzhanova, A.A. et al. "Characterization of Alternanthera mosaic virus and its Coat Protein," The Open Virology Journal 5, pp. 125-129 (2011).
Savard, C. et al., "Improvement of the Trivalent Inactivated Flu Vaccine Using PapMV Nanoparticles," PloS ONE 6 (6), (Jun. 2011).
Bessa et al., "Efficient induction of muscosal and systemic immune responses by virus-like particles administered intranasally: implications for vaccine design," Eur. J. Immunol. 208, 38: 114-126.
Hanafi, et al., "Two distinct chimeric potexviruses share antigenic cross-presentation properties of MHC class I epitopes," Vaccine 28 (2010) 5617-5626.
Englund et al., "Viral Infections in Immunocompromised Patients," Biol Blood Marrow Transplant 17: S2-S5 (2011).
Mathieu, C., Stimulation of innate immunity by papaya mosaic virus. International Conference & Exhibition on Virology, Sep. 5-7, Baltimore, USA, Sep. 5, 2011, p. 1—Poster.
Wang, T., Proinflammatory properties of papaya mosaic virus (PapMV) are dependent on ToL1-like receptor 4 (TLR4) engagement. Thesis. McGill University, Montreal, Oct. 5, 2005.
English translation of Japanese Office Action for JP 2014-509576 dated Feb. 19, 2016.
English translation of Japanese Office Action for JP2014-509577 dated Feb. 23, 2016, on related U.S. Appl. No. 14/117,365.
English translation of Chinese Office Action for CN201280023824.X dated Jul. 3, 2015.
English translation of Chinese Office Action for CN201280022947.1 dated Mar. 22, 2016, on related U.S. Appl. No. 14/117,365.
Supplementary European Search Report for EP 12 786 315.7 dated May 7, 2015.
EP Examination Report for EP 12 785 518.7 dated Oct. 23, 2015, on related U.S. Appl. No. 14/117,365.
Mexican Office Action for MX51776 dated Jun. 23, 2015, on related U.S. Appl. No. 14/117,365.
Australian Examination Report in Australian Application No. 2012255594, dated Jul. 7, 2016.
Australian Examination Report in related Australian Application No. 2012255595, dated Apr. 22, 2016.
English Translation of Mexican Office Action dated Feb. 18, 2016, in related Mexican Application MS/a/2013/013228.
English Translation of Chinese Office Action dated Mar. 10, 2016, in related Chinese Application 201280023824.X.
English Translation of Chinese Office Action dated Nov. 22, 2016, in related Chinese Application 201280023824.X.
European Office Action in European Application No. 12 786 315.7-1410, dated May 3, 2016.
European Office Action in related European Application No. 12 785 518.7-1410, dated May 4, 2016.
European Office Action in European Application No. 12 786 315.7-1410, dated Nov. 22, 2016.

* cited by examiner

A.
MSKSSMSTPNIAFPAITQEQMSSIKVDPTSNLLPSQEQLKSVSTLMVAAKVPAASVTT
VALELVNFCYDNGSSAYTTVTGPSSIPEISLAQLASIVKASGTSLRKFCRYFAPIIWNL
RTDKMAPANWEASGYKPSAKFAAFDFFDGVENPAAMQPPSGLIRSPTQEERIANATN
KQVHLFQAAAQDNNFTSNSAFITKGQISGSTPTIQF LPPPE

B.
ATGTCTAAGTCAAGTATGTCCACACCCAACATAGCCTTCCCCGCCATCACCCAGG
AACAGATGAGCTCGATTAAGGTCGATCCAACGTCCAATCTTCTGCCCTCCCAAGA
GCAGTTAAAGTCAGTGTCCACCCTCATGGTAGCTGCTAAGGTTCCAGCAGCCAGT
GTTACAACTGTGGCATTGGAGTTGGTCAACTTCTGCTATGACAATGGGTCCAGCG
CGTACACCACAGTGACTGGCCCATCATCAATACCGGAGATATCACTGGCACAATT
GGCTAGTATTGTCAAAGCTTCCGGCACTTCCCTTAGAAAATTCTGCCGGTACTTC
GCGCCAATAATCTGGAATCTGAGGACGGACAAAATGGCTCCTGCCAATTGGGAG
GCTTCAGGATACAAGCCAAGCGCCAAATTTGCCGCGTTCGACTTCTTCGACGGGG
TGGAGAATCCGGCGGCCATGCAACCCCTTCGGGACTAATCAGGTCGCCGACCC
AGGAAGAGCGGATTGCCAATGCTACCAACAAACAGGTGCATCTCTTCCAAGCCG
CGGCACAGGACAACAACTTTACCAGCAACTCCGCCTTCATCACCAAAGGCCAAA
TTTCTGGGTCAACCCCAACCATCCAATTCCTTCCACCCCCGAATAA

FIGURE 1

A.
MASTPNIAFPAITQEQMSSIKVDPTSNLLPSQEQLKSVSTLMVAAKVPAASVTTVALE
LVNFCYDNGSSAYTTVTGPSSIPEISLAQLASIVKASGTSLRKFCRYFAPIIWNLRTDK
MAPANWEASGYKPSAKFAAFDFFDGVENPAAMQPPSGLTRSPTQEERIANATNKQV
HLFQAAAQDNNFASNSAFITKGQISGSTPTIQFLPPPE

B.
MASTPNIAFPAITQEQMSSIKVDPTSNLLPSQEQLKSVSTLMVAAKVPAASVTTVALE
LVNFCYDNGSSAYTTVTGPSSIPEISLAQLASIVKASGTSLRKFCRYFAPIIWNLRTDK
MAPANWEASGYKPSAKFAAFDFFDGVENPAAMQPPSGLTRSPTQEERIANATNKQV
HLFQAAAQDNNFASNSAFITKGQISGSTPTIQFLPPPETSTTRHHHHHH

T7-TRANSCRIPTION START-
GGGCGAATTGGAGCTCGAAAAGAAACACAAAGCAAAGCAAAGCAAAGCAACTCAAATAAACCATATTTGGCCAAGGCACTTGG
TAATCAAACGGGCACAACCCTAGATTAACGATTAAGCAAATTTGAGGAGTGTTTTCGAACAGTTGAACGACGTCTCACTCCGG
GCTGTTATTCAAGAAGAGGCCTACAGAGACATTAAGCTCACTATTAAGGAAACTAAAACCTACAATCCTTTAACACATCCAGT
AGCAGTAGCAGATAGTTTAGAAAAATTAGGAATAGAAACTAACCCCTTTGCCGTCAAGGCGCATACGCTAACCGCGGCAAAAA
CAATAGAATTAGATTAATACAAAATAGTTTCTTTCTACCTCCCAAAGGAGAACCCCACTACCTTTTAATTCTAAAAGAGGAGC
AAGTTGCAATATTTTAGAAGAGGCCCACAGCAAAAGTAATATTCCTCATAACTCACATAGAACCCAAAGACGTGGCTAGGT**T
AAACGTGGACACCCTTTTTGACAAGAACGTGACCCCACAGATTACCACAAACACAGCCTTTTAA**GGGGATACCCTCCATTTTC
TCCCACTAACAGCGATTGAAAGGATTTTTAAATCCTCCCCCAACTTCAAACCCTCTACGCCACTTAAGTACTCCCACCGGAGG
CCCTGCATAGGCTGCATTCCCTGCACCCTGGTATATTAAAATTAGAGTTTCACCAAGAACATTTCATCTACAAACCAGGGGGT
CTAACTGGGGCAGCGTACATCCACAAATACGAGCAACTCGAGTGGATTAAAGTGGGAAGGTTTAAGTGGGCGGACGGGAAGGG
GCTTACCCACACGGTGACCTCACAAATTTTGGAAACTAAAGGTGCCAACCACCTCTTCATTTTTCAGAGAGGGAGGTTTCTGA
CTCCAGAATTGAGGTGTTTCAACACTGAGACAAAATTAATCACCTAACCTCCCATCTTCCTCCCCAAGCAGTTTATAACCCGG
TTGCCAATTAAGAAAACCAACCGGTCCGCCCAACAATTGTTTCTCTACGTAAAATCAGTGAAGATAATAACAGAGAGGGACAT
CTGGGCAAAGTAAAGACAGTTGCTCAAGACTTCGGAGCTACAAGATTACAATCCAAGGGAGGTGGCTCTGCTGGTGAACTATT
TTCTCTTGATCGCCAGATTAAGGTCGGAAACGTGTTTTGACAACGTCCTCAGCGGGGGATAATTCAAGAAACTCTTCAAACCC
TTCATCGCTAAGTGGGAGATCCAAAAACACAAAATTTTTGGAATAAAGGAGTTTGAACAGTTATAAGAAGCTCTGGATAAGGT
GGTAATAACACTGACCTACCCAACAAAAACTTTTGACAATCGGGGTTGGGTGGTTAAGCTGGAAGCGAGGAGGGGTTACGAGT
GGTTCGCTGTAAGTAACACAAGCCGAAGGGTCCAGAACTAAACTTGGAGGAGAAGAAAACGGATCCGGACGCCGCATCCTAC
GAAAAATACTTGAAAGCCCTGAACGCGT-3'

B.

5'-
GGGCGAATTGGAGCTCGAAAAGAAACACAAAGCAAAGCAAAGCAAAGCAACTCAAATAAACCATATTTGGCCAAGGCACTTGG
TAATCAAACGGGCACAACCCTAGATTAACGATTAAGCAAATTTGAGGAGTGTTTTCGAACAGTTGAACGACGTCTCACTCCGG
GCTGTTATTCAAGAAGAGGCCTACAGAGACATTAAGCTCACTATTAAGGAAACTAAAACCTACAATCCTTTAACACATCCAGT
AGCAGTAGCAGATAGTTTAGAAAAATTAGGAATAGAAACTAACCCCTTTGCCGTCAAGGCGCATACGCTAACCGCGGCAAAAA
CAATAGAATTAGATTAATACAAAATAGTTTCTTTCTACCTCCCAAAGGAGAACCCCACTACCTTTTAATTCTAAAAGAGGAGC
AAGTTGCAATATTTTAGAAGAGGCCCACAGCAAAAGTAATATTCCTCATAACTCACATAGAACCCAAAGACGTGGCTAGGT**T
AAACGTGGACACCCTTTTTGACAAGAACGTGACCCCACAGATTACCACAAACACAGCCTTTTAA**GGGGATACCCTCCATTTTC
TCCCACTAACAGCGATTGAAAGGATTTTTAAATCCTCCCCCAACTTCAAACCCTCTACGCCACTTAAGTACTCCCACCGGAGG
CCCTGCATAGGCTGCATTCCCTGCACCCTGGTATATTAAAATTAGAGTTTCACCAAGAACATTTCATCTACAAACCAGGGGGT
CTAACTGGGGCAGCGTACATCCACAAATACGAGCAACTCGAGTGGATTAAAGTGGGAAGGTTTAAGTGGGCGGACGGGAAGGG
GCTTACCCACACGGTGACCTCACAAATTTTGGAAACTAAAGGTGCCAACCACCTCTTCATTTTTCAGAGAGGGAGGTTTCTGA
CTCCAGAATTGAGGTGTTTCAACACTGAGACAAAATTAATCACCTAACCTCCCATCTTCCTCCCCAAGCAGTTTATAACCCGG
TTGCCAATTAAGAAAACCAACCGGTCCGCCCAACAATTGTTTCTCTACGTAAAATCAGTGAAGATAATAACAGAGAGGGACAT
CTGGGCAAAGTAAAGACAGTTGCTCAAGACTTCGGAGCTACAAGATTACAATCCAAGGGAGGTGGCTCTGCTGGTGAACTATT
TTCTCTTGATCGCCAGATTAAGGTCGGAAACGTGTTTTGACAACGTCCTCAGCGGGGGATAATTCAAGAAACTCTTCAAACCC
TTCATCGCTAAGTGGGAGATCCAAAAACACAAAATTTTTGGAATAAAGGAGTTTGAACAGTTATAAGAAGCTCTGGATAAGGT
GGTAATAACACTGACCTACCCAACAAAAACTTTTGACAATCGGGGTTGGGTGGTTAAGCTGGAAGCGAGGAGGGGTTACGAGT
GGTTCGCTGTAAGTAACACAAGCCGAAGGGTCCAGAACTAAACTTGGAGGAGAAGAAAACGGATCCGGACGCCGCATCCTAC
GAAAAATACTTGAAAGCCCTGAACGCGTGCCTTTTGCAGAAAGAACCGGAGGTCTAAGAAGCCAAAGAAGCAGAGGCAACAG**T
AA**ACCCCAAAGGCCCGAAATTAAGGAAGAGCAGGCGGAGGCTTCCACGAGTGGGAGGGCTGAAGAAATTCAAGAGGATCCGG
CAACCAGGAAAGGGAAGGAGGAGCCGAACCCCAATCGGGACCTGCTCTGCCCTAACGGATTACATCTAAAGATCAAAATAACC
GAATTTCCTGAACTTCCGGTACTCGATCATCCAGATCATCTCACCGGAAGAAAAGCTAAGTTCTTTTCAAAGGTAAGAAAGCC
ATACTCCTACACAGGAGGCTCACTAACATCTCGAGGCTGGCCAAATTGGCTGGAGAAAATTTTAGCTGCAATAGAAATCAAAG
AGCCACTGCCGGAATTCAACCATAACTTAGTCCAGCAGTTTAAACTCCAAGCGGCCATCCCATTCCACCGAGTAATAAAACCG
TGTTATCCAAAGGGTCACCAGGTTGGCGCCCTCACCATCAACCACTCGGGAGATAACCTCACCCAAATAGCTTGCCAAAAAGG
AAAGGCAAGTATAACCTAAGGATTCGGGGACTACTACTTGAGCCCAGTGGGATTCCAAGAGTCCCACAAGCTAACGGTGAGCA
ACACCACAGGGGGAAGGGTGTCTCTGACCTTCAGTAACACAGTCCAGCAAAACAAATTTATAATAATAAGAAGTTAAGAAGCC
CTTAATAACCTTCCTTGGAAACGTGGATCCCGAAACTGCAAAATTTAGGATTCCAAGGACGGCAGCTTCAGTTAAATCCTAT
AAGAGCACTGATTAGCCCCACTGAGGAAATTCGAAGCTAACCCAAGTGTAAGCCTGAAGGGTCTCCAGAAGTAGTTTACAAGA
CGCTGGACGGACTAGCTCGTGCGCCAACTCCATATTCGCCAAACCCTATCCGAGCTAGAGCATACACCTCAGTAATCAAAAAC
TGCAGAATTGGGGCCCTGCTAAGGCAACAAGGTAAGGAGTGGGGTAACAGGTTTGTAACATTGGTAGAAGCTGGCAAGAGAGA
GTTGGCCATCCCCGTAATTCACGGAGCGGGAGGAAGTGGGAAGTCACAAGCATTGCAGACCCTGATTAAGGACAACCCAGAGC
TTGATA-3'

FIGURE 7

A.
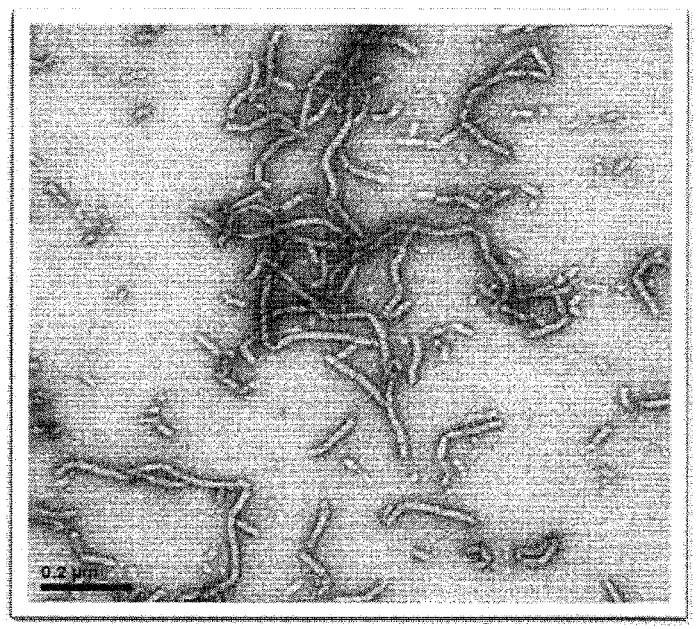
B.
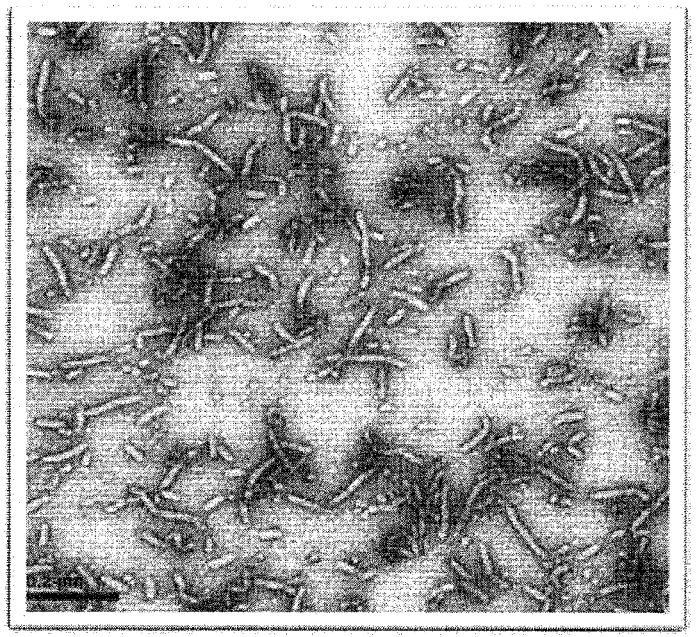
FIGURE 8

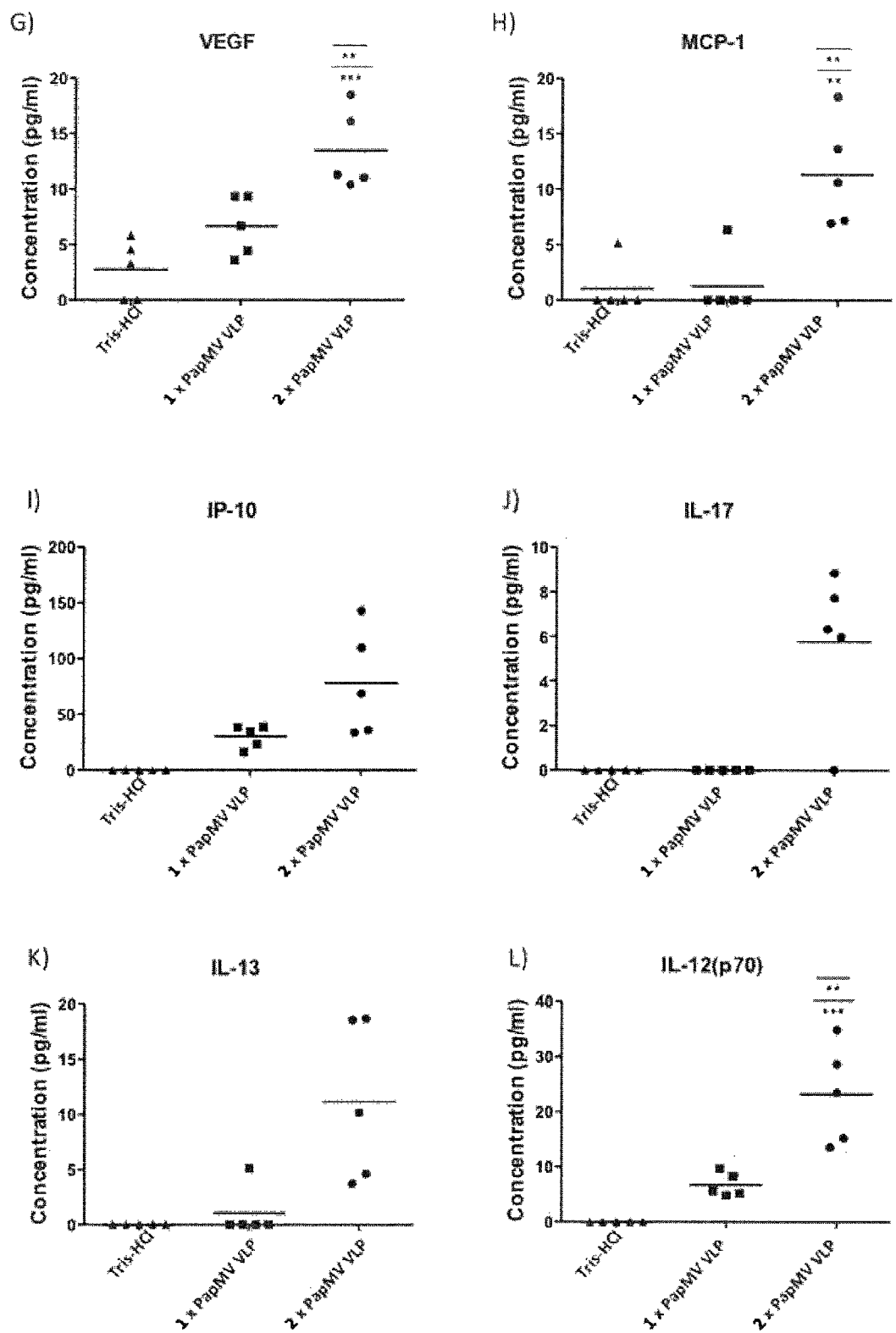
FIGURE 11 (con.)

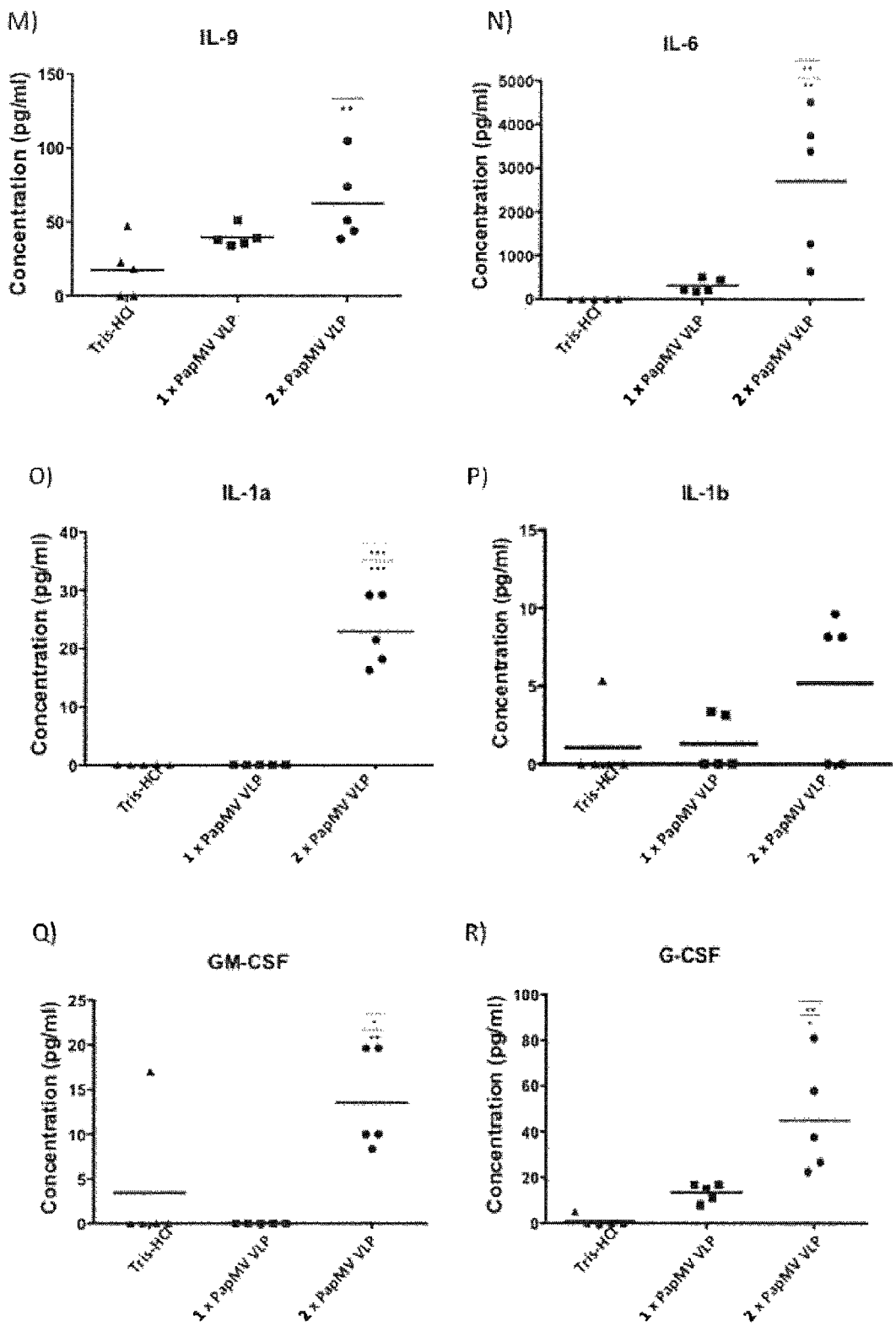
FIGURE 11 (con.)

A.
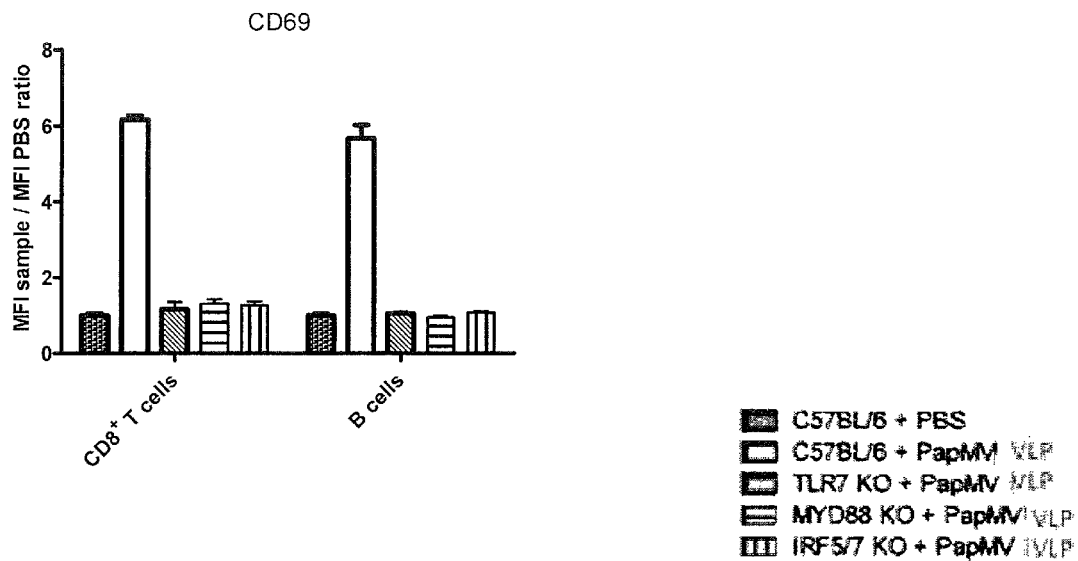
B.
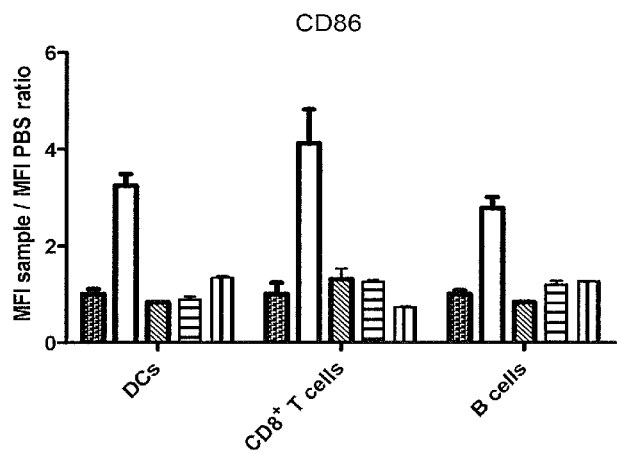
FIGURE 12

A.
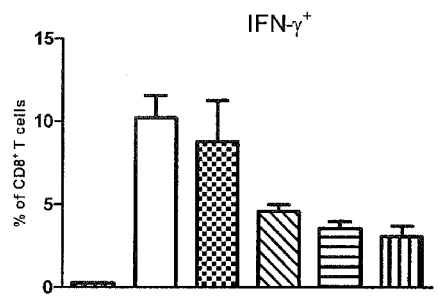
B.
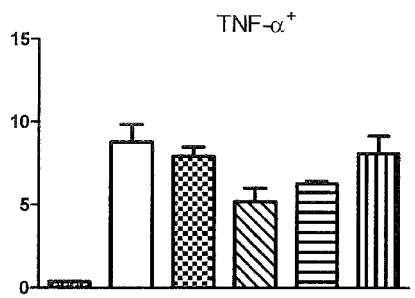
C.
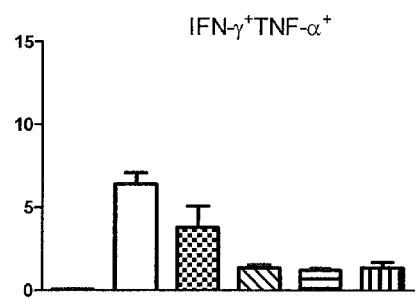
D.
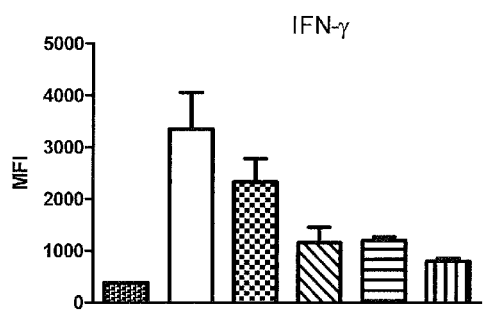
E.
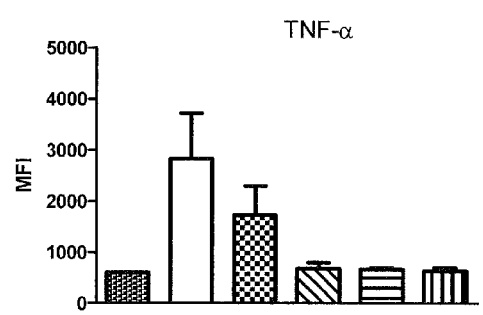
F.
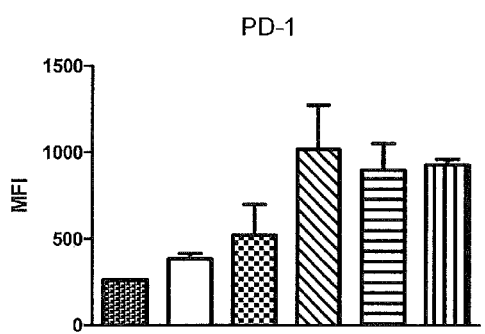
G.
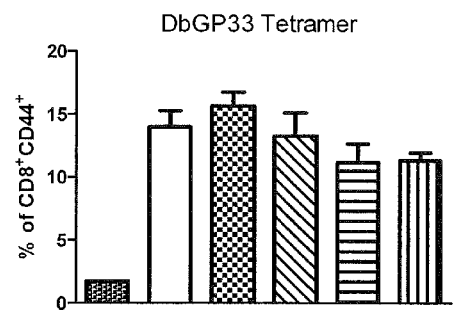
FIGURE 18

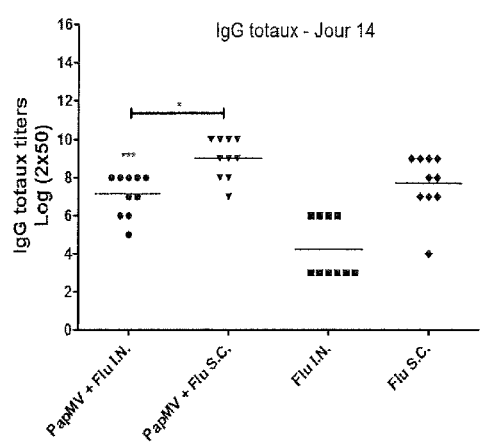
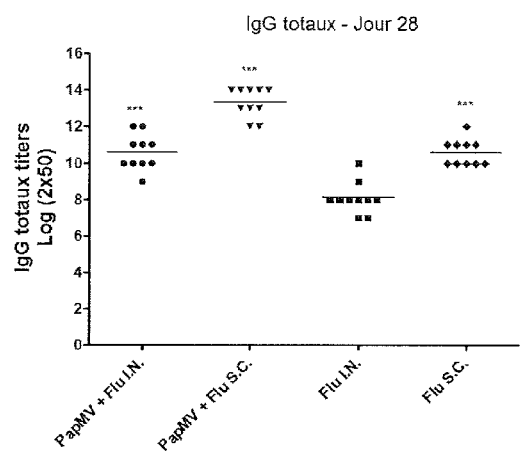
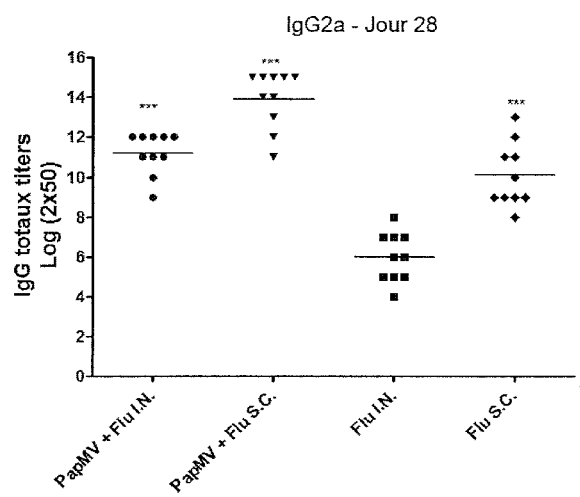
FIGURE 26

A.
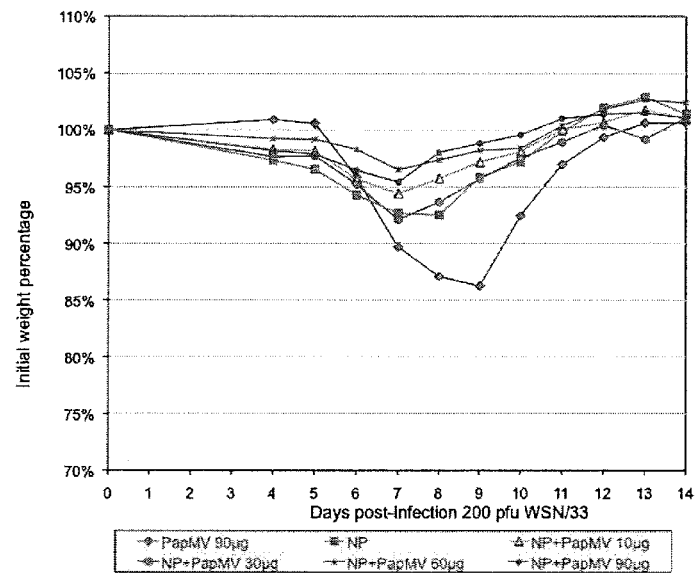
B.
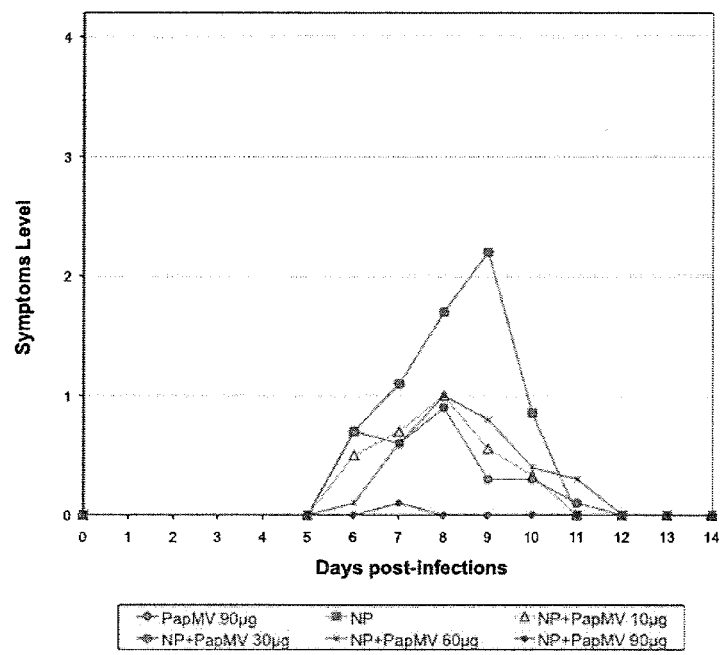
FIGURE 31

A.
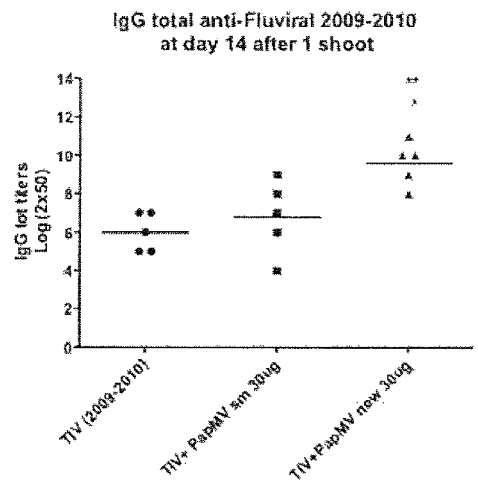
B.
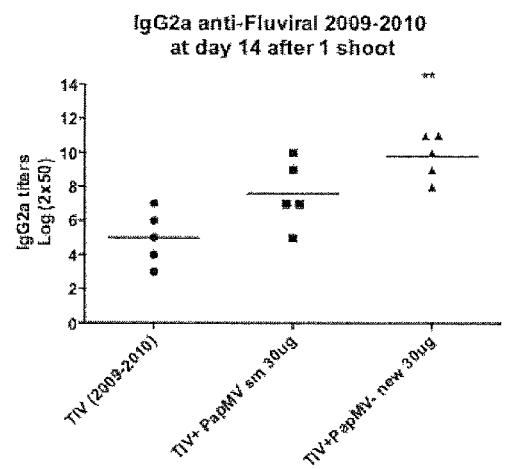
FIGURE 32

SEQUENCE LISTING

<160> NUMBER OF SEQ ID NOS: 6

<210> SEQ ID NO 1
<211> LENGTH: 215
<212> TYPE: PRT
<213> ORGANISM: Papaya mosaic Virus (PapMV)

<400> SEQUENCE: 1

Met Ser Lys Ser Ser Met Ser Thr Pro Asn Ile Ala Phe Pro Ala Ile
1               5                   10                  15

Thr Gln Glu Gln Met Ser Ser Ile Lys Val Asp Pro Thr Ser Asn Leu
            20                  25                  30

Leu Pro Ser Gln Glu Gln Leu Lys Ser Val Ser Thr Leu Met Val Ala
        35                  40                  45

Ala Lys Val Pro Ala Ala Ser Val Thr Thr Val Ala Leu Glu Leu Val
    50                  55                  60

Asn Phe Cys Tyr Asp Asn Gly Ser Ser Ala Tyr Thr Val Thr Gly
65                  70                  75                  80

Pro Ser Ser Ile Pro Glu Ile Ser Leu Ala Gln Leu Ala Ser Ile Val
                85                  90                  95

Lys Ala Ser Gly Thr Ser Leu Arg Lys Phe Cys Arg Tyr Phe Ala Pro
            100                 105                 110

Ile Ile Trp Asn Leu Arg Thr Asp Lys Met Ala Pro Ala Asn Trp Glu
        115                 120                 125

Ala Ser Gly Tyr Lys Pro Ser Ala Lys Phe Ala Ala Phe Asp Phe Phe
    130                 135                 140

Asp Gly Val Glu Asn Pro Ala Ala Met Gln Pro Pro Ser Gly Leu Ile
145                 150                 155                 160

Arg Ser Pro Thr Gln Glu Glu Arg Ile Ala Asn Ala Thr Asn Lys Gln
                165                 170                 175

Val His Leu Phe Gln Ala Ala Ala Gln Asp Asn Asn Phe Thr Ser Asn
            180                 185                 190

Ser Ala Phe Ile Thr Lys Gly Gln Ile Ser Gly Ser Thr Pro Thr Ile
        195                 200                 205

Gln Phe Leu Pro Pro Pro Glu
    210                 215

<210> SEQ ID NO 2
<211> LENGTH: 648
<212> TYPE: DNA
<213> ORGANISM: Artificial sequence
<220> FEATURE:
<223> OTHER INFORMATION: PapMV coat protein coding sequence

<400> SEQUENCE: 2
atgtctaagt caagtatgtc cacacccaac atagccttcc ccgccatcac ccaggaacag      60
atgagctcga ttaaggtcga tccaacgtcc aatcttctgc cctcccaaga gcagttaaag     120
tcagtgtcca ccctcatggt agctgctaag gttccagcag ccagtgttac aactgtggca     180
ttggagttgg tcaacttctg ctatgacaat gggtccagcg cgtacaccac agtgactggc     240
ccatcatcaa taccggagat atcactggca caattggcta gtattgtcaa agcttccggc     300
acttccctta gaaaattctg ccggtacttc gcgccaataa tctggaatct gaggacggac     360
aaaatggctc ctgccaattg ggaggcttca ggatacaagc caagcgccaa atttgccgcg     420
ttcgacttct tcgacggggt ggagaatccg gcggccatgc aaccccttc gggactaatc     480 aggtcgccga cccaggaaga gcggattgcc aatgctacca caaacaggt gcatctcttc     540

```
caagccgcgg cacaggacaa caactttacc agcaactccg ccttcatcac caaaggccaa      600
atttctgggt caaccccaac catccaattc cttccacccc ccgaataa                   648
```

<210> SEQ ID NO 3
<211> LENGTH: 211
<212> TYPE: PRT
<213> ORGANISM: Artificial sequence
<220> FEATURE:
<223> OTHER INFORMATION: PapMV coat protein CP N5

<400> SEQUENCE: 3

```
Met Ala Ser Thr Pro Asn Ile Ala Phe Pro Ala Ile Thr Gln Glu Gln
1               5                   10                  15

Met Ser Ser Ile Lys Val Asp Pro Thr Ser Asn Leu Leu Pro Ser Gln
            20                  25                  30

Glu Gln Leu Lys Ser Val Ser Thr Leu Met Val Ala Ala Lys Val Pro
        35                  40                  45

Ala Ala Ser Val Thr Thr Val Ala Leu Glu Leu Val Asn Phe Cys Tyr
    50                  55                  60

Asp Asn Gly Ser Ser Ala Tyr Thr Thr Val Thr Gly Pro Ser Ser Ile
65                  70                  75                  80

Pro Glu Ile Ser Leu Ala Gln Leu Ala Ser Ile Val Lys Ala Ser Gly
                85                  90                  95

Thr Ser Leu Arg Lys Phe Cys Arg Tyr Phe Ala Pro Ile Ile Trp Asn
            100                 105                 110

Leu Arg Thr Asp Lys Met Ala Pro Ala Asn Trp Glu Ala Ser Gly Tyr
        115                 120                 125

Lys Pro Ser Ala Lys Phe Ala Ala Phe Asp Phe Phe Asp Gly Val Glu
    130                 135                 140

Asn Pro Ala Ala Met Gln Pro Pro Ser Gly Leu Thr Arg Ser Pro Thr
145                 150                 155                 160

Gln Glu Glu Arg Ile Ala Asn Ala Thr Asn Lys Gln Val His Leu Phe
                165                 170                 175

Gln Ala Ala Ala Gln Asp Asn Asn Phe Ala Ser Asn Ser Ala Phe Ile
            180                 185                 190

Thr Lys Gly Gln Ile Ser Gly Ser Thr Pro Thr Ile Gln Phe Leu Pro
        195                 200                 205

Pro Pro Glu
    210
```

<210> SEQ ID NO 4
<211> LENGTH: 222
<212> TYPE: PRT
<213> ORGANISM: Artificial sequence
<220> FEATURE:
<223> OTHER INFORMATION: PapMV coat protein CPsm

<400> SEQUENCE: 4

```
Met Ala Ser Thr Pro Asn Ile Ala Phe Pro Ala Ile Thr Gln Glu Gln
1               5                   10                  15

Met Ser Ser Ile Lys Val Asp Pro Thr Ser Asn Leu Leu Pro Ser Gln
            20                  25                  30

Glu Gln Leu Lys Ser Val Ser Thr Leu Met Val Ala Ala Lys Val Pro
        35                  40                  45

Ala Ala Ser Val Thr Thr Val Ala Leu Glu Leu Val Asn Phe Cys Tyr
    50                  55                  60
```

```
Asp Asn Gly Ser Ser Ala Tyr Thr Thr Val Thr Gly Pro Ser Ser Ile
 65                  70                  75                  80

Pro Glu Ile Ser Leu Ala Gln Leu Ala Ser Ile Val Lys Ala Ser Gly
             85                  90                  95

Thr Ser Leu Arg Lys Phe Cys Arg Tyr Phe Ala Pro Ile Ile Trp Asn
            100                 105                 110

Leu Arg Thr Asp Lys Met Ala Pro Ala Asn Trp Glu Ala Ser Gly Tyr
        115                 120                 125

Lys Pro Ser Ala Lys Phe Ala Ala Phe Asp Phe Asp Gly Val Glu
    130                 135                 140

Asn Pro Ala Ala Met Gln Pro Pro Ser Gly Leu Thr Arg Ser Pro Thr
145                 150                 155                 160

Gln Glu Glu Arg Ile Ala Asn Ala Thr Asn Lys Gln Val His Leu Phe
                165                 170                 175

Gln Ala Ala Ala Gln Asp Asn Asn Phe Ala Ser Asn Ser Ala Phe Ile
            180                 185                 190

Thr Lys Gly Gln Ile Ser Gly Ser Thr Pro Thr Ile Gln Phe Leu Pro
        195                 200                 205

Pro Pro Glu Thr Ser Thr Thr Arg His His His His His
    210                 215                 220
```

<210> SEQ ID NO 5
<211> LENGTH: 1522
<212> TYPE: DNA
<213> ORGANISM: Artificial sequence
<220> FEATURE:
<223> OTHER INFORMATION: ssRNA template

<400> SEQUENCE: 5

```
gggcgaattg gagctcgaaa agaaacacaa agcaaagcaa agcaaagcaa ctcaaataaa      60
ccatatttgg ccaaggcact tggtaatcaa acgggcacaa ccctagatta acgattaagc     120
aaatttgagg agtgtttttcg aacagttgaa cgacgtctca ctccgggctg ttattcaaga    180
agaggcctac agagacatta agctcactat taaggaaact aaaacctaca atcctttaac     240
acatccagta gcagtagcag atagtttaga aaaattagga atagaaacta acccctttgc     300
cgtcaaggcg catacgctaa ccgcggcaaa acaatagaa ttagattaat acaaaatagt      360
ttctttctac ctcccaaagg agaaccccac tacctttttaa ttctaaaaga ggagcaagtt    420
gcaatatttt agaagaggcc cacagcaaaa agtaatattc ctcataactc acatagaacc     480
caaagacgtg gctaggttaa acgtggacac cctttttgac aagaacgtga ccccacagat     540
taccacaaac acagcctttt aagggggatac cctccatttt ctcccactaa cagcgattga    600
aaggattttt aaatcctccc ccaacttcaa accctctacg ccacttaagt actcccaccg    660
gaggccctgc ataggctgca ttccctgcac cctggtatat taaaattaga gtttcaccaa    720
gaacatttca tctacaaacc aggggggtcta actgggggcag cgtacatcca caaatacgag    780
caactcgagt ggattaaagt gggaagggttt aagtgggcgg acgggaaggg gcttacccac    840
acggtgacct cacaaatttt ggaaactaaa ggtgccaacc acctcttcat ttttcagaga    900
gggaggttttc tgactccaga attgaggtgt tcaacactg agacaaaatt aatcacctaa    960
cctcccatct tcctcccaa gcagtttata acccggttgc caattaagaa accaaccgg    1020
tccgcccaac aattgttctc ctacgtaaaa tcagtgaaga taataacaga gagggacatc    1080
tgggcaaagt aaagacagtt gctcaagact tcggagctac aagattacaa tccaagggag    1140
gtggctctgc tggtgaacta tttctcttg atcgccagat taaggtcgga aacgtgtttt    1200
```

```
gacaacgtcc tcagcggggg ataattcaag aaactcttca aacccttcat cgctaagtgg    1260
gagatccaaa aacacaaaat ttttggaata aaggagtttg aacagttata agaagctctg    1320
gataaggtgg taataacact gacctaccca acaaaaactt ttgacaatcg ggttgggtg     1380 gttaagctgg aagcgaggag gggttacgag tggttcgctg taaagtaaca caagccgaag    1440
ggtccagaac taaacttgga ggagaagaaa acggatccgg acgccgcatc ctacgaaaaa    1500
tacttgaaag ccctgaacgc gt                                             1522
```

<210> SEQ ID NO 6
<211> LENGTH: 2662
<212> TYPE: DNA
<213> ORGANISM: Artificial sequence
<220> FEATURE:
<223> OTHER INFORMATION: ssRNA template

<400> SEQUENCE: 6

```
gggcgaattg gagctcgaaa agaaacacaa agcaaagcaa agcaaagcaa ctcaaataaa      60
ccatatttgg ccaaggcact tggtaatcaa acgggcacaa ccctagatta acgattaagc     120
aaatttgagg agtgttttcg aacagttgaa cgacgtctca ctccgggctg ttattcaaga     180
agaggcctac agagacatta agctcactat taaggaaact aaaacctaca atcctttaac     240
acatccagta gcagtagcag atagtttaga aaaattagga atagaaacta acccctttgc     300
cgtcaaggcg catacgctaa ccgcggcaaa acaatagaa ttagattaat acaaaatagt      360
ttctttctac ctcccaaagg agaacccac tacctttaa ttctaaaaga ggagcaagtt       420
gcaatatttt agaagaggcc cacagcaaaa agtaatattc ctcataactc acatagaacc     480
caaagacgtg gctaggttaa acgtggacac ccttttttgac aagaacgtga ccccacagat    540
taccacaaac acagcctttt aaggggatac cctccatttt ctcccactaa cagcgattga     600
aaggattttt aaatcctccc ccaacttcaa accctctacg ccacttaagt actcccaccg     660
gaggccctgc ataggctgca ttccctgcac cctggtatat taaaattaga gtttcaccaa     720
gaacatttca tctacaaacc aggggtcta actgggcag cgtacatcca caaatacgag       780
caactcgagt ggattaaagt gggaaggttt aagtgggcgg acgggaaggg gcttaccac      840 acggtgacct cacaaatttt ggaaactaaa ggtgccaacc acctcttcat ttttcagaga     900
gggaggtttc tgactccaga attgaggtgt ttcaacactg agacaaaatt aatcacctaa     960
cctcccatct tcctccccaa gcagtttata acccggttgc caattaagaa aaccaaccgg    1020
tccgcccaac aattgtttct ctacgtaaaa tcagtgaaga taataacaga gagggacatc    1080
tgggcaaagt aaagacagtt gctcaagact tcggagctac aagattacaa tccaagggag    1140
gtggctctgc tggtgaacta ttttctcttg atcgccagat taaggtcgga aacgtgtttt    1200
gacaacgtcc tcagcggggg ataattcaag aaactcttca aacccttcat cgctaagtgg    1260
gagatccaaa aacacaaaat ttttggaata aaggagtttg aacagttata agaagctctg    1320
gataaggtgg taataacact gacctaccca acaaaaactt ttgacaatcg ggttgggtg     1380 gttaagctgg aagcgaggag gggttacgag tggttcgctg taaagtaaca caagccgaag    1440
ggtccagaac taaacttgga ggagaagaaa acggatccgg acgccgcatc ctacgaaaaa    1500
tacttgaaag ccctgaacgc gtgccttttg cagaaagaac cggaggtcta agaagccaaa    1560
gaagcagagc aacagtaaaa accccaaagg cccgaaatta aggaagagca ggcggaggct    1620
tccacgagtg ggagggctga agaaattcaa gaggatccgg caaccaggaa agggaaggag    1680
```

-continued

```
gagccgaacc ccaatcggga cctgctctgc cctaacggat tacatctaaa gatcaaaata    1740
accgaatttc ctgaacttcc ggtactcgat catccagatc atctcaccgg aagaaaagct    1800
aagttctttt caaaggtaag aaagccatac tcctacacag gaggctcact aacatctcga    1860
ggctggccaa attggctgga gaaaatttta gctgcaatag aaatcaaaga gccactgccg    1920
gaattcaacc ataacttagt ccagcagttt aaactccaag cggccatccc attccaccga    1980
gtaataaaac cgtgttatcc aaagggtcac caggttggcg ccctcaccat caaccactcg    2040
ggagataacc tcacccaaat agcttgccaa aaaggaaagg caagtataac ctaaggattc    2100
ggggactact acttgagccc agtgggattc caagagtccc acaagctaac ggtgagcaac    2160
accacagggg gaagggtgtc tctgaccttc agtaacacag tccagcaaaa caaatttata    2220
ataataagaa gttaagaagc ccttaataac cttccttgga aagcgtggat cccgaaactg    2280
caaaatttag gattccaagg acggcagctt cagttaaatc ctataagagc actgattagc    2340
cccactgagg aaattcgaag ctaacccaag tgtaagcctg aagggttcc agaagtagtt    2400 tacaagacgc tggacggact agctcgtgcg ccaactccat attcgccaaa ccctatccga    2460
gctagagcat acacctcagt aatcaaaaac tgcagaattg gggccctgct aaggcaacaa    2520
ggtaaggagt ggggtaacag gtttgtaaca ttggtagaag ctggcaagag agagttggcc    2580
atccccgtaa ttcacggagc gggaggaagt gggaagtcac aagcattgca gaccctgatt    2640
aaggacaacc cagagcttga ta                                              2662
```

VIRUS-LIKE PARTICLES AND PROCESS FOR PREPARING SAME

CROSS REFERENCE TO RELATED APPLICATIONS

This application is the U.S. National Phase of International Application No. PCT/CA2012/050279, filed May 1, 2012, designating the U.S. and published as WO 2012/155262 on Nov. 22, 2012 which claims the benefit of U.S. Provisional Application No. 61/485,955 filed May 13, 2011.

REFERENCE TO SEQUENCE LISTING

The present application incorporates by reference the sequence listing submitted as an ASCII text filed via EFS-Web on Nov. 12, 2013. The Sequence Listing is provided as a file entitled 16650900.txt, created on Nov. 12, 2013, which is 12.6 Kb in size.

FIELD OF THE INVENTION

The present invention relates to the field of adjuvants and immunomodulators and, in particular, to virus-like particles (VLPs) and methods of preparing VLPs.

BACKGROUND OF THE INVENTION

The ability of papaya mosaic virus (PapMV) virus-like particles (VLPs) to enhance the immunogenicity of antigens has been described in the following patent and patent applications.

U.S. Pat. No. 7,641,896, Canadian Patent Application No. 2,434,000, and International Patent Application No. PCT/CA03/00985 (WO 2004/004761) describe the use of PapMV or VLPs derived from PapMV coat protein for potentiating an immune response to an antigen in an animal. The antigen(s) may be attached to the PapMV or VLP or they may be administered in combination with the PapMV or VLP.

International Patent Application No. PCT/CA2007/002069 (WO 2008/058396) describes influenza vaccines based on PapMV and PapMV VLPs. The vaccines comprise PapMV or a PapMV VLP and one or more influenza antigens, which may be attached to the PapMV or VLP or may be administered in combination with the PapMV or VLP.

International Patent Application No. PCT/CA2007/001904 (WO 2008/058369) describes immunogenic affinity-conjugated antigen systems based on PapMV. This application describes fusions of PapMV coat protein with a plurality of affinity peptides capable of binding an antigen of interest.

International Patent Application No. PCT/CA2008/000154 (WO 2008/089569) describes vaccines against *S. typhi* and other enterobacterial pathogens based on PapMV. The vaccines comprise PapMV or a PapMV VLP and one or more enterobacterial antigens, which may be attached to the PapMV or VLP or may be administered in combination with the PapMV or VLP.

International Patent Application No. PCT/CA2009/00636 (WO 2010/012069) describes multivalent vaccines that comprise a PapMV component and one or more antigens, and their use to provide protection against a plurality of strains of a pathogen, or against more than one pathogen. The vaccines can optionally comprise a *Salmonella* spp. porin component.

The preparation of PapMV VLPs from isolated PapMV coat protein has been described. Erickson and Bancroft (1978, *Virology*, 90:36-46 & 1978, *Virology*, 90:47-53) first described the preparation of PapMV VLPs by in vitro self-assembly of isolated PapMV coat protein and PapMV RNA. The PapMV coat protein preparation used in these experiments was isolated from PapMV and was dominated by polymeric forms of the protein (sedimenting at 3 S, 14 S and 25 S), one or more of which were believed to be essential for initiation of VLP formation. Subsequent studies by Sit, et al. (1994, *Virology*, 199:238-242) established that the first 38-47 nucleotides of the PapMV genome were required for initiation of assembly and proposed that the initiation complex also required the 14 S polymer species.

It was later demonstrated that PapMV VLPs could be prepared from a monomeric form of the PapMV coat protein expressed in *E. coli*. The recombinant coat protein self-assembled within the bacterial cells and VLPs could be isolated by rupture of the cells, followed by several purification steps, including detergent treatment (see Tremblay et al. 2006, *FEBS J.*, 273:14-25; International Patent Application Nos. PCT/CA2007/002069 (WO 2008/058396), PCT/CA2007/001904 (WO 2008/058369), PCT/CA2008/000154 (WO 2008/089569) and PCT/CA2009/00636 (WO 2010/012069)).

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide papaya mosaic virus-like particles and process for preparing same. In accordance with one aspect of the present invention, there is provided an in vitro process for preparing virus-like particles (VLPs) comprising the steps of: a) combining recombinant potexvirus coat protein and ssRNA at a protein: RNA ratio of between about 1:1 and 50:1 by weight, at a pH between about 6.0 and about 9.0, and a temperature between about 2° C. and about 37° C., for a time sufficient to allow assembly of VLPs; b) treating the VLPs with nuclease to remove any RNA protruding from the particles, and c) separating the VLPs from other process components.

In accordance with another aspect, there is provided a virus-like particle (VLP) prepared by the process according to the present invention.

In accordance with another aspect, there is provided a pharmaceutical composition comprising a VLP prepared by the process according to the present invention.

In accordance with another aspect, there is provided a VLP prepared by the process according to the present invention for use as an adjuvant In accordance with another aspect, there is provided a VLP prepared by the process according to the present invention for use to stimulate the innate immune response in a subject and thereby prevent, or decrease the severity of, a microbial infection in the subject.

In accordance with another aspect, there is provided a VLP prepared by the process according to the present invention for use in combination with one or more antigens as a vaccine.

In accordance with another aspect, there is provided a VLP prepared by the process according to the present invention in the manufacture of a medicament.

In accordance with another aspect, there is provided a method of enhancing an immune response to an antigen in a subject comprising administering to the subject an adjuvant comprising a VLP prepared by the process according to the present invention.

In accordance with another aspect, there is provided a method of stimulating the innate immune response in a subject and thereby prevent, or decrease the severity of, a microbial infection in the subject, comprising administering to the subject a VLP prepared by the process according to the present invention.

In accordance with another aspect, there is provided a method of stimulating an immune response in a subject comprising administering to the subject a VLP prepared by the process according to the present invention in combination with one or more antigens.

In accordance with another aspect of the present invention, there is provided a papaya mosaic virus (PapMV) virus-like particle (VLP) comprising recombinant PapMV coat protein and ssRNA, wherein the ssRNA is between about 50 nucleotides and about 5000 nucleotides in length and comprises a sequence corresponding to the nucleic acid sequence as set forth in SEQ ID NO:5 or 6, or a fragment thereof.

In accordance with another aspect of the present invention, there is provided a pharmaceutical composition comprising a papaya mosaic virus (PapMV) virus-like particle (VLP) comprising recombinant PapMV coat protein and ssRNA, wherein the ssRNA is between about 50 nucleotides and about 5000 nucleotides in length and comprises a sequence corresponding to the nucleic acid sequence as set forth in SEQ ID NO:5 or 6, or a fragment thereof.

In accordance with another aspect of the present invention, there is provided a papaya mosaic virus (PapMV) virus-like particle (VLP) comprising recombinant PapMV coat protein and ssRNA, wherein the ssRNA is between about 50 nucleotides and about 5000 nucleotides in length and comprises a sequence corresponding to the nucleic acid sequence as set forth in SEQ ID NO:5 or 6, or a fragment thereof, for use as an adjuvant.

In accordance with another aspect of the present invention, there is provided a papaya mosaic virus (PapMV) virus-like particle (VLP) comprising recombinant PapMV coat protein and ssRNA, wherein the ssRNA is between about 50 nucleotides and about 5000 nucleotides in length and comprises a sequence corresponding to the nucleic acid sequence as set forth in SEQ ID NO:5 or 6, or a fragment thereof, for use to stimulate the innate immune response in a subject and thereby prevent, or decrease the severity of, a microbial infection in the subject.

In accordance with another aspect of the present invention, there is provided a papaya mosaic virus (PapMV) virus-like particle (VLP) comprising recombinant PapMV coat protein and ssRNA, wherein the ssRNA is between about 50 nucleotides and about 5000 nucleotides in length and comprises a sequence corresponding to the nucleic acid sequence as set forth in SEQ ID NO:5 or 6, or a fragment thereof, for use in combination with one or more antigens as a vaccine.

In accordance with another aspect of the present invention, there is provided a papaya mosaic virus (PapMV) virus-like particle (VLP) comprising recombinant PapMV coat protein and ssRNA, wherein the ssRNA is between about 50 nucleotides and about 5000 nucleotides in length and comprises a sequence corresponding to the nucleic acid sequence as set forth in SEQ ID NO:5 or 6, or a fragment thereof, in the manufacture of a medicament.

In accordance with another aspect of the present invention, there is provided a method of enhancing an immune response to an antigen in a subject comprising administering to the subject an adjuvant comprising a papaya mosaic virus (PapMV) virus-like particle (VLP) comprising recombinant PapMV coat protein and ssRNA, wherein the ssRNA is between about 50 nucleotides and about 5000 nucleotides in length and comprises a sequence corresponding to the nucleic acid sequence as set forth in SEQ ID NO:5 or 6, or a fragment thereof.

In accordance with another aspect of the present invention, there is provided a method of stimulating the innate immune response in a subject and thereby prevent, or decrease the severity of, a microbial infection in the subject, comprising administering to the subject a papaya mosaic virus (PapMV) virus-like particle (VLP) comprising recombinant PapMV coat protein and ssRNA, wherein the ssRNA is between about 50 nucleotides and about 5000 nucleotides in length and comprises a sequence corresponding to the nucleic acid sequence as set forth in SEQ ID NO:5 or 6, or a fragment thereof.

In accordance with another aspect of the present invention, there is provided a method of stimulating an immune response in a subject comprising administering to the subject a papaya mosaic virus (PapMV) virus-like particle (VLP) comprising recombinant PapMV coat protein and ssRNA, wherein the ssRNA is between about 50 nucleotides and about 5000 nucleotides in length and comprises a sequence corresponding to the nucleic acid sequence as set forth in SEQ ID NO:5 or 6, or a fragment thereof, in combination with one or more antigens.

In accordance with another aspect of the present invention, there is provided an in vitro process for preparing papaya mosaic virus (PapMV) virus-like particles (VLPs) comprising the steps of: a) combining recombinant PapMV coat protein and ssRNA at a protein:RNA ratio of between about 5:1 and 40:1 by weight, in a buffered solution at a pH between about 6.5 and about 8.5, and a temperature between about 22° C. and about 37° C., for a time sufficient to allow assembly of VLPs, wherein the recombinant PapMV is predominantly in the form of low molecular weight species of less than 20-mers; b) treating the VLPs with nuclease to remove any RNA protruding from the particles, and c) separating the VLPs from other process components.

BRIEF DESCRIPTION OF THE DRAWINGS

These and other features of the invention will become more apparent in the following detailed description in which reference is made to the appended drawings.

FIG. 1 presents (A) the amino acid sequence of the wild-type PapMV coat protein (SEQ ID NO:1) and (B) the nucleotide sequence of the wild-type PapMV coat protein (SEQ ID NO:2).

FIG. 2 presents (A) the amino acid sequence of the modified PapMV coat protein CPΔN5 (SEQ ID NO:3), and (B) the amino acid sequence of modified PapMV coat protein PapMV CPsm (SEQ ID NO:4).

FIG. 7 presents (A) the sequence of the synthetic RNA template (SRT) [SEQ ID NO:5] used in one embodiment of the process according to the present invention, and (B) the sequence of the synthetic RNA template (SRT) [SEQ ID NO:6] used in another embodiment of the process according to the present invention; all ATG codons have been mutated for TAA stop codons (bold), the first 16 nucleotides are from the T7 transcription start site located within the pBluescript expression vector and the sequence comprises the PapMV nucleation site for rVLP assembly (boxed in (A)).

FIG. 8 presents electron micrographs of (A) PapMV VLPs self-assembled with ssRNA, and (B) PapMV VLPs self-assembled with poly I:C (dsRNA).

FIG. 12 presents graphs depicting compilation of (A) CD86 and (B) CD69 expression in DCs, CD8$^+$ T cells and B cells of C57BL/6, TLR7 knockout (KO), MYD88 KO and IRF5/7 KO mice 24 h after PapMV VLP ssRNA (100 μg) or PBS immunization. Results were analyzed by FACS and are presented as a ratio of the Mean Fluorescence Intensity (MFI) of the analyzed sample on the PBS sample.

FIG. 18 presents graphs depicting the proportion of CD8$^+$ T cells producing (A) IFN-γ, (B) TNF-α and (C) both cytokines after GP33 restimulation of splenocytes isolated from mice immunized with 100 μg PapMV VLP ssRNA, 100 μg R837 or PBS 6 hours before infection with $2\times10^6$ pfu LCMV clone 13 and sacrificed 15 days post-infection; (D) amount of IFN-γ and (E) amount of TNF-α produced by CD8$^+$ T cells after GP33 restimulation, (F) Mean Fluorescence Intensity (MFI) of PD-1 expression in GP33 specific CD8$^+$ T lymphocytes, and (G) percentage of DbGP33$^+$CD8$^+$CD44$^+$ in splenocytes.

FIG. 26 presents graphs depicting the IgG and IgG2a titers measured in the blood of mice immunized intranasally with PapMV VLPs combined with the trivalent inactivated flu vaccine (TIV), (A) total IgG titers after one immunization, (B) total IgG titers after two immunizations at 14-day intervals, and (C) IgG2a titers measured after two immunizations.

FIG. 31 presents graphs showing (A) weight loss, and (B) symptoms in mice immunized with NP from influenza virus H1N1 A/california/7/2009 alone or mixed with PapMV VLPs as adjuvant and challenged with the heterosubtypic strain H1N1 WSN/33. Symptoms are as described in FIG. 9.

FIG. 32 presents a comparison of the adjuvant effect on the trivalent influenza vaccine (TIV) of PapMV sm VLPs ("PapMV sm") and PapMV VLPs prepared by the process according to the present invention (PapMV new"), (A) titers of total IgG directed to TIV, and (B) titers of IgG2 directed to TIV.

DETAILED DESCRIPTION OF THE INVENTION

Figure 3:
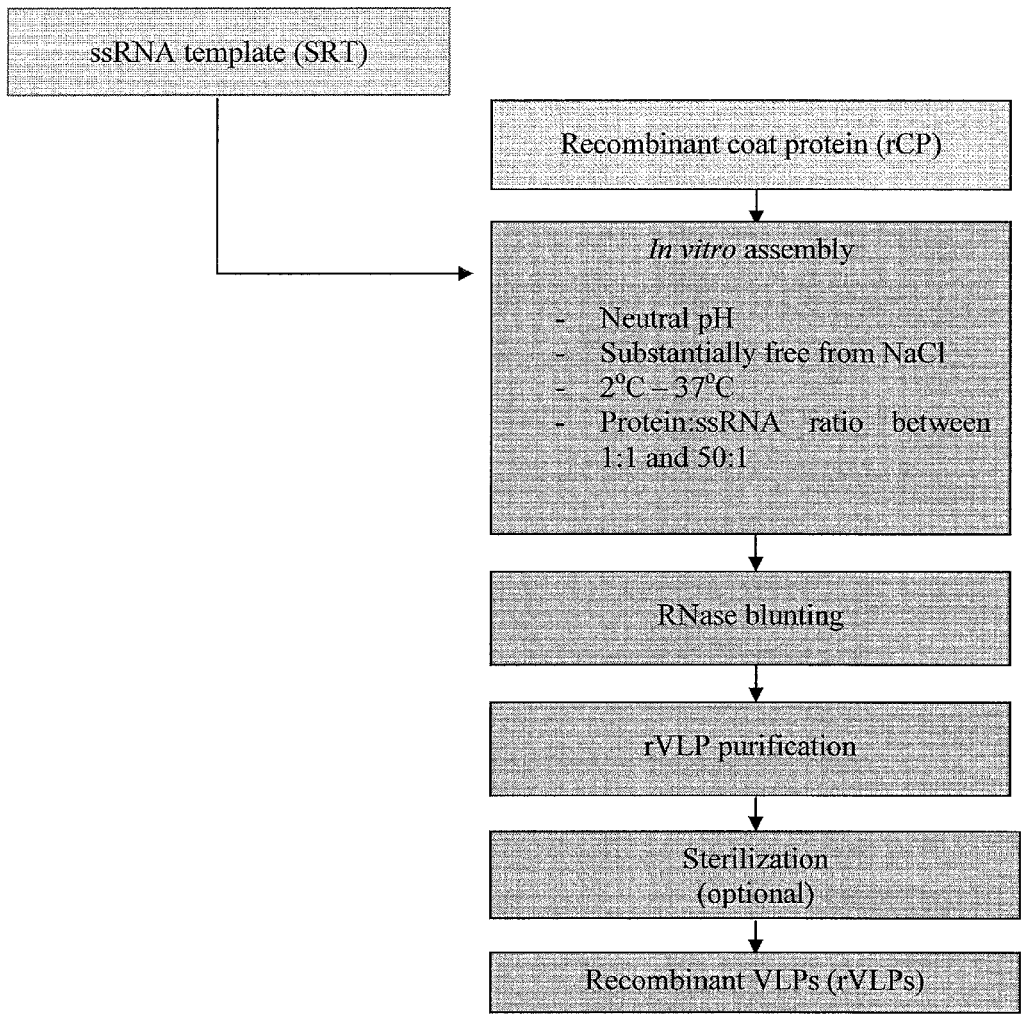
FIG. 3 presents a flow chart outlining the steps for the preparation of in vitro assembled PapMV VLPs containing ssRNA in accordance with one embodiment of the invention (rCP=recombinant PapMV coat protein; SRT=synthetic RNA template; rVLP=recombinant VLP).
Figure 4:
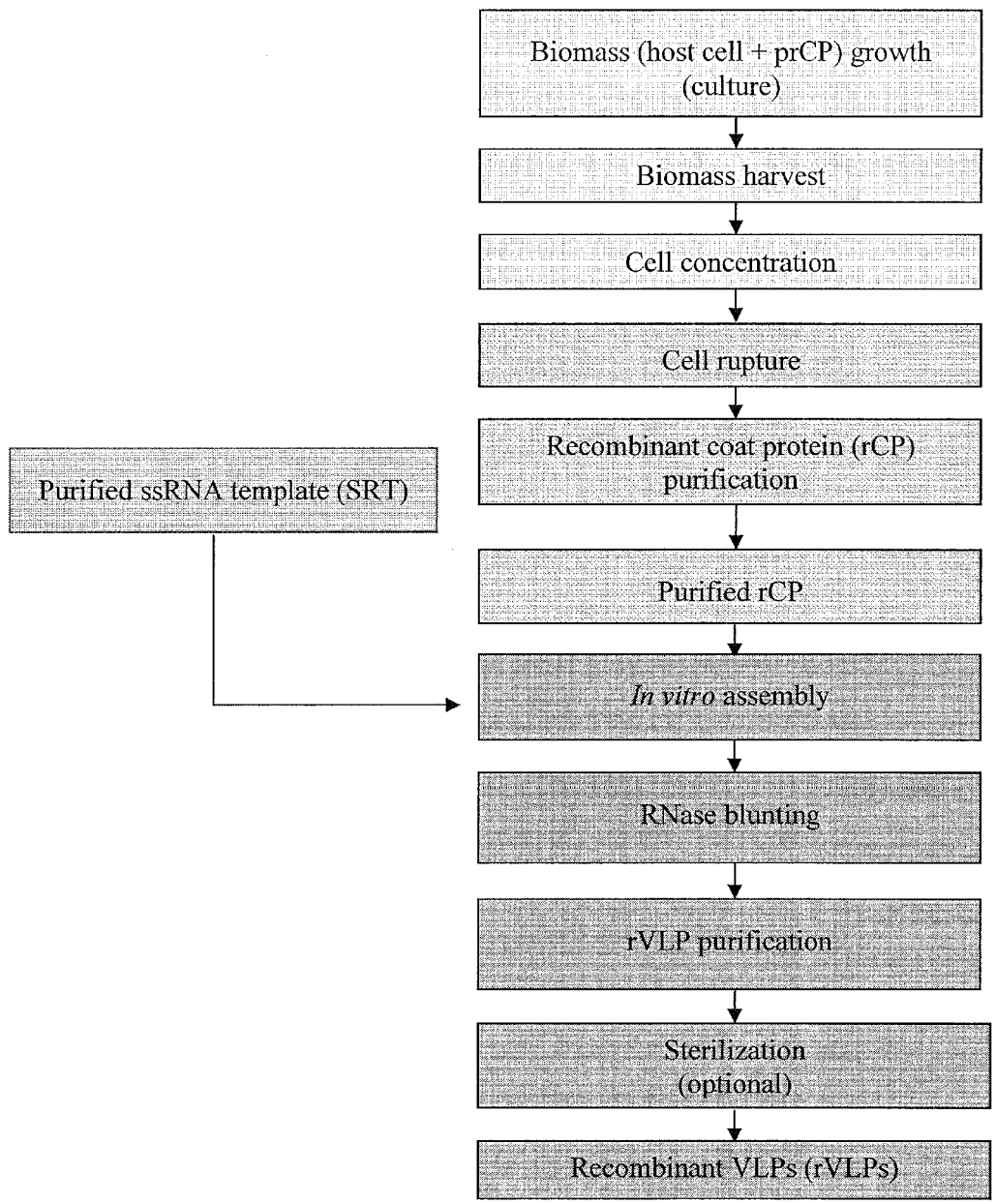
FIG. 4 presents a flow chart outlining the steps for the preparation of in vitro assembled PapMV VLPs containing ssRNA in accordance with one embodiment of the invention (abbreviations as for FIG. 3; prCP=plasmid encoding rCP).
Figure 5:
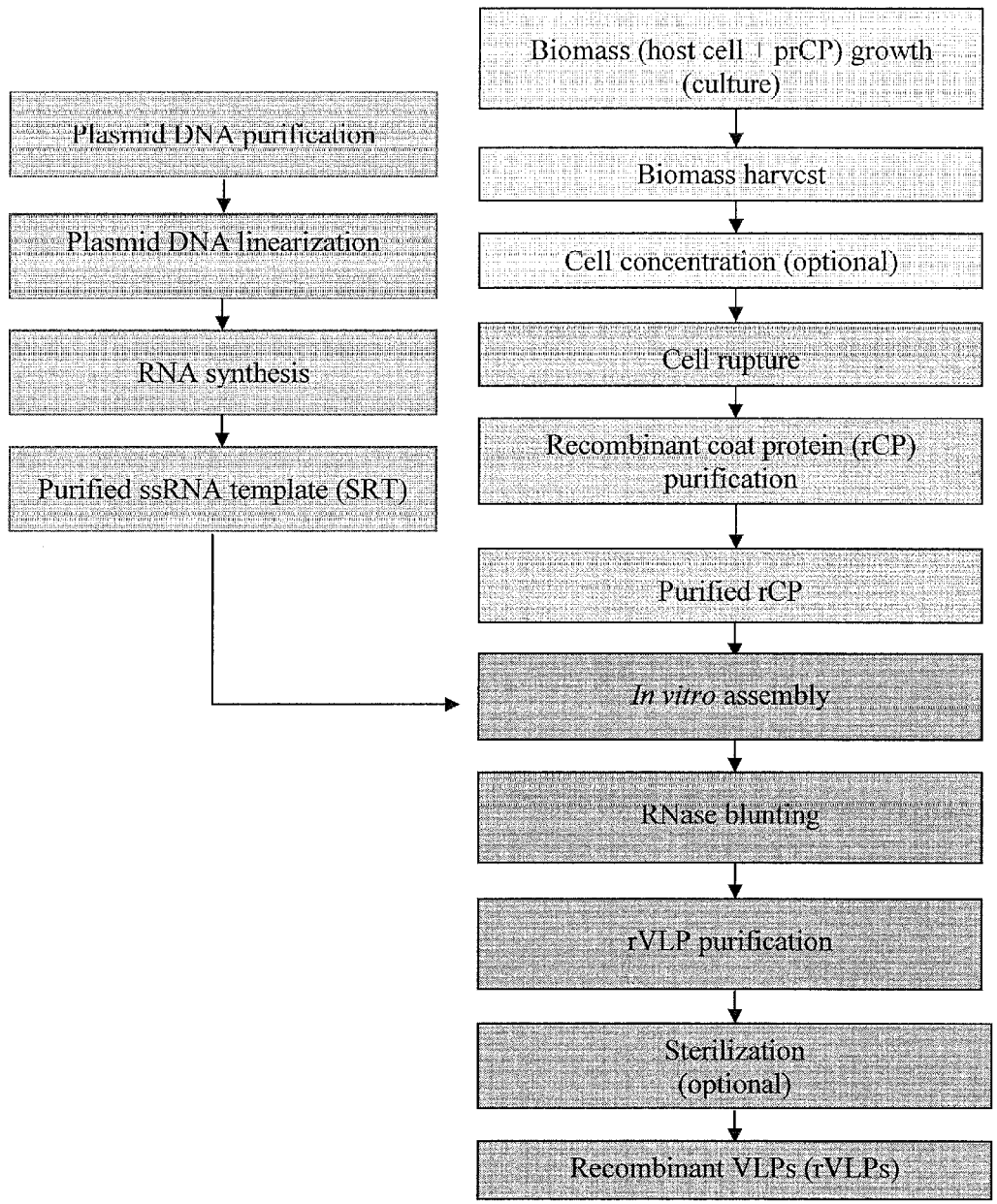
FIG. 5 presents a flow chart outlining the steps for the preparation of in vitro assembled PapMV VLPs containing ssRNA in accordance with one embodiment of the invention (abbreviations as for FIG. 4).

The present invention provides for an in vitro process of preparing papaya mosaic virus (PapMV) virus-like particles (VLPs) from recombinant PapMV coat protein and ssRNA, which allows for large scale production of PapMV VLPs in high yields.

Previous methods of preparing PapMV VLPs from monomeric recombinant PapMV coat protein (as described in Tremblay, et al., 2006, ibid.) allowed recovery of approximately 20% of the total expressed PapMV coat protein in the form of VLPs. After ultracentrifugation of the expressed coat protein isolated from the host cells, only the pellet containing the VLPs was retained and the remaining approximately 80% of the PapMV coat protein in the supernatant (containing lower molecular weight forms of the PapMV coat protein, including monomers, dimers, and discs of up to 20-mers) was discarded. In contrast, the in vitro process described herein uses the low molecular weight forms of the PapMV coat protein (primarily, but not exclusively, monomers) recovered from the host cell and can provide for up to about 80% of the PapMV coat protein being converted into VLPs. Accordingly, in certain embodiments, the process according to the present invention results in a 3-4 fold decrease in the loss of PapMV coat protein (and thus, consequently, an increase of 3-4 fold in the yield of VLPs obtained per liter of cell culture). Such an improvement is advantageous for large scale manufacturing and also reduces the cost of production.

In addition, the in vitro process according to the present invention eliminates the need for detergent, which is required in order to remove LPS from the PapMV coat protein, which is isolated from the bacterial cells in the form of VLPs in the method described by Tremblay, et al., (2006, ibid.). As is known in the art, detergent can be difficult to remove from protein preparations and thus residual amounts may remain in the final VLP preparations prepared by previous methods. In certain embodiments, therefore, the process according to the present invention allows for preparation of VLPs with minimal batch-to-batch variation.

While various ssRNAs may be used in the process according to the present invention, in certain embodiments, synthetic ssRNA is used. The use of synthetic sequences can, for example, allow for consistency in the final product, as well as allowing for manipulation of the sequences if necessary to minimize possibilities of in vivo transcription.

Certain embodiments of the present invention also provide for PapMV VLPs comprising ssRNA prepared by the process described herein. As described herein, certain embodiments provide for PapMV VLPs comprising ssRNA that activate toll-like receptor 7 (TLR-7), which is located in the endosome, and/or stimulate interferon-alpha production. In contrast, PapMV VLPs produced by self-assembly in *E. coli* cells appear to target more strongly TLR-2 and CD14, which are located at the surface of immune cells. Without being bound by any particular theory, it is believed that preparation of VLPs by the process according to the present invention may allow the VLPs to more efficiently enter the endosome and interact with TLR-7, whereas the use of detergent in VLP preparation results in change in structure and a more prominent interaction with TLR-2 at the cell surface. In addition, PapMV VLPs comprising ssRNA prepared by the process according to the present invention tend to be more immunogenic and more effective adjuvants than PapMV VLPs prepared by the method described by Tremblay, et al., (2006, ibid.) (see, for example, Example 19).

The PapMV VLPs comprising ssRNA provided by the present invention are useful as adjuvants to enhance the immunogenicity of antigens, including commercial vaccines, and, when used alone, as stimulators of the innate immune response to provide protective and/or therapeutic effects.

Definitions

Unless defined otherwise, all technical and scientific terms used herein have the same meaning as commonly understood by one of ordinary skill in the art to which this invention belongs.

As used herein, the term "about" refers to approximately a +/−10% variation from a given value. It is to be understood that such a variation is always included in any given value provided herein.

The use of the word "a" or "an" when used herein in conjunction with the term "comprising" may mean "one," but it is also consistent with the meaning of "one or more," "at least one" and "one or more than one."

As used herein, the words "comprising" (and grammatical variations thereof, such as "comprise" and "comprises"), "having" (and grammatical variations thereof, such as "have" and "has"), "including" (and grammatical variations thereof, such as "includes" and "include") or "containing" (and grammatical variations thereof, such as "contains" and "contain") are inclusive or open-ended and do not exclude additional, unrecited elements or method steps.

"Naturally occurring," as used herein, as applied to an object, refers to the fact that an object can be found in nature. For example, an organism, or a polypeptide or polynucleotide sequence that is present in an organism that can be isolated from a source in nature and which has not been intentionally modified by man in the laboratory is naturally occurring.

The terms "attenuate," "inhibit," "prevent" and grammatical variations thereof, as used herein, refer to a measurable decrease in a given parameter or event.

The term "vaccine," as used herein, refers to a composition capable of producing a beneficial immune response when administered to a subject.

The term "pathogen," as used herein, refers to an organism capable of causing a disease or disorder in a host including, but not limited to, bacteria, viruses, protozoa, fungi and parasites.

The term "subject" or "patient" as used herein refers to an animal in need of treatment.

The term "animal," as used herein, refers to both human and non-human animals, including, but not limited to, mammals, birds and fish, and encompasses domestic, farm, zoo, laboratory and wild animals, such as, for example, cows, pigs, horses, goats, sheep or other hoofed animals, dogs, cats, chickens, ducks, non-human primates, guinea pigs, rabbits, ferrets, rats, hamsters and mice.

Administration of VLPs "in combination with" one or more further therapeutic agents is intended to include simultaneous (concurrent) administration and consecutive administration. Consecutive administration is intended to encompass various orders of administration of the therapeutic agent(s) and the VLPs to the subject with administration of the therapeutic agent(s) and the VLPs being separated by a defined time period that may be short (for example in the order of minutes) or extended (for example in the order of days or weeks).

The terms "immune stimulation" and "immunostimulation" as used interchangeably herein, refer to the ability of a molecule that is unrelated to an animal pathogen or disease to provide protection against infection by the pathogen or against the disease by stimulating the immune system and/or improving the capacity of the immune system of the animal to respond to the infection or disease. Immuno stimulation may have a prophylactic effect, a therapeutic effect, or a combination thereof.

The term "substantially identical," as used herein in relation to a nucleic acid or amino acid sequence indicates that, when optimally aligned, for example using the methods described below, the nucleic acid or amino acid sequence shares at least 70%, at least 75%, at least 80%, at least 85%, at least 90%, at least 95%, at least 96%, at least 97%, at least 98% or at least 99% sequence identity with a defined second nucleic acid or amino acid sequence (or "reference sequence"). "Substantial identity" may be used to refer to various types and lengths of sequence, such as full-length sequence, functional domains, coding and/or regulatory sequences, promoters, and genomic sequences. Percent identity between two amino acid or nucleic acid sequences can be determined in various ways that are within the skill of a worker in the art, for example, using publicly available computer software such as Smith Waterman Alignment (Smith, T. F. and M. S. Waterman (1981) *J Mol Biol* 147:195-7); "BestFit" (Smith and Waterman, *Advances in Applied Mathematics,* 482-489 (1981)) as incorporated into GeneMatcher Plus™, Schwarz and Dayhof (1979) *Atlas of Protein Sequence and Structure*, Dayhof, M. O., Ed pp 353-358; BLAST program (Basic Local Alignment Search Tool (Altschul, S. F., W. Gish, et al. (1990) *J Mol Biol* 215: 403-10), and variations thereof including BLAST-2, BLAST-P, BLAST-N, BLAST-X, WU-BLAST-2, ALIGN, ALIGN-2, CLUSTAL, and Megalign (DNASTAR) software. In addition, those skilled in the art can determine appropriate parameters for measuring alignment, including algorithms needed to achieve maximal alignment over the length of the sequences being compared. In general, for amino acid sequences, the length of comparison sequences will be at least 10 amino acids. One skilled in the art will understand that the actual length will depend on the overall length of the sequences being compared and may be at least 20, at least 30, at least 40, at least 50, at least 60, at least 70, at least 80, at least 90, at least 100, at least 110, at least 120, at least 130, at least 140, at least 150, or at least 200 amino acids, or it may be the full-length of the amino acid sequence. For nucleic acids, the length of comparison sequences will generally be at least 25 nucleotides, but may be at least 50, at least 100, at least 125, at least 150, at least 200, at least 250, at least 300, at least 350, at least 400, at least 450, at least 500, at least 550, or at least 600 nucleotides, or it may be the full-length of the nucleic acid sequence.

The terms "corresponding to" or "corresponds to" indicate that a nucleic acid sequence is identical to all or a portion of a reference nucleic acid sequence. In contradistinction, the term "complementary to" is used herein to indicate that the nucleic acid sequence is identical to all or a portion of the complementary strand of a reference nucleic acid sequence. For illustration, the nucleic acid sequence "TATAC" corresponds to a reference sequence "TATAC" and is complementary to a reference sequence "GTATA." The terms "corresponding to" and "corresponds to" when used herein to cross-reference a DNA and RNA sequence indicate that the DNA sequence is identical to all of a portion of the reference RNA sequence (or vice versa), however, the DNA sequence will contain thymine (T) residues at positions corresponding to uracil (U) residues in the RNA sequence. Thus, for illustration, the DNA sequence "TATAC" corresponds to an RNA reference sequence "UAUAC."

It is contemplated that any embodiment discussed herein can be implemented with respect to any method or composition of the invention, and vice versa. Furthermore, compositions and kits of the invention can be used to achieve methods of the invention.

Process for Preparing Virus-Like Particles

The process in accordance with the present invention allows for the in vitro assembly of recombinant coat protein and a ssRNA (referred to herein as a ssRNA template or "SRT") to form VLPs.

While the process is described throughout with reference to PapMV coat protein, one skilled in the art would readily appreciate that the process is equally applicable to other potexvirus coat (or capsid) proteins. The sequences of the coat proteins and genomes of numerous potexviruses are known in the art and are available from public databases, such as GenBank.

Exemplary embodiments of the process of the invention are provided in FIGS. 3-6. In brief, the process comprises combining recombinant coat protein and the SRT at neutral pH and a temperature of between about 2° C. and 37° C., at a protein:RNA ratio of between about 1:1 and about 50:1 by weight for a time sufficient to allow formation of VLPs. The VLPs are subsequently treated with nuclease to remove any RNA protruding from the VLPs, then submitted to one or more purification steps to provide the final recombinant VLPs (see FIG. 3, for example). Certain embodiments of the process may further comprise isolating the recombinant protein from the host cell in which it was expressed (see FIG. 4, for example) and/or preparation of the SRT from plasmid DNA (see FIG. 5, for example).

The process according to the present invention is amenable to scale-up and thus, in certain embodiments, the present invention provides for a large scale process suitable for production of large quantities of VLPs in high yield.

PapMV Coat Protein

The PapMV coat protein used to prepare the VLPs can be the entire PapMV coat protein, or part thereof, or it can be a genetically modified version of the wild-type PapMV coat protein, for example, comprising one or more amino acid deletions, insertions, replacements and the like, provided that the coat protein retains the ability to self-assemble into a VLP. The amino acid sequence of the wild-type PapMV coat (or capsid) protein is known in the art (see, Sit, et al., 1989, *J. Gen. Viral.*, 70:2325-2331, and GenBank Accession No. NP_044334.1) and is provided herein as SEQ ID NO:1 (see FIG. 1A). Variants of this sequence are known, for example, the sequences of coat proteins of Mexican isolates of PapMV described by Noa-Carrazana & Silva-Rosales (2001, *Plant Science*, 85:558) have 88% identity with SEQ ID NO:1 and are available from GenBank. The nucleotide sequence of the PapMV coat protein is also known in the art (see, Sit, et al., ibid., and GenBank Accession No. NC_001748 (nucleotides 5889-6536)) and is provided herein as SEQ ID NO:2 (see FIG. 1B).

As noted above, the amino acid sequence of the PapMV coat protein need not correspond precisely to the parental (wild-type) sequence, i.e. it may be a "variant sequence." For example, the PapMV coat protein may be mutagenized by substitution, insertion or deletion of one or more amino acid residues so that the residue at that site does not correspond to the parental (reference) sequence. One skilled in the art will appreciate, however, that such mutations will not be extensive and will not dramatically affect the ability of the recombinant PapMV CP to assemble into VLPs.

Recombinant PapMV CPs prepared using fragments of the wild-type coat protein that retain the ability to multimerise and assemble into a VLP (i.e. are "functional" fragments) are, therefore, also contemplated by the present invention for use in the process. For example, a fragment may comprise a deletion of one or more amino acids from the N-terminus, the C-terminus, or the interior of the protein, or a combination thereof. In general, functional fragments are at least 100 amino acids in length, for example, at least 150 amino acids, at least 160 amino acids, at least 170 amino acids, at least 180 amino acids, or at least 190 amino acids in length. Deletions made at the N-terminus of the wild-type protein should generally delete fewer than 13 amino acids in order to retain the ability of the protein to self-assemble.

In certain embodiments of the present invention, when a recombinant coat protein comprises a variant sequence, the variant sequence is at least about 70% identical to the reference sequence, for example, at least about 75%, at least about 80%, at least about 85%, at least about 90%, at least about 95%, at least about 97% identical, or at least about 98% identical to the reference sequence. In certain embodiments, the reference amino acid sequence is SEQ ID NO:1 (FIG. 1A).

In certain embodiments of the present invention, the PapMV coat protein used to prepare the recombinant PapMV VLPs is a genetically modified (i.e. variant) version of the PapMV coat protein. In some embodiments, the PapMV coat protein has been genetically modified to delete amino acids from the N- or C-terminus of the protein and/or to include one or more amino acid substitutions. In some embodiments, the PapMV coat protein has been genetically modified to delete between about 1 and about 10 amino acids from the N- or C-terminus of the protein, for example between about 1 and about 5 amino acids.

In certain embodiments, the PapMV coat protein has been genetically modified to remove one of the two methionine codons that occur proximal to the N-terminus of the wild-type protein (i.e. at positions 1 and 6 of SEQ ID NO:1) and can initiate translation. Removal of one of the translation initiation codons allows a homogeneous population of proteins to be produced. The selected methionine codon can be removed, for example, by substituting one or more of the nucleotides that make up the codon such that the codon codes for an amino acid other than methionine, or becomes a nonsense codon. Alternatively all or part of the codon, or the 5' region of the nucleic acid encoding the protein that includes the selected codon, can be deleted. In some embodiments of the present invention, the PapMV coat protein has been genetically modified to delete between 1 and 5 amino acids from the N-terminus of the protein. In some embodiments, the genetically modified PapMV coat protein has an amino acid sequence substantially identical to SEQ ID NO:3 (FIG. 2A) and may optionally comprise a histidine tag of up to 6 histidine residues. In some embodiments, the PapMV coat protein has been genetically modified to include additional amino acids (for example between about 1 and about 8 amino acids) at the C-terminus that result from the inclusion of one or more specific restriction enzyme sites into the encoding nucleotide sequence. In some embodiments, the PapMV coat protein has an amino acid sequence substantially identical to SEQ ID NO:4 (FIG. 2B) with or without the histidine tag.

When the recombinant PapMV VLPs are prepared using a variant PapMV coat protein sequence that contains one or more amino acid substitutions, these can be "conservative" substitutions or "non-conservative" substitutions. A conservative substitution involves the replacement of one amino acid residue by another residue having similar side chain properties. As is known in the art, the twenty naturally occurring amino acids can be grouped according to the physicochemical properties of their side chains. Suitable groupings include alanine, valine, leucine, isoleucine, proline, methionine, phenylalanine and tryptophan (hydrophobic side chains); glycine, serine, threonine, cysteine, tyrosine, asparagine, and glutamine (polar, uncharged side chains); aspartic acid and glutamic acid (acidic side chains) and lysine, arginine and histidine (basic side chains). Another grouping of amino acids is phenylalanine, tryptophan, and tyrosine (aromatic side chains). A conservative substitution involves the substitution of an amino acid with another amino acid from the same group. A non-conservative substitution involves the replacement of one amino acid residue by another residue having different side chain properties, for example, replacement of an acidic residue with a neutral or basic residue, replacement of a neutral residue with an acidic or basic residue, replacement of a hydrophobic residue with a hydrophilic residue, and the like.

In certain embodiments of the present invention, the variant sequence comprises one or more non-conservative substitutions. Replacement of one amino acid with another having different properties may improve the properties of the coat protein. For example, as previously described, mutation of residue 128 of the coat protein improves assembly of the protein into VLPs (Tremblay et al. 2006, *FEBS J.*, 273:14-25). In some embodiments of the present invention, therefore, the coat protein comprises a mutation at residue 128 of the coat protein in which the glutamic acid residue at this position is substituted with a neutral residue. In some embodiments, the glutamic acid residue at position 128 is substituted with an alanine residue.

Substitution of the phenylalanine residue at position F13 of the wild-type PapMV coat protein with another hydrophobic residue has been shown to result in a higher proportion of VLPs being formed when the recombinant protein is expressed than when the wild-type protein sequence is used (Laliberté-Gagné, et al., 2008, *FEBS J.*, 275:1474-1484). In the context of the present invention, the following amino acid residues are considered to be hydrophobic residues suitable for substitution at the F13 position: Ile, Trp, Leu, Val, Met and Tyr. In some embodiments of the invention, the coat protein comprises a substitution of Phe at position 13 with Ile, Trp, Leu, Val, Met or Tyr. In some embodiments, the coat protein comprises a substitution of Phe at position 13 with Leu or Tyr.

In certain embodiments, mutation at position F13 of the coat protein may be combined with a mutation at position E128, a deletion at the N-terminus, or a combination thereof.

Likewise, the nucleic acid sequence encoding the PapMV coat protein used to prepare the recombinant PapMV coat protein need not correspond precisely to the parental reference sequence but may vary by virtue of the degeneracy of the genetic code and/or such that it encodes a variant amino acid sequence as described above. In certain embodiments of the present invention, therefore, the nucleic acid sequence encoding the variant coat protein is at least about 70% identical to the reference sequence, for example, at least about 75%, at least about 80%, at least about 85% or at least about 90% identical to the reference sequence. In certain embodiments, the reference nucleic acid sequence is SEQ ID NO:2 (FIG. 1B).

In certain embodiments, the coat protein is a fusion protein that comprises the PapMV coat protein or variant thereof, fused to one or more antigenic peptides. The peptide(s) may be fused at the C-terminus, the N-terminus or at an internal position provided that the coat protein may still assemble into a VLP (see, for example, International Patent Application Nos. PCT/CA2007/002069 (WO 2008/058396), PCT/CA2007/001904 (WO 2008/058369), PCT/CA2008/000154 (WO 2008/089569) and PCT/CA2009/00636 (WO 2010/012069)). As described in more detail below, the antigenic peptide may be derived from a virus, bacteria, fungus or other pathogen, or it may be an allergen or a tumour-associated antigen.

Suitable antigenic peptides can vary in size, but in general are between about 3 amino acids and about 50 amino acids in length, for example between about 3 and about 40 amino acids in length. In some embodiments, the antigenic peptide is at least 5, at least 6 or at least 7 amino acids in length and up to about 50, 40, 35, 30, 25 or 20 amino acids in length.

Preparation of Recombinant Coat Protein

Recombinant PapMV coat proteins for the preparation of PapMV VLPs can be readily prepared by standard genetic engineering techniques by the skilled worker. Methods of genetically engineering proteins are well known in the art (see, for example, Ausubel et al. (1994 & updates) *Current Protocols in Molecular Biology*, John Wiley & Sons, New York), as is the sequence of the wild-type PapMV coat protein (see, for example, SEQ ID NOs:1 and 2).

For example, isolation and cloning of the nucleic acid sequence encoding the wild-type protein can be achieved using standard techniques (see, for example, Ausubel et al., ibid.). For example, the nucleic acid sequence can be obtained directly from the PapMV by extracting RNA by standard techniques and then synthesizing cDNA from the RNA template (for example, by RT-PCR). PapMV can be purified from infected plant leaves that show mosaic symptoms by standard techniques.

The nucleic acid sequence encoding the coat protein is then inserted directly or after one or more subcloning steps into a suitable expression vector. One skilled in the art will appreciate that the precise vector used is not critical to the instant invention. Examples of suitable vectors include, but are not limited to, plasmids, phagemids, cosmids, bacteriophage, baculoviruses, retroviruses or DNA viruses. The coat protein can then be expressed and purified as described previously and below. In general the vector and corresponding host cell are selected such that the recombinant coat protein is expressed in the cells as low molecular weight species and not as VLPs. Selection of appropriate vector and host cell combinations in this regard is well within the ordinary skills of a worker in the art.

Alternatively, the nucleic acid sequence encoding the coat protein can be further engineered to introduce one or more mutations, such as those described above, by standard in vitro site-directed mutagenesis techniques well-known in the art. Mutations can be introduced by deletion, insertion, substitution, inversion, or a combination thereof, of one or more of the appropriate nucleotides making up the coding sequence. This can be achieved, for example, by PCR-based techniques for which primers are designed that incorporate one or more nucleotide mismatches, insertions or deletions. The presence of the mutation can be verified by a number of standard techniques, for example by restriction analysis or by DNA sequencing.

One of ordinary skill in the art will appreciate that the DNA encoding the coat protein can be altered in various ways without affecting the activity of the encoded protein. For example, variations in DNA sequence may be used to optimize for codon preference in a host cell used to express the protein, or may contain other sequence changes that facilitate expression.

One skilled in the art will understand that the expression vector may further include regulatory elements, such as transcriptional elements, required for efficient transcription of the DNA sequence encoding the coat or fusion protein. Examples of regulatory elements that can be incorporated into the vector include, but are not limited to, promoters, enhancers, terminators, and polyadenylation signals. Certain embodiments of the present invention, therefore, provide vectors comprising a regulatory element operatively linked to a nucleic acid sequence encoding a genetically engineered coat protein. One skilled in the art will appreciate that selection of suitable regulatory elements is dependent on the host cell chosen for expression of the genetically engineered coat protein and that such regulatory elements may be derived from a variety of sources, including bacterial, fungal, viral, mammalian or insect genes.

In the context of the present invention, the expression vector may additionally contain heterologous nucleic acid sequences that facilitate the purification of the expressed protein. Examples of such heterologous nucleic acid sequences include, but are not limited to, affinity tags such as metal-affinity tags, histidine tags, avidin/streptavidin encoding sequences, glutathione-S-transferase (UST) encoding sequences and biotin encoding sequences. The amino acids encoded by the heterologous nucleic acid sequence can be removed from the expressed coat protein prior to use according to methods known in the art. Alternatively, the amino acids corresponding to expression of heterologous nucleic acid sequences can be retained on the coat protein if they do not interfere with its subsequent assembly into VLPs.

In one embodiment of the present invention, the coat protein is expressed as a histidine tagged protein. The histidine tag can be located at the carboxyl terminus or the amino terminus of the coat protein.

The expression vector can be introduced into a suitable host cell or tissue by one of a variety of methods known in the art. Such methods can be found generally described in Ausubel et al. (ibid.) and include, for example, stable or transient transfection, lipofection, electroporation, and infection with recombinant viral vectors. One skilled in the art will understand that selection of the appropriate host cell for expression of the coat protein will be dependent upon the vector chosen. Examples of host cells include, but are not limited to, bacterial, yeast, insect, plant and mammalian cells. The precise host cell used is not critical to the invention. The coat proteins can be produced in a prokaryotic host (e.g. *E. coli, A. salmonicida* or *B. subtilis*) or in a eukaryotic host (e.g. *Saccharomyces* or *Pichia*; mammalian cells, e.g. COS, NIH 3T3, CHO, BHK, 293 or HeLa cells; insect cells or plant cells).

In certain embodiments, the coat protein is expressed in *E. coli* or *P. pastoris*.

If desired, the coat proteins can be purified from the host cells by standard techniques known in the art (see, for example, in *Current Protocols in Protein Science*, ed. Coligan, J. E., et al, Wiley & Sons, New York, N.Y.) and sequenced by standard peptide sequencing techniques using either the intact protein or proteolytic fragments thereof to confirm the identity of the protein.

ssRNA Template

The ssRNA template for use in the process according to the present invention may be, for example, synthetic ssRNA, a naturally occurring ssRNA, a modified naturally occurring ssRNA, a fragment of a naturally occurring or synthetic ssRNA, or the like.

Typically, the ssRNA for in vitro assembly is at least about 50 nucleotides in length and up to about 5000 nucleotides in length, for example, at least about 100, 250, 300, 350, 400, 450 or 500 nucleotides in length and up to about 5000, 4500, 4000 or 3500 nucleotides in length. In certain embodiments, the ssRNA for in vitro assembly is between about 500 and about 3000 nucleotides in length, for example, between about 1000 and about 3000 nucleotides in length, or between about 1200 and about 2800 nucleotides in length.

In certain embodiments, the ssRNA template is designed such that it does not include any ATG (AUG) start codons in order to minimize the chances of in vivo transcription of the sequences. The use of ssRNA templates including ATG start codons is not, however, excluded as in vivo transcription remains unlikely if the ssRNA is not capped.

In certain embodiments, the ssRNA for in vitro assembly includes between about 38 and about 100 nucleotides from the 5'-end of the native PapMV RNA, which contain at least part of the putative packaging signal. ssRNA templates that do not include the putative packaging signal can also be used in certain embodiments. Non-limiting examples of sequences based on the PapMV genome that may be used to produce ssRNA templates are provided in FIG. 7 [SEQ ID NOs: 5 and 6]. Fragments of these sequences, as well as elongated versions of up to 5000 nucleotides, are also contemplated for use to produce ssRNA templates in certain embodiments of the invention. In certain embodiments, the ssRNA for in vitro assembly comprise a sequence corresponding to nucleotides 17 to 54 of SEQ ID NO:5. In certain embodiments, the ssRNA for in vitro assembly comprise a sequence corresponding to nucleotides 17 to 63 of SEQ ID NO:5.

ssRNA sequences that are rich in A and C nucleotides are also known to assemble with PapMV coat protein (Sit, et al., 1994, *Virology*, 199:238-242). Accordingly, in certain embodiments, the ssRNA template is an A and/or C rich sequence, including poly-A and poly-C ssRNA templates. ssRNA templates based on all or part of the sequences of other potexviruses, such as potato virus X (PVX), clover yellow mosaic virus (CYMV), potato aucuba mosaic virus (PAMV) and malva mosaic virus (MaMV), are also contemplated for use in the process in some embodiments.

Preparation of ssRNA Template

The ssRNA template can be isolated and/or prepared by standard techniques known in the art (see, for example, Ausubel et al. (1994 & updates) *Current Protocols in Molecular Biology*, John Wiley & Sons, New York).

For example, for synthetic ssRNA, the sequence encoding the ssRNA template can be inserted into a suitable plasmid which can be used to transform an appropriate host cell. After culture of the transformed host cells under appropriate cell culture conditions, plasmid DNA can be purified from the cell culture by standard molecular biology techniques and linearized by restriction enzyme digestion.

The ssRNA is then transcribed using a suitable RNA polymerase and the transcribed product purified by standard protocols.

One skilled in the art will appreciate that the precise plasmid used is not critical to the invention provided that it is capable of achieving its desired purpose. Likewise the particular host cell used is not critical so long as it is capable of propagating the selected plasmid.

Shorter ssRNA templates may also be synthesized chemically using standard techniques. A number of commercial RNA synthesis services are also available.

The final ssRNA template may optionally be sterilized prior to use.

In Vitro Assembly of VLPs

The assembly reaction is conducted in vitro using the prepared recombinant coat protein and ssRNA template. While both the recombinant coat protein and ssRNA template are typically purified prior to assembly, the use of crude preparations or partially purified coat protein and/or ssRNA template is also contemplated in some embodiments.

In general, preparations of recombinant coat proteins having identical amino acid sequences are employed in the assembly reaction, such that the final VLP when assembled comprises identical coat protein subunits. The use of preparations comprising a plurality of recombinant coat proteins having different amino acid sequences, such that the final VLP when assembled comprises variations in its coat protein subunits, are also contemplated in some embodiments.

The recombinant coat protein used in the assembly reaction is predominantly in the form of low molecular weight species consisting primarily of monomers and dimers, but also including other low molecular weight species of less than 20-mers. In the context of the present invention, a recombinant coat protein preparation is considered to be predominantly in the form of low molecular weight species when at least about 70% of the coat protein comprised by the preparation is present as low molecular weight species. In certain embodiments, at least about 75%, 80%, 85%, 90% or 95% of the coat protein in the recombinant coat protein preparation used in the assembly reaction is present as low molecular weight species. In certain embodiments of the present invention, the recombinant coat protein preparation is comprised of at least about 50% monomers and dimers, for example, about 60%, 70%, 75% or 80% monomers and dimers.

The assembly reaction is conducted in a neutral aqueous solution and does not require any other particular ion. Typically, a buffer solution is used. The pH should be in the range of about pH6.0 to about pH9.0, for example, between about pH6.5 and about pH9.0, between about pH7.0 and about pH9.0, between about pH6.0 and about pH8.5, between about pH6.5 and about pH8.5, or between about pH7.0 and about pH8.5.

The nature of the buffer is not critical to the invention provided that it can maintain the pH in the ranges described above. Examples of buffers for use within the pH ranges described above include, but are not limited to, Tris buffer, phosphate buffer, citrate buffer and the like.

The presence of high concentrations of sodium chloride (NaCl) may impact the assembly of PapMV coat protein. In certain embodiments, therefore, the assembly reaction is conducted in a solution that is substantially free of NaCl, for example, containing less than 0.05M NaCl.

The assembly reaction can be conducted using various protein:ssRNA ratios. In general, a protein:ssRNA ratio between about 1:1 and about 50:1 by weight may be used, for example, between at least about 1:1, 2:1, 3:1, 4:1 or 5:1 by weight and no more than about 50:1, 40:1 or 30:1 by weight. In certain embodiments, the protein:ssRNA ratio used in the assembly reaction is between about 5:1 and about 40:1, or between about 10:1 and about 40:1 by weight.

The assembly reaction can be conducted at temperatures varying from about 2° C. to about 37° C., for example, between at least about 3° C., 4° C., 5° C., 6° C., 7° C., 8° C., 9° C. or 10° C. and about 37° C., 35° C., 30° C. or 28° C. In certain embodiments, the assembly reaction is conducted at a temperature between about 15° C. and about 37° C., for example, between about 20° C. and about 37° C., or between about 22° C. and about 37° C.

The assembly reaction is allowed to proceed for a sufficient period of time to allow VLPs to form. The time period will vary depending on the concentrations of recombinant coat protein and ssRNA employed, as well as the temperature of the reaction, and can be readily determined by the skilled worker. Typically time periods of at least about 60 minutes are employed. Assembly of the coat protein into VLPs can be monitored if required by standard techniques, such as dynamic light scattering or electron microscopy.

After the assembly reaction has been allowed to proceed for an appropriate length of time, the VLPs are subjected to a "blunting" step to remove RNA protruding from the particles. The blunting reaction is achieved using a nuclease capable of cutting RNA. Various nucleases are commercially available and conditions for their use are known in the art.

The VLPs once assembled can be purified from other reaction components by standard techniques, such as dialysis, diafiltration or chromatography.

The VLP preparation can optionally be concentrated (or enriched) by, for example, ultracentrifugation or diafiltration, either before or after the purification step(s). VLPs can be visualized using standard techniques, such as electron microscopy, if desired.

Characteristics of Recombinant VLPs

PapMV VLPs when assembled, each comprise a long helical array of coat protein subunits. The wild-type virus comprises over 1200 coat protein subunits and is about 500 nm in length. Recombinant PapMV VLPs prepared by the process according to the present invention may be of similar size, or may be shorter or longer than the wild-type virus. In certain embodiments of the present invention, recombinant PapMV VLPs comprise at least 40 coat protein subunits. In some embodiments, recombinant PapMV VLPs may comprise between about 40 and about 1600 coat protein subunits, however, VLPs comprising a greater number of coat proteins are also contemplated. Recombinant PapMV VLPs are typically about 10-20 nm wide and between about 40 nm and several thousand nm in length. In certain embodiments, preparations of the recombinant PapMV VLPs have an average length of between about 40 nm and about 600 nm, for example, between about 40 nm and about 500 nm, between about 40 nm and between about 400 nm, or between about 40 nm and about 300 nm.

The recombinant PapMV VLPs are stable and can be stored easily at room temperature. When stored at lower temperatures, for example, between about 2° C. and about 8° C., recombinant PapMV VLPs are stable for at least several months and up to several years.

Methods and Uses of the Recombinant VLPs

The present invention provides for a number of applications and uses of the recombinant PapMV VLPs. For example, the recombinant PapMV VLPs may be used as adjuvants to enhance the immunogenicity of antigens, or when fused to antigen(s), as vaccines. In certain embodiments, the PapMV VLPs may be used alone to stimulate the innate immune response in a subject, and thereby treat or prevent infection. The use of the recombinant PapMV VLPs for the preparation of medicaments, including vaccines, and/or pharmaceutical compositions is thus also within the scope of the present invention.

Examples of diseases and disorders that may be treated or prevented with vaccines in accordance with the present invention include, for example, infectious diseases (such as viral or bacterial diseases), allergic reactions, immune diseases and cancer.

Antigens suitable for use with the PapMV VLPs, or fusion to the recombinant PapMV coat protein, may be antigens associated with various diseases or disorders. A wide variety of such antigens are known in the art. Appropriate antigens can be readily selected by one skilled in the art based on, for example, the desired end use of the VLPs, such as the disease or disorder against which it is to be directed and/or the animal to which it is to be administered.

For example, the antigen can be derived from an agent capable of causing a disease or disorder in an animal, such as a cancer, infectious disease, allergic reaction, or autoimmune disease, or it can be an antigen suitable for use to induce an immune response against drugs, hormones or a toxin-associated disease or disorder. The antigen may be derived from a pathogen known in the art, such as, for example, a bacterium, virus, protozoan, fungus, parasite, or infectious particle, such as a prion, or it may be a tumour-associated antigen, a self-antigen or an allergen.

In certain embodiments, the PapMV VLPs are used in combination with a commercially available vaccine in order to enhance the efficacy of the vaccine.

Useful antigens include viral antigens, for example, derived from members of the families Adenoviradae; Arenaviridae (for example, Ippy virus and Lassa virus); Birnaviridae; Bunyaviridae; Caliciviridae; Coronaviridae; Filoviridae; Flaviviridae (for example, yellow fever virus, dengue fever virus and hepatitis C virus); Hepadnaviradae (for example, hepatitis B virus); Herpesviradae (for example, human herpes simplex virus 1); Orthomyxoviridae (for example, influenza virus A, B and C); Paramyxoviridae (for example, mumps virus, measles virus and respiratory syncytial virus); Picornaviridae (for example, poliovirus and hepatitis A virus); Poxyiridae; Reoviridae; Retroviradae (for example, BLV-HTLV retrovirus, HIV-1, HIV-2, bovine immunodeficiency virus and feline immunodeficiency virus); Rhabodoviridae (for example, rabies virus), and Togaviridae (for example, rubella virus). In one embodiment, the recombinant PapMV CP comprises one or more antigenic peptides derived from a major viral pathogen such as the dengue virus, various hepatitis viruses, human immunodeficiency virus (HIV), various influenza viruses, West Nile virus, respiratory syncytial virus, influenza virus, rabies virus, human papilloma virus (HPV), Epstein Barr virus (EBV), polyoma virus, or SARS coronavirus.

Useful antigens may also be derived from unconventional viruses or virus-like agents such as the causative agents of kuru, Creutzfeldt-Jakob disease (CJD), scrapie, transmissible mink encephalopathy, and chronic wasting diseases, or from proteinaceous infectious particles such as prions that are associated with mad cow disease, as are known in the art.

Useful bacterial antigens include, for example, superficial bacterial antigenic components, proteinacious capsular antigens, or flagellar components and may be obtained or derived from known causative agents responsible for diseases such as diptheria, pertussis, tetanus, tuberculosis, bacterial pneumonia, fungal pneumonia, cholera, typhoid, plague, shigellosis, salmonellosis, Legionnaire's disease, lyme disease, leprosy, malaria, hookworm, onchocerciasis, schistosomiasis, trypamasomialsis, lehmaniasis, giardia, amoebiasis, filariasis, borrelia, and trichinosis.

Useful tumour-associated antigens include, for example, Her2 (breast cancer); GD2 (neuroblastoma); EGF-R (malignant glioblastoma); CEA (medullary thyroid cancer); CD52 (leukemia); human melanoma protein gp100; human melanoma protein melan-A/MART-1; NA17-A nt protein; p53 protein; various MAGEs (melanoma associated antigen E), including MAGE 1, MAGE 2, MAGE 3 (HLA-A1 peptide) and MAGE 4; various tyrosinases (HLA-A2 peptide); mutant ras; p97 melanoma antigen; Ras peptide and p53 peptide associated with advanced cancers; the HPV 16/18 and E6/E7 antigens associated with cervical cancers; MUC1-KLH antigen associated with breast carcinoma; CEA (carcinoembryonic antigen) associated with colorectal cancer, DKK-1 (Dickkopf-1 protein) associated with lung cancer and the PSA antigen associated with prostate cancer.

Useful allergens include, for example, allergens from pollens, animal dander, grasses, moulds, dusts, antibiotics, stinging insect venoms, as well as a variety of environmental, drug and food allergens. Common tree allergens include pollens from cottonwood, popular, ash, birch, maple, oak, elm, hickory, and pecan trees. Common plant allergens include those from rye, ragweed, English plantain, sorreldock and pigweed, and plant contact allergens include those from poison oak, poison ivy and nettles. Common grass allergens include Timothy, Johnson, Bermuda, fescue and bluegrass allergens. Common allergens can also be obtained from moulds or fungi such as *Alternaria, Fusarium, Hormodendrum, Aspergillus, Micropolyspora, Mucor* and theormophilic actinomycetes. Epidermal allergens can be obtained from house or organic dusts (typically fungal in origin), from insects such as house mites (demialphagoides pterosinyssis), or from animal sources such as feathers, and cat and dog dander. Common food allergens include milk and cheese (diary), egg, wheat, nut (for example, peanut), seafood (for example, shellfish), pea, bean and gluten allergens. Common insect allergens include bee, hornet, wasp and ant venom, and cockroach calyx allergens.

In certain embodiments, the present invention provides for the use of the PapMV VLPs to stimulate the innate immune response in a subject. The subject may be a human or a non-human animal. The PapMV VLPs may be used, for example, in the treatment or prevention of infection, including chronic infection, as described herein (see also, International Patent Application No. PT/CA2012/050278 "Papaya Mosaic Virus Compositions and Uses Thereof for Stimulation of the Innate Immune Response," Filed May 1, 2012, herein incorporated by reference in its entirety).

In certain embodiments, the present invention provides for the use of PapMV VLPs to stimulate the innate immune response and thereby protect a subject from potential infection by a pathogen. In accordance with certain embodiments of the invention, the PapMV VLPs are administered via intranasal or pulmonary routes and elicit a protective effect within the mucosa and/or in the respiratory system. In various embodiments if the invention, the pathogen is one or more of a viral pathogen, a bacterial pathogen or a fungal pathogen.

In some embodiments, the PapMV VLPs are administered to a subject as a preventative or pre-emptive measure to protect against infection with a pathogen. Such an approach is useful, for example, in immunocompromised patients (such as patients with AIDS, patients under chemotherapy or patients taking immunosuppressive drugs), in pandemic or epidemic situations to provide initial protection to the population prior to development/distribution of an appropriate vaccine, to protect workers such as rescue workers, doctors and nurses entering areas of potential infection, and in situations where there is a threat of, or an incidence of, a bioterrorism attack.

In certain embodiments, PapMV VLPs may be administered to non-human animals in competition settings as a pre-emptive measure to protect against infection, for example, horse races, dog shows, cat shows and the like. Administration of PapMV VLPs to livestock in epidemic/pandemic situations is also contemplated in certain embodiments.

In certain embodiments, PapMV VLPs may be used to treat an infection, for example, an infection with a viral pathogen, a bacterial pathogen or a fungal pathogen, including chronic infections, such as HIV and HCV. In some embodiments, PapMV compositions may be used to treat an infection at a mucosal surface, for example, in the lungs, intestines or genitourinary system.

In certain embodiments, PapMV VLPs can be administered via pulmonary routes to lung cancer patients to stimulate the anti-tumour activity of the innate immune response in the lungs.

In certain embodiments, the PapMV VLPs are used as a mucosal adjuvant to stimulate the mucosal immune response and thus improve protection to infections and diseases of the intestine, genitourinary tract, and other mucosal surfaces including the lung.

Pharmaceutical Compositions

In certain embodiments, the present invention provides for pharmaceutical compositions comprising an effective amount of the PapMV VLPs and one or more pharmaceutically acceptable carriers, diluents and/or excipients. If desired, other active ingredients may be included in the compositions, for example, additional immune stimulating compounds, standard therapeutics, vaccines or the like.

The pharmaceutical compositions can be formulated for administration by a variety of routes. For example, the compositions can be formulated for oral, topical, rectal, nasal or parenteral administration or for administration by inhalation or spray. The term parenteral as used herein includes subcutaneous injections, intravenous, intramuscular, intrathecal, intrasternal injection or infusion techniques. Intranasal administration to the subject includes administering the composition to the mucous membranes of the nasal passage or nasal cavity of the subject.

In some embodiments, the pharmaceutical compositions are formulated for mucosal administration. Mucosal administration may include, for example, oral, intranasal, aerosol, rectal or vaginal administration. The preparations for mucosal administration include transdermal devices, aerosols, creams, lotions or powders pending on the mucosal site. In certain embodiments, the pharmaceutical compositions are formulated for intranasal or pulmonary administration. In some embodiments, the pharmaceutical compositions are formulated for rectal or vaginal administration.

Compositions formulated as aqueous suspensions may contain the PapMV VLPs in admixture with one or more suitable excipients, for example, with suspending agents, such as sodium carboxymethylcellulose, methyl cellulose, hydropropylmethylcellulose, sodium alginate, polyvinylpyrrolidone, hydroxypropyl-β-cyclodextrin, gum tragacanth and gum acacia; dispersing or wetting agents such as a naturally-occurring phosphatide, for example, lecithin, or condensation products of an alkylene oxide with fatty acids, for example, polyoxyethyene stearate, or condensation products of ethylene oxide with long chain aliphatic alcohols, for example, hepta-decaethyleneoxycetanol, or condensation products of ethylene oxide with partial esters derived from fatty acids and a hexitol for example, polyoxyethylene sorbitol monooleate, or condensation products of ethylene oxide with partial esters derived from fatty acids and hexitol anhydrides, for example, polyethylene sorbitan monooleate. The aqueous suspensions may also contain one or more preservatives, for example ethyl, or n-propyl p-hydroxybenzoate, one or more colouring agents, one or more flavouring agents or one or more sweetening agents, such as sucrose or saccharin.

In certain embodiments, the pharmaceutical compositions may be formulated as oily suspensions by suspending the PapMV VLPs in a vegetable oil, for example, arachis oil, olive oil, sesame oil or coconut oil, or in a mineral oil such as liquid paraffin. The oily suspensions may contain a thickening agent, for example, beeswax, hard paraffin or cetyl alcohol. These compositions can be preserved by the addition of an anti-oxidant such as ascorbic acid.

In certain embodiments, the pharmaceutical compositions may be formulated as a dispersible powder or granules, which can subsequently be used to prepare an aqueous suspension by the addition of water. Such dispersible powders or granules provide the PapMV VLPs in admixture with one or more dispersing or wetting agents, suspending agents and/or preservatives. Suitable dispersing or wetting agents and suspending agents are exemplified by those already mentioned above. Additional excipients, for example, colouring agents, can also be included in these compositions.

Pharmaceutical compositions of the invention may also be formulated as oil-in-water emulsions in some embodiments. The oil phase can be a vegetable oil, for example, olive oil or arachis oil, or a mineral oil, for example, liquid paraffin, or it may be a mixture of these oils. Suitable emulsifying agents for inclusion in these compositions include naturally-occurring gums, for example, gum acacia or gum tragacanth; naturally-occurring phosphatides, for example, soy bean, lecithin; or esters or partial esters derived from fatty acids and hexitol, anhydrides, for example, sorbitan monoleate, and condensation products of the said partial esters with ethylene oxide, for example, polyoxyethylene sorbitan monoleate.

In certain embodiments, the pharmaceutical compositions may be formulated as a sterile injectable aqueous or oleaginous suspension according to methods known in the art and using suitable one or more dispersing or wetting agents and/or suspending agents, such as those mentioned above. The sterile injectable preparation can be a sterile injectable solution or suspension in a non-toxic parentally acceptable diluent or solvent, for example, as a solution in 1,3-butanediol. Acceptable vehicles and solvents that can be employed include, but are not limited to, water, Ringer's solution, lactated Ringer's solution and isotonic sodium chloride solution. Other examples include, sterile, fixed oils, which are conventionally employed as a solvent or suspending medium, and a variety of bland fixed oils including, for example, synthetic mono- or diglycerides. Fatty acids such as oleic acid can also be used in the preparation of injectables.

Optionally the pharmaceutical compositions may contain preservatives such as antimicrobial agents, anti-oxidants, chelating agents, and inert gases, and/or stabilizers such as a carbohydrate (e.g. sorbitol, mannitol, starch, sucrose, glucose, or dextran), a protein (e.g. albumin or casein), or a protein-containing agent (e.g. bovine serum or skimmed milk) together with a suitable buffer (e.g. phosphate buffer). The pH and exact concentration of the various components of the composition may be adjusted according to well-known parameters.

Sterile compositions can be prepared for example by incorporating the PapMV VLPs in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile compositions, some exemplary methods of preparation are vacuum-drying and freeze-drying techniques which yield a powder of the active ingredient plus any additional desired ingredient from a previously sterile-filtered solution thereof.

Contemplated for use in certain embodiments of the invention are various mechanical devices designed for pulmonary or intranasal delivery of therapeutic products, including but not limited to, nebulizers, metered dose inhalers, powder inhalers and nasal spray devices, all of which are familiar to those skilled in the art.

Metered dose inhalers typically use a propellant gas and require actuation during inspiration. Dry powder inhalers use breath-actuation of a mixed powder. Nebulizers produce aerosols from solutions, while metered dose inhalers, dry powder inhalers, and the like generate small particle aerosols.

Some specific examples of commercially available mechanical devices include the ULTRAVENT® nebulizer (Mallinckrodt, Inc., St. Louis, Mo.), the ACORN II® nebulizer (Marquest Medical Products, Englewood, Colo.), the MISTY-NEB® nebulizer (Allegiance, McGraw Park, Ill.), the AEROECLIPSE® nebulizer (Trudell Medical International, Canada), the Accuspray™ nasal spray device (Becton Dickinson), the Mucosal Atomization Device (MAD300) (Wolfe Tory Medical), the OptiNose device (OptiNose, Oslo, Norway), the Nektar DPI system (Nektar Therapeutics, Inc., San Carlos, Calif.), the AERx pulmonary drug delivery system (Aradigm Corporation, Hayward, Calif.), the Spiros® device (Dura Pharmaceuticals), and the Respimat® device (Boehringer Ingelheim).

All such devices require the use of formulations suitable for the dispensing of the PapMV VLPs. Typically, each formulation is specific to the type of device employed and may involve the use of an appropriate propellant material, in addition to the usual diluents, adjuvants and/or carriers useful in therapy as would be understood by a worker skilled in the art. Also, the use of liposomes, microcapsules or microspheres, inclusion complexes, or other types of carriers is contemplated.

In certain embodiments of the invention, the pharmaceutical compositions are administered intranasally and the compositions are therefore formulated as nasal gels, creams, pastes or ointments that provide a more sustained contact with the nasal mucosal surfaces. These formulations typically have a viscosity between about 10 and about 250,000 centipoise (cps), for example, between about 2500 about 100,000 cps, or between about 5,000 and 50,000 cps. Such formulations may be based upon, for example, alkylcelluloses and/or other biocompatible carriers of high viscosity well known to the art. A non-limiting example of an alkylcellulose is methylcellulose, which can be included in a suitable concentration, for example, between about 5 mg and about 1000 mg per 100 ml of carrier, or between about 25 mg and about mg per 100 ml of carrier. In certain embodiments, the carrier containing the PapMV VLPs may be soaked into a suitable substrate, for example a fabric material, such as gauze, that can be applied to the nasal mucosal surfaces to allow for penetration of the PapMV VLPs into the mucosa.

In certain embodiments, gel formulations may also include a permeation enhancer (penetration enhancer). Permeation enhancers include, but are not limited to, sulfoxides such as dimethylsulfoxide and decylmethylsulfoxide; surfactants such as sodium laurate, sodium lauryl sulfate, cetyltrimethylammonium bromide, benzalkonium chloride, poloxamer (231, 182, 184), Tween (20, 40, 60, 80) and lecithin; the 1-substituted azacycloheptan-2-ones, particularly 1-n-dodecylcyclazacycloheptan-2-one; fatty alcohols such as lauryl alcohol, myristyl alcohol, oleyl alcohol and the like; fatty acids such as lauric acid, oleic acid and valeric acid; fatty acid esters such as isopropyl myristate, isopropyl palmitate, methylpropionate, and ethyl oleate; polyols and esters thereof such as propylene glycol, ethylene glycol, glycerol, butanediol, polyethylene glycol, and polyethylene glycol monolaurate, amides and other nitrogenous compounds such as urea, dimethylacetamide (DMA), dimethylformamide (DMF), 2-pyrrolidone, 1-methyl-2-pyrrolidone, ethanolamine, diethanolamine and triethanolamine, terpenes; alkanones; and organic acids, particularly salicylic acid and salicylates, citric acid and succinic acid. The permeation enhancer may be present in an amount from about 0.1% to about 30% w/w. The gel compositions may also include a buffering agent, for example, carbonate buffers, citrate buffers, phosphate buffers, acetate buffers, hydrochloric acid, lactic acid, tartaric acid, inorganic and organic bases. The buffering agent may be present in a concentration of about 1 to about 10 weight percent, for example, about 2 to about 5 weight percent, depending on the type of buffering agent(s) used, as known by the one skilled in the art. Concentrations of the buffering agent(s) may vary, however, and in some embodiments the buffering agent may replace up to 100% of the water amount within the composition.

In certain embodiments of the invention, the pharmaceutical compositions are formulated for rectal or vaginal administration and may be presented as a suppository, which may be prepared by mixing the active ingredient(s) with one or more suitable non-irritating excipients or carriers. Non-limiting examples of excipients or carriers include cocoa butter, polyethylene glycol, a suppository wax or salicylate and which is solid at room temperature, but liquid at body temperature and, therefore, will melt in the rectum or vaginal cavity and release the active ingredient(s). Formulations of the present invention which are suitable for vaginal administration also include pessaries, tampons, creams, gels, pastes, foams or spray formulations containing such carriers as are known in the art to be appropriate.

Also encompassed by the present invention are pharmaceutical compositions comprising the PapMV VLPs in combination with commercially available vaccines.

Other pharmaceutical compositions and methods of preparing pharmaceutical compositions are known in the art and are described, for example, in "*Remington: The Science and Practice of Pharmacy*" (formerly "*Remington Pharmaceutical Sciences*"); Gennaro, A., Lippincott, Williams & Wilkins, Philadelphia, Pa. (2000).

Kits

The present invention additionally provides for kits comprising components for use in the in vitro process to prepare VLPs, as well as pharmaceutical kits comprising PapMV VLPs.

Kits for the Preparation of Recombinant VLPs

Certain embodiments of the invention provide for kits comprising components for use in the in vitro process described herein. For example, the kits may comprise a plasmid encoding the PapMV coat protein and/or a plasmid encoding the ssRNA template, or the kit may comprise purified recombinant PapMV coat protein and/or purified ssRNA template.

The kit may optionally further comprise one or more other components used in the preparation of recombinant PapMV coat protein, or ssRNA, or in the assembly reaction, or in purification of the recombinant VLPs, such as culture media, polymerases, restriction enzymes, buffers, inducers, nucleases, and the like.

Individual components of the kit would be packaged in separate containers and some may, in certain embodiments, be provided in dried or lyophilised form. The kit may further comprise instructions for use.

Pharmaceutical Kits

Certain embodiments of the invention provide for pharmaceutical kits comprising recombinant PapMV VLPs for use as an adjuvant, immunostimulator or vaccine. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale. The kit may optionally contain instructions or directions outlining the method of use or administration regimen for the recombinant PapMV VLPs.

When the kit comprises recombinant PapMV VLPs for use as an adjuvant, the kit may further comprise one or more antigens for use in combination with the recombinant PapMV VLPs. In certain embodiments, the antigens may be in the form of a vaccine, such as a commercially available vaccine.

When one or more components of the kit are provided as solutions, for example an aqueous solution, or a sterile aqueous solution, the container means may itself be an inhalant, syringe, pipette, eye dropper, or other such like apparatus, from which the solution may be administered to a subject or applied to and mixed with the other components of the kit.

The components of the kit may also be provided in dried or lyophilised form and the kit can additionally contain a suitable solvent for reconstitution of the lyophilised components. Irrespective of the number or type of containers, the kits of the invention also may comprise an instrument for assisting with the administration of the composition to a patient. Such an instrument may be an inhalant, nasal spray device, nebulizer, syringe, pipette, forceps, measured spoon, eye dropper or similar medically approved delivery vehicle.

To gain a better understanding of the invention described herein, the following examples are set forth. It will be understood that these examples are intended to describe illustrative embodiments of the invention and are not intended to limit the scope of the invention in any way.

EXAMPLES

Example 1: Process for Preparing PapMV VLPs Comprising ssRNA: Overview

Figure 6:
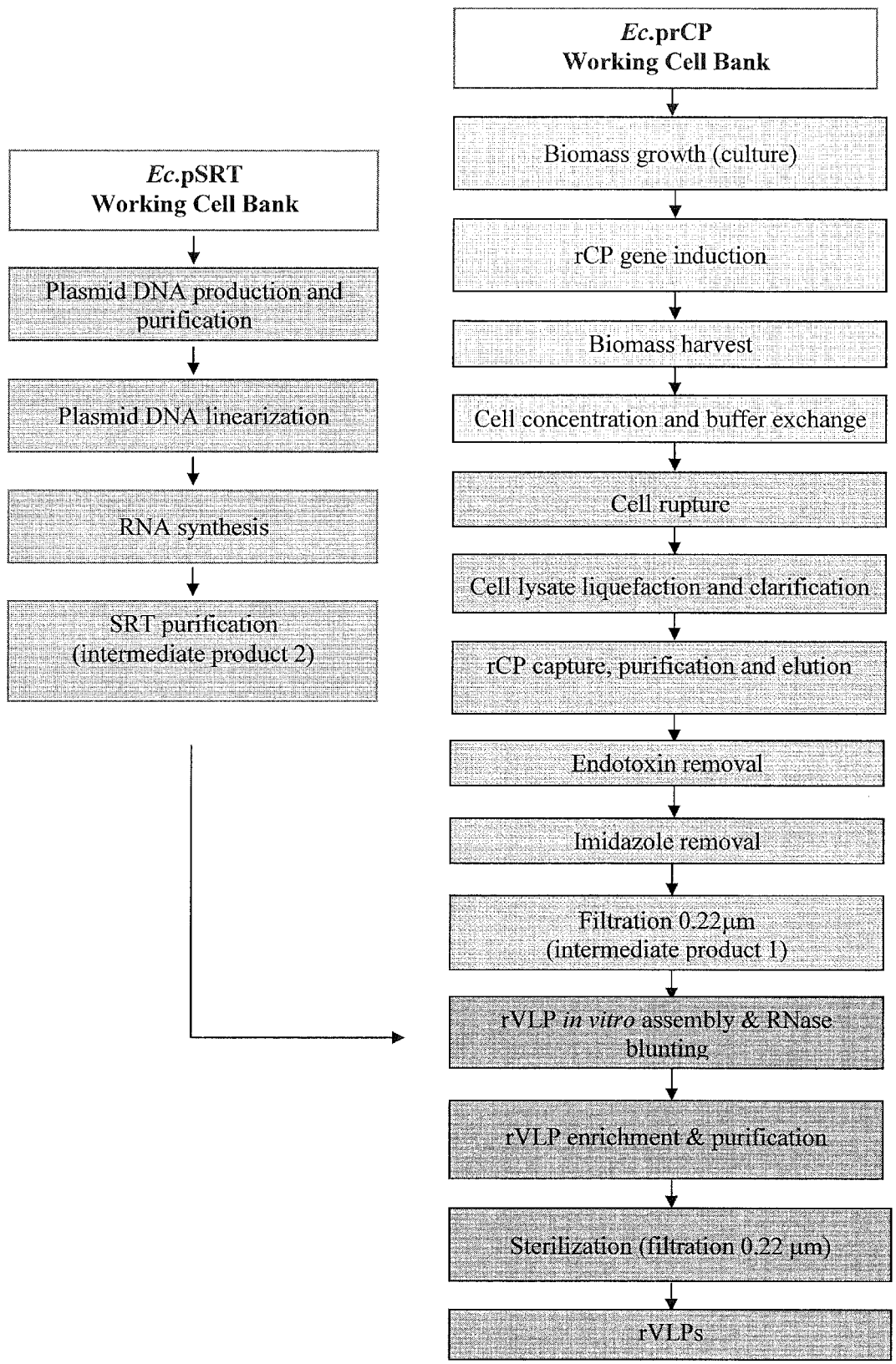
FIG. 6 presents a flow chart outlining the steps for the preparation of in vitro assembled PapMV VLPs containing ssRNA in accordance with one embodiment of the invention (abbreviations as for FIG. 4; Ec.prCP=E. coli containing plasmid encoding rCP; Ec.pSRT=E. coli containing plasmid encoding SRT).

The process described in this Example is summarized in the flow chart presented in FIG. 6. The recombinant VLPs (rVLPs) produced by this process were rod shaped nanoparticles 15 nm wide, and 50 to thousands nm-long. Typical preparations of rVLPs had a mean size of 15×100 nm. It is possible to increase the size of rVLP after the assembly reaction by macromolecular polymerization of several rVLPs such that the final rVLPs are up to thousands of nm in length.

1. Production of Intermediate Product 1 (Recombinant Coat Protein (rCP))

rCP was produced in a host cell transformed with plasmid DNA containing the rCP gene under the control of an inducible promoter. Transformed host cells were grown in culture medium. Protein expression was triggered by addition of a biochemical inducer to the culture medium. At the end of the induction period, cells were harvested, suspended in lysis buffer and ruptured. Cell lysate was clarified by removal of genomic DNA and membranes. rCP was captured by ion-matrix affinity resin and then purified from endotoxins and small aMW molecules. The final intermediate product 1 was a protein solution that was sterilized by filtration. Sterile product stored at 2-8° C. is stable for several years.

1.1 Host-Vector Combination

Host: *E. coli* strains DH5-α, BL21 and BD792, and the yeast *Pichia pastoris* GS 115 strain have been used.

Vector: $pET_{24}$ and $pQE_{80}$ plasmid DNA have been used with prokaryotic cells, and pPICZα plasmid DNA has been used with yeast cells.

1.2 Biomass Production (Culture)

Prokaryotic biomass has been produced in both flask and bioreactor.

Yeast biomass has been produced in flask only.

Several type of culture media were used to grow biomass (defined medium using glycerol or glucose as the only source of carbon, as well as more common media using yeast extracts and tryptone as source of carbon).

1.3 Induction of the Recombinant Gene Expression

Induction of recombinant gene expression has been performed with various amounts of IPTG (0.3 to 2 mM) and various periods of incubation (3 to 24 h) at 20° C., 22° C., 25° C., 32° C. or 37° C. Optimal induction was obtained with 0.7-1 mM IPTG for 6-9 h at 22-25° C.

Auto-induction medium with specific glucose/glycerol/lactose ratio has been performed at 32° C.

1.4 Biomass Harvest, Concentration and Buffer Exchange

Cells can be concentrated by centrifugation. The wet biomass can be stored frozen below −60° C. for several months. Before cell rupture, cells were suspended in hypertonic neutral lysis buffer (e.g. 10 mM Tris pH 8.0, 500 mM NaCl).

Cell concentration and buffer exchange can also be conducted by tangential flow filtration. A hypertonic solution should be used during buffer exchange to prevent in vivo assembly of rCP onto bacterial RNA. Cell suspension can be stored frozen below −60° C. for several months, or at 2-8° C. for 72 h.

1.5 Cell Rupture

Cells were ruptured mechanically using a French press, homogenizer or sonicator.

1.6 Liquefaction and Clarification of the Cell Lysate

DNase treatment was used to fragment bacterial genomic DNA. Various types of DNase have been used, including Benzonase™.

Large cell fragments and membranes were removed from the cell lysate by centrifugation or tangential flow filtration (300 kDa to 0.45 μm molecular weigh cut-off (MWCO) membranes).

Low molecular weight contaminants can be removed by tangential flow filtration (0 to 30 kDa MWCO membranes).

1.7 Ion Matrix Affinity Chromatography (IMAC) Capture and Purification

The rCP harbored a 6×His-tag and was captured and purified by ion matrix affinity chromatography. A low concentration of imidazole was used to decrease background during IMAC-loading of the clarified cell extract. rCP can be eluted from IMAC column with pH gradient or with imidazole.

1.8 Endotoxin Removal

Contaminating endotoxins present in rCP solution can be removed thanks to anion exchange chromatography/filtration.

1.9 Imidazole Removal

Contaminating imidazole present in rCP solution can be removed by dialysis or tangential flow filtration (5 to 30 kDa MWCO membranes).

2. Production of Intermediate Product 2 (ssRNA Template (SRT))

The poly-mutated genome of PapMV was inserted into a plasmid DNA. The recombinant plasmid was used to transform bacteria. Transformed bacteria were grown in culture medium and the plasmid DNA was captured and purified from the cell culture by standard molecular biology techniques.

Plasmid DNA was linearized by DNA restriction enzyme digest at the location where the synthetic RNA transcript will end.

Transcription of SRT was conducted using RNA polymerase. The expression vector was designed such that transcripts originating from the RNA polymerase promoter were released from the DNA template at the DNA point of cleavage. SRT were produced in vitro and purified to remove DNA, protein and free nucleotides. The final intermediate product 2 was a RNA solution that was sterilized by filtration. Sterile product stored below −60° C. is stable for several years.

2.1 Host-Vector Combination

Various bacterial hosts that allow the replication of plasmid DNA may be used, together with various standard expression vectors that can replicate in the selected bacterial host. The expression vector should harbor a prokaryotic RNA polymerase promoter for the transcription of SRT.

2.2 Plasmid DNA Production and Purification

Various plasmid DNA extraction and purification methods known in the art can be used to prepare and purify the plasmid DNA.

2.3 Plasmid DNA Linearization

The restriction endonuclease for linearization of the plasmid DNA was selected to satisfy the following conditions: (i) the restriction enzyme must not cleave the DNA sequences between the RNA polymerase promoter and the last nucleotide to be present in the SRT; and (ii) the restriction enzyme must cleave the DNA sequence immediately after the last nucleotide to be present in the SRT.

3.3 Synthesis of RNA Templates

The 5'-end of the SRT harbors the PapMV coat protein nucleation signal whereas other nucleotide sequences are derived from a polymutated version of the PapMV 5'-end genome. DNA sequences encoding exemplary ST sequences are provided in FIG. 7 [SEQ ID NOs: 5 and 6].

3.4 Purification of SRT

Full-length SRT can be purified from free ribonucleotides and deoxy-ribonucleotides by tangential flow filtration using MWCO membranes related to the size of the SRT. For example, a 1500 nt-long SRT was purified from free nucleotides using a 100 kDa MWCO membrane.

3. Production of rVLPs rVLPs were assembled in vitro by combining intermediate products 1 and 2. The assembly reaction was conducted in a neutral buffered solution. The newly assembled rVLPs were incubated with a low amount of RNase to remove any RNA protruding from the rVLPs; this manipulation improves the solubility of the rVLPs. The blunted-rVLPs were then purified from contaminants and free rCP (unassembled monomers). The final product was a rVLP liquid suspension that was sterilized by filtration. Sterile product stored at 2-8° C. is stable for several years.

3.1 Assembly Reaction

The assembly reaction process was conducted in a neutral aqueous buffer and does not require any other particular ion. It is based on the natural property of the rCP to assemble on ssRNA.

The assembly reaction can be conducted using various protein:RNA ratios. Optimal ratios with a 1500 nt-long SRT were between 15-30 mg of protein for 1 mg RNA.

The assembly reaction can be conducted at temperatures varying from 2 to 37° C., for a time period that is dependent on the concentrations of the intermediate products and on the temperature of the solution.

3.2 rVLP Blunting

Protruding RNA may be removed from the rVLPs using various types of nuclease under standard conditions.

3.3 rVLP Enrichment and Purification rVLP enrichment may be conducted by diafiltration using 100 kDa MWCO membranes.

Contaminating free nucleotides can be removed by diafiltration using 10-100 kDa MWCO membranes.

Contaminating nuclease can be removed by diafiltration using 100 kDa MWCO membranes.

Example 2: Exemplary Process for Preparing PapMV VLPs Comprising ssRNA

Production of rCP

DNA containing the rCP gene under the control of an inducible promoter. In brief, the PapMV CP harbouring a 6×His-tag was cloned into the pQE80 vector (QIAGEN) flanked by the restriction enzyme NcoI and BamHI and under the control of the T5 promoter. *E. coli* BD-792 were transformed with the plasmid and grown in standard culture medium. Protein expression was triggered by addition of IPTG (0.7-1 mM IPTG for 6-9 h at 22-25° C.) to the culture medium.

At the end of the induction period, cells were harvested, suspended in lysis buffer (10 mM Tris pH 8.0, 500 mM NaCl) and ruptured mechanically using a French press, homogenizer or sonicator. Cell lysate was clarified by removal of genomic DNA by standard DNase treatment and removal of large cell fragments and membranes by centrifugation or tangential flow filtration (300 kDa to 0.45 μm MWCO membranes). rCP was captured on an ion-matrix affinity resin and eluted with imidazole using standard procedures. The PapMC coat protein can be eluted with between 250 mM and 1M imidazole. Elution could also be achieved using a pH gradient. The rCP was subsequently purified from endotoxins by anion exchange chromatography/filtration and from small low MW molecules by tangential flow filtration (0 to 30 kDa MWCO membranes). Any contaminating imidazole present in the rCP solution was removed by dialysis or tangential flow filtration (5 to 30 kDa MWCO membranes). The final rCP protein solution was sterilized by filtration.

Production of SRT

The sequence of the DNA encoding the SRT is provided in FIG. 7A [SEQ ID NO:5]. The SRT is based on the genome of PapMV and harbours the PapMV coat protein nucleation signal at the 5'-end (boxed in FIG. 7A). The remaining nucleotide sequence is poly-mutated in that all ATG codons have been mutated for TAA stop codons. The first 16 nucleotides of the sequence (underlined in FIG. 7A) comprise the T7 transcription start site located within the pBluescript expression vector and are present within the RNA transcript. Pentameric repeats are underlined in FIG. 7A. The entire transcript is 1522 nucleotides in length. The longer SRT shown in FIG. 7B [SEQ ID NO:6] has also been successfully used for in vitro assembly.

DNA corresponding to the SRT was inserted into a DNA plasmid including a prokaryotic RNA polymerase promoter using standard procedures. The recombinant plasmid was used to transform *E. coli* cells and the transformed bacteria were subsequently grown in standard culture medium. The plasmid DNA was recovered and purified from the cell culture by standard techniques, then linearized by cleavage with the restriction enzyme MluI at the point in the DNA sequence immediately after the last nucleotide of the SRT sequence.

Transcription of SRT was conducted with T7 RNA polymerase using the RiboMAXT™ kit (Promega, USA) following the manufacturer's recommended protocol. The expression vector was designed such that transcripts originating from the RNA polymerase promoter were released from the DNA template at the DNA point of cleavage. The SRT was purified to remove DNA, protein and free nucleotides by tangential flow filtration using a 100 kDa MWCO membrane. The final RNA solution was sterilized by filtration.

Production of rVLPs rVLPs were assembled in vitro by combining the rCP and SRT. The assembly reaction was conducted in a neutral buffered solution (10 mM Tris-HCl pH 8). The assembly reaction was conducted using a protein:RNA ratio between 15-30 mg of protein for 1 mg RNA. The newly assembled rVLPs were incubated with a low amount of RNase (0.0001 µg RNAse per µg RNA) to remove any RNA protruding from the rVLPs. The blunted-rVLPs were then purified from contaminants and free rCP (unassembled monomeric rCP) by diafiltration using 10-100 kDa MWCO membranes. The final rVLP liquid suspension was sterilized by filtration.

Example 3: Induction of an Antiviral Response in Mice by Administration of PapMV VLPs Containing Synthetic ssRNA Polyinosinic-polycytidylic acid (poly I:C; dsRNA), a well known Toll-like receptor 3 (TLR-3) ligand, has been shown to be an inducer of the innate immune response in lungs through induction of the secretion of pro-inflammatory cytokines such as IL-6, CXCL10, JE, KC, mGCSF, CCL3, CCL5, and TNF (Stowell et al., 2009, Respir. Res., 10:43). TLR-7 is also known to activate the innate immune response through the binding of ligands such as ssRNA and R837 (a guanosine analogue).

In an attempt to increase the capacity of the PapMV VLPs to elicit an innate immune response and the development of an antiviral response, PapMV VLPs containing either poly I:C dsRNA or ssRNA were prepared by the method described in Example 2. PapMV coat protein was assembled in vitro with either poly I:C (dsRNA; InvivoGen, San Diego, Calif.) or ssRNA to produce VLPs comprising the respective RNAs. The ssRNA was prepared in vitro using the Promega T7 Ribomax Express large scale RNA production system (Promega, Madison, Wis.).

The assembled VLPs were examined by electron microscopy and observed to be similar to VLPs prepared by the method described in Tremblay et al. (2006, FEBS J., 273: 14-25) (see FIG. 8A: PapMV VLPs containing ssRNA and FIG. 8B: PapMV VLPs containing poly I:C).

The efficacy of the two types of VLPs in inducing protection against challenge with influenza virus was evaluated. Balb/C mice (10 per group) were treated with 60 µg of PapMV VLPs containing ssRNA ("PapMV VLP ssRNA"), PapMV VLPs containing poly I:C ("PapMV VLP poly I:C") or with an equivalent amount of RNA (i.e. 3 µg of either poly I:C or ssRNA). Control mice were treated with 60 µg of PapMV coat protein (CP) monomers (without RNA) or with control buffer (10 mM Tris-HCl pH 8). Mice were treated intranasally twice at 7 day intervals with 60 µg PapMV VLPs and challenged 3 days after the last treatment with 200 pfu of influenza virus strain WSN/33. The weight, symptoms and survival of the animals were measured once per day during the following 14 days. Animals that showed more that 20% weight loss were sacrificed.

Figure 9:
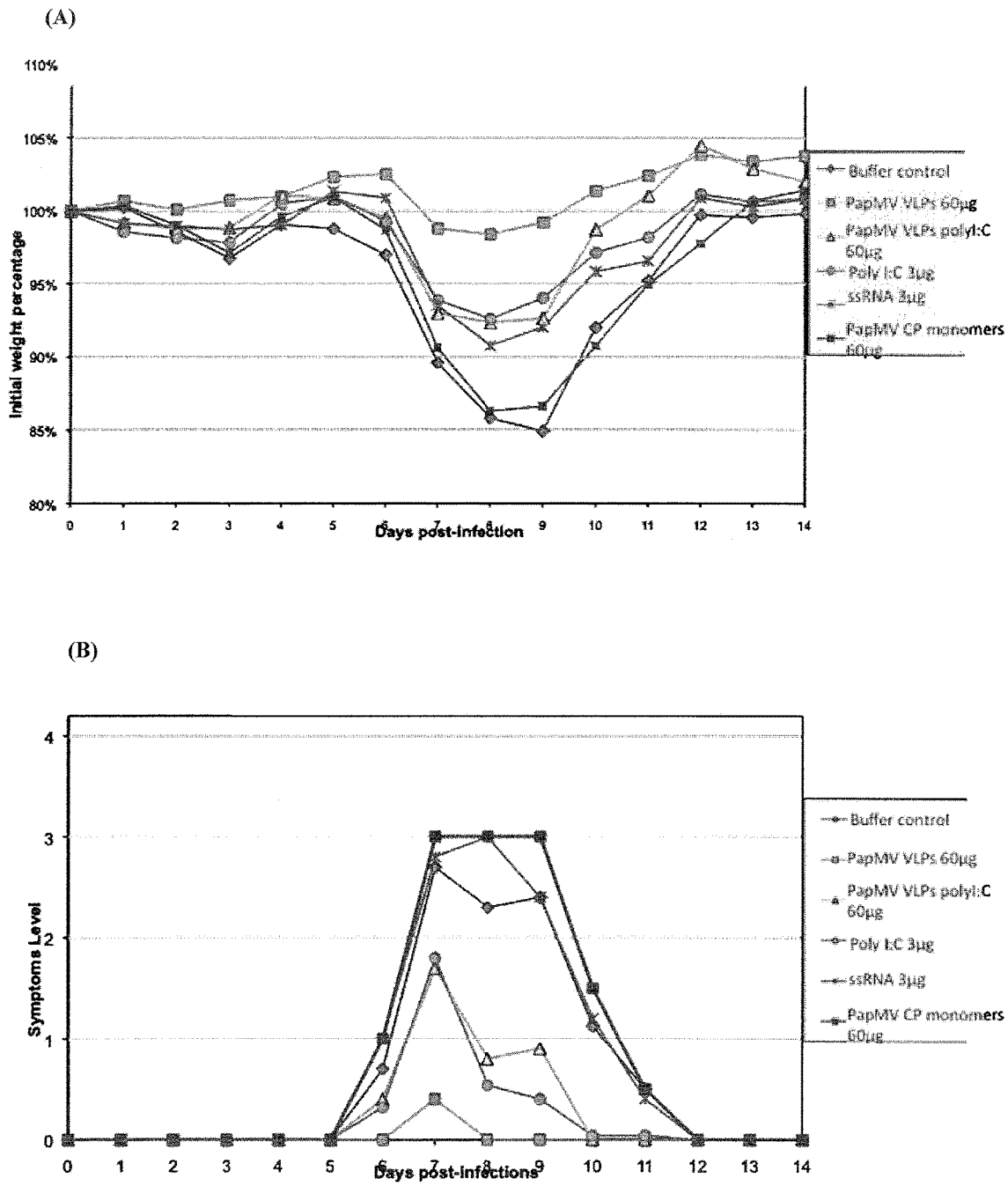
FIG. 9 presents results demonstrating that PapMV VLPs induce an anti-viral response that controls influenza infection, (A) depicts the weight loss of Balb/C mice (10 per group) treated intranasally with PapMV VLPs containing ssRNA, 60 μg PapMV VLPs containing poly I:C, 3 μg ssRNA, 3 μg poly I:C, 60 μg of PapMV CP monomers or control buffer (Tris HCl 10 mM pH 8) and challenged with 200 pfu of influenza virus strain WSN/33, (B) presents a summary of the symptoms developed in the mice during infection (Symptoms: 0, No symptoms. 1, Lightly spiked fur, slightly curved back. 2, Spiked fur, curved back. 3, Spiked fur, curved back, difficulty in moving and mild dehydration. 4, Spiked fur, curved back, difficulty in moving, severe dehydration, closed eyes and ocular secretion).

The results are shown in FIG. 9A-B. Mice treated with PapMV VLP ssRNA showed the best performance of the treated groups. Specifically, mice treated with PapMV VLP ssRNA did not lose any significant amount of weight (Figure A) and showed very few, if any, symptoms (FIG. 9B). The groups treated with either PapMV VLP poly I:C or poly I:C alone showed partial protection to the challenge with decreased weight losses (FIG. 9A) and symptoms (FIG. 9B) as compared to the control group. Treatment with the PapMV CP monomers did not provide any protection with the amount of weight loss (FIG. 9A) and symptoms (FIG. 9B) observed in mice treated with the monomers being similar to that observed in mice treated with the PBS control. Subsequent analysis of the PapMV VLP poly I:C suggested that these VLPs are not as stable as the PapMV VLP ssRNA, which may account for their poorer performance.

Example 4: Induction of Cytokines in Mice by Administration of PapMV VLPs #1

To elucidate the mechanisms induced by the PapMV VLP in the lungs, mice (5 per group) were inoculated intranasally twice at 7 day intervals with 60 µg PapMV VLPs containing ssRNA, 15 µg of PamCSK4 (a TLR-2 ligand and non-inducer of IFN type 1) (Cedarlane, Burlington, ON) or with the control buffer (10 mM Tris HCl pH8). Broncho-alveolar lavage (BAL) was performed 24 hours after the second treatment and screened for the presence of cytokines using Luminex technology (Milliplex Mouse cytokine premixed 32-plex immunoassay kit; Millipore).

Figure 10:
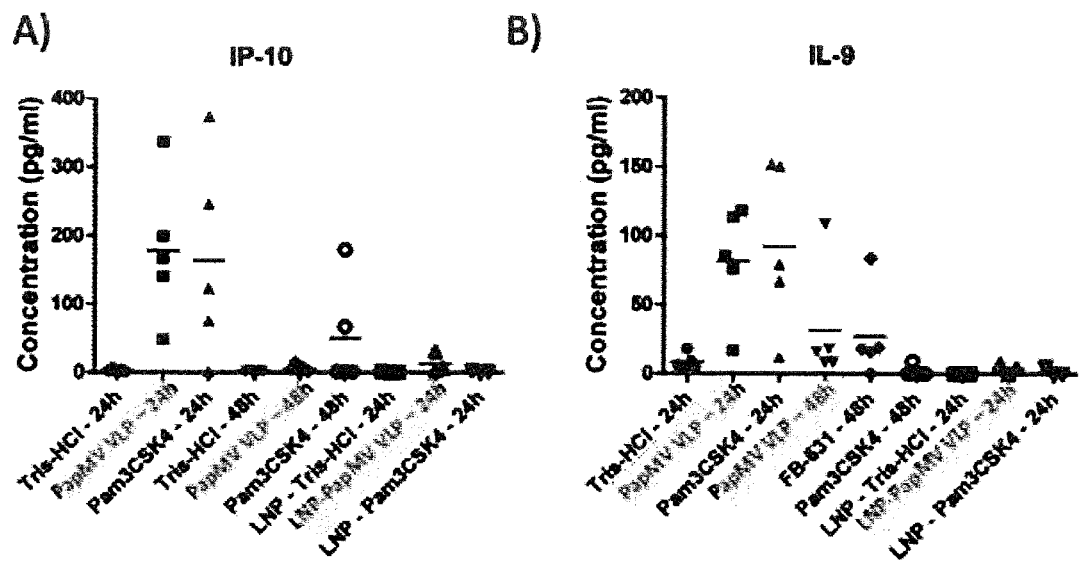
FIG. 10 presents graphs indicating the presence of IP-10 (A) and IL-9 (B) in bronchoalveolar lavage of Balb/C mice treated intranasally with PapMV VLPs (60 μg), Pam3CSK4 (15 μg) or control buffer (Tris HCl 10 mM pH 8). Each point corresponds to the level of cytokines detected in each mouse. Also shown is the amount of IP-10 or IL-9 present in nasopharyngeal lavage ("LNP") from the mice.

Two major cytokines, interleukin-9 (IL-9) and interferon-γ-induced protein 10 kDa (IP-10), were induced by treatment with PapMV VLPs or PamCSK4 (FIGS. 10A & B). IL-9 is a cytokine secreted by CD4+ T lymphocytes that promotes T-cell proliferation and inhibition of apoptosis. IP-10 appears as a result of the secretion of IFN-γ and plays an important role in recruitment of T-lymphocytes, dendritic cells, NK cells and macrophages at the site of stimulation. The induction of both cytokines by PamCSK4 (which is a known a TLR-2 ligand and pathogen associated molecular patterns (PAMP) molecule) and PapMV VLPs suggests that the VLPs may also be PAMPs.

Example 5: Induction of Cytokines in Mice by Administration of PapMV VLPs #2

A similar experiment to that described in Example 4 was conducted except that the BAL was performed 6 hours after treatment, and the treatments were either 1 or 2 inoculations at 7 day intervals. As before, 60 µg of PapMV VLPs containing ssRNA were used in the experiment. Luminex (32 cytokines detection kit) was used to screen for cytokine production early after treatment.

Figure 11:
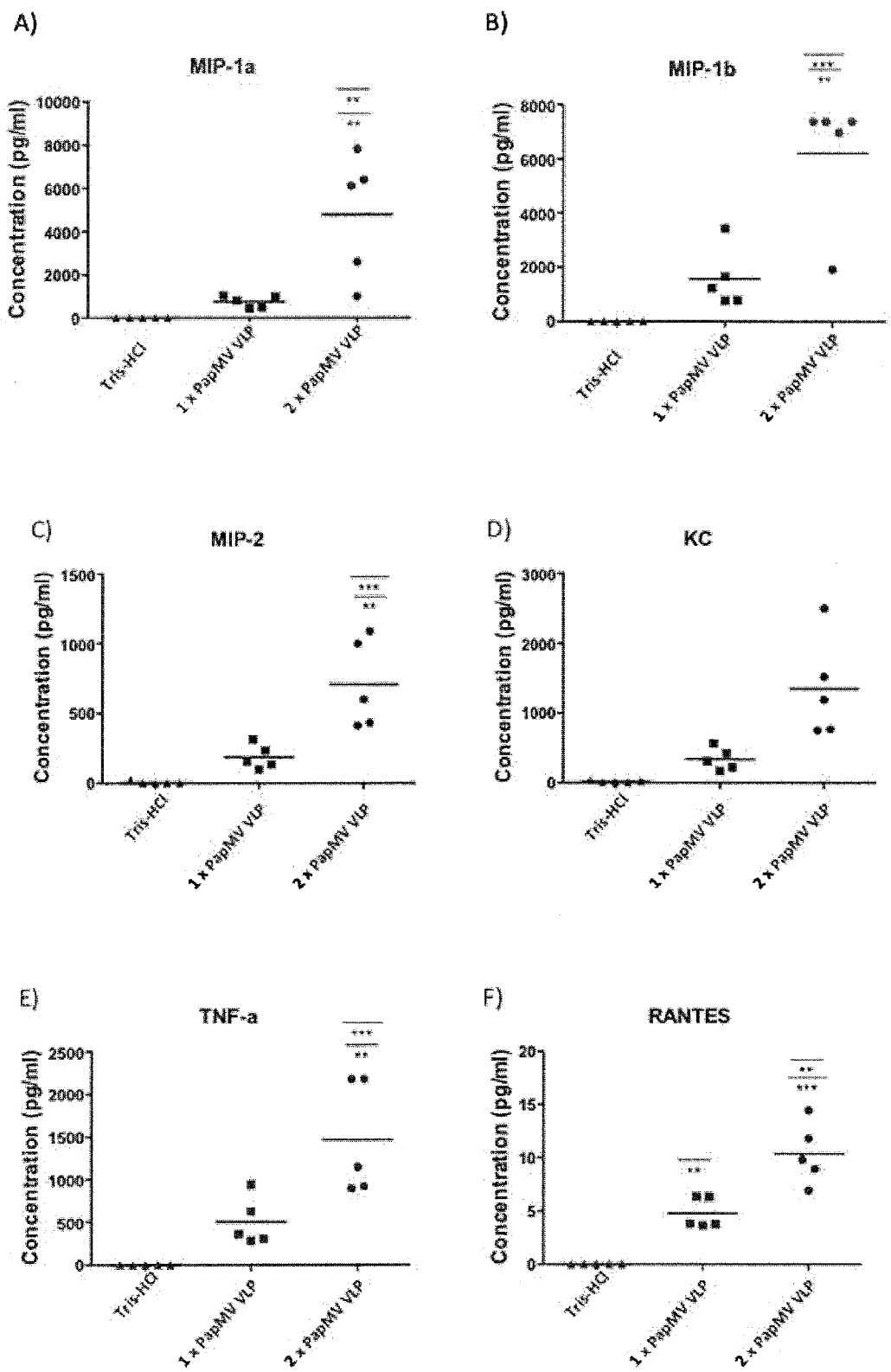
FIG. 11 presents graphs indicating the presence of (A) MIP-1α, (B) MIP-1β, (C) MIP-2, (D) KC, (E) TNF-α, (F) RANTES, (G) VEGF, (H) MCP-1, (I) IP-10, (J) IL-17, (K) IL-13, (L) IL-12 (p70), (M) IL-9, (N) IL-6, (O) IL-1α, (P) IL-1β, (Q) GM-CSF and (R) G-CSF in bronchoalveolar lavage of Balb/C mice treated intranasally with one or two treatments of PapMV VLPs (60 μg) or with control buffer (Tris HCl 10 mM pH 8). Each point corresponds to the level of cytokines detected in each mouse.

The results are shown in FIGS. 11A-R and demonstrate that 2 treatments with PapMV VLPs were more efficient than one treatment in inducing cytokines and chemokines in mice. In addition, a wider variety of cytokines and chemokines were detected at 6 hours after treatment than 24 hours after treatment (compare FIGS. 11 and 10).

MIP-1α, MIP-1β, MIP-2, mKC, TNF-α and MCP-1 were found to be very abundant (FIGS. 11A-E and H) in BAL from mice treated with PapMV VLPs. These cytokines and chemokines activate human granulocytes (neutrophils, eosinophils and basophils) which can lead to acute neutrophilic inflammation. They also induce the synthesis and release of other pro-inflammatory cytokines such as TNF-α, IL-6 and IL-1α/β from fibroblasts and macrophages (Maurer and von Stebut, 2004, The International Journal of Biochemistry & Cell Biology, 36: 1882-1886), which were also shown to be induced by PapMV VLPs (see FIGS. 8E, N, O and P respectively). MIP-1 proteins can also promote health by inducing inflammatory responses against infectious pathogens such as viruses, including influenza virus (Menten et al., 2002, Cytokine Growth Factor Reviews, 13: 455-481) and parasites (Aliberti et al., 2000, Natural Immunology, 1: 83-87), which is consistent with the results shown in the preceding Examples.

IL-6 was also observed to be secreted in response to administration of PapMV VLPs (FIG. 11N). Interestingly, IL-6 secretion was showed to be required for resistance to infection by the bacteria Pneumococcus pneumoniae (van der Poll et al., 1997, *J Infect Dis.*, 176 (2): 439-44).

IP-10 was strongly induced by the treatment with PapMV VLPs (FIG. 11I). IP-10 is a chemotactic chemokine that favours the recruitment of T cells at inflammatory sites and also favours proliferation and activation of natural killer cells (NK cells).

Interleukin 17 was also induced by the treatment with PapMV VLPs (FIG. 11J). IL-17 is a cytokine that acts by increasing chemokine production in various tissues to recruit monocytes and neutrophils to the site of inflammation, similar to Interferon gamma IL-17 is produced by T helper cells and is also a proinflammatory cytokine that responds to the invasion of the immune system by extracellular pathogens. IL-17 coordinates local tissue inflammation through the upregulation of proinflammatory cytokines and chemokines such as IL-6, granulocyte colony-stimulating factor, TNFα, IL-1, KC, MCP-1 and MIP-2 (Zepp et al., 2011, *Trends Immunol.* April 12. [Epub ahead of print]), which were also shown to be induced by PapMV VLP treatment.

PapMV VLP treatment (FIGS. 11Q & R) also induced G-CSF and GM-CSF, which are known to stimulate stem cells to produce granulocytes (neutrophils, eosinophils and basophils) and monocytes. Monocytes exit the circulation and migrate into tissue, whereupon they mature into macrophages. Thus, G-CSF and GM-CSF are part of the inflammatory cascade by which activation of a small number of macrophages can rapidly lead to an increase in their numbers, a process crucial for fighting infection (Metcalf, 2010, *Nature Reviews Cancer*, 20: 425-434).

The results described in this Examples and in Example 4 demonstrate that the treatment of mice with PapMV VLPs induces a strong and general inflammatory response as showed by the profile of cytokines and chemokines that are secreted by the immune cells. The levels of cytokines and chemokines were maximal at 6 hours after treatment and decreased significantly 24 hours after treatment. It is likely that the inflammatory cytokines and chemokines induced the migration of immune cells and granulocytes and thus are responsible for the observed anti-viral state of inoculated animals for more than 5 days. The induced cytokines can also lead to secretion of IFN type 1 that in turn is also known to provide an anti-influenza activity.

Example 6: Activation of TLR-7 by PapMV VLP ssRNA

C57BL/6, TLR7 knockout (KO), MYD88 KO and IRF5/7 KO mice (3-5 mice per group) were immunized intravenously (i.v.) with 100 μg PapMV VLP ssRNA or 100 μl PBS. Splenocytes were isolated 24 hours post-immunization and CD86 and CD69 expression in dendritic cells (DCs), CD8$^+$ T cells and B cells was analyzed. Cells were sorted by FACS and the level of CD86 and CD69 was evaluated by fluorescence intensity though the binding of a CD69 or CD86 specific antibody. The results are presented in FIG. 12 as a ratio of the Mean Fluorescence Intensity (MFI) of the analyzed sample on the PBS sample.

In brief, these results show that antigen presenting cells, such as DCs and B cells and CD8+ T cells, are activated by PapMV VLP ssRNA nanoparticles. Activation is dependent on IRF5/7, Myd88 and TLR-7, as activation is lost in mice that are knockouts in IRF5/7, Myd88 or TLR7. It is believed that TLR-7 is triggered through the ssRNA that is contained in the VLPs. Experiments performed with the coat protein of PapMV (in monomeric or other low molecular weight form) failed to activate TLR-7.

IRF5/7 are the interferon responsive factors that are induced upon stimulation of TLR-7 and lead to production of interferon alpha. The Myd88 molecule is an adaptor molecule that is responsible for the transfer of the signals triggered by TLR-7. The cascade of the reaction is proposed to be: 1) triggering of TLR-7 by the ssRNA in the VLPs, and 2) engagement of Myd88 followed by the induction of IRF5/7 that will lead to an increase in interferon alpha production. Finally, interferon alpha will contribute to the immunomodulation effects of the PapMV VLP nanoparticles.

Example 7: Involvement of Plasmacytoid Dendritic Cells in PapMV VLP Immunogenicity C57BL/6 mice (5 per group) were immunized i.v. with 100 μg PapMV VLP ssRNA either with or without prior treatment to deplete BST2+ cells. For depletion, C57BL/6 mice were injected i.p. with 500 μg of an anti-BST2 antibody (mAb 927) at 48 h and 24 h prior to PapMV VLP ssRNA immunization. CD69, MHC-I and CD86 expression in isolated splenocytes was analyzed by FACS at 24 h after PapMV VLP ssRNA immunization.

Figure 13:
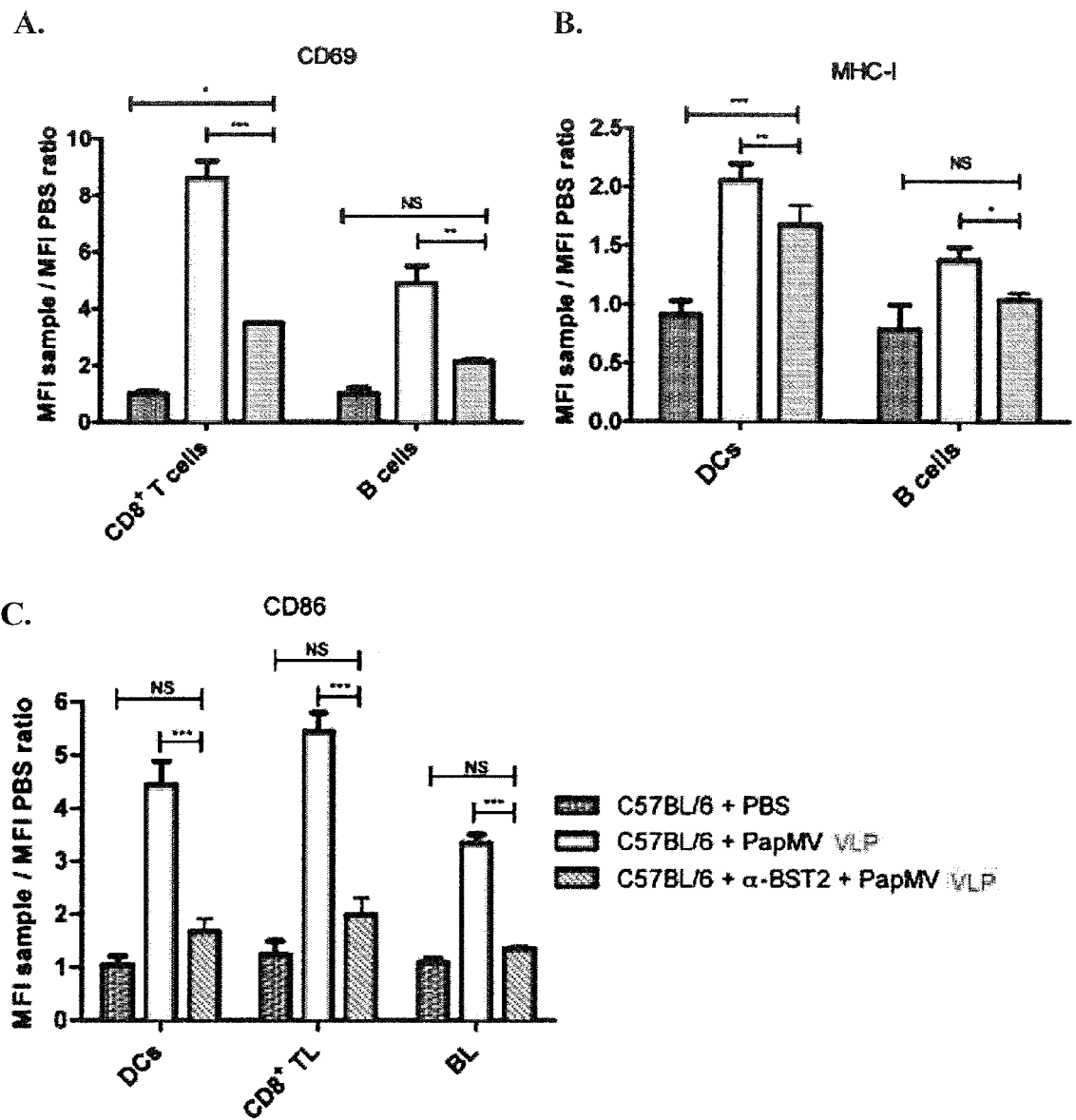
FIG. 13 presents graphs depicting compilation of flow cytometry analysis of (A) CD69, (B) MHC-I and (C) CD86 expression 24 h after immunization of C57BL/6 mice with PapMV PapMV VLP ssRNA with or without treatment with an anti-BST2 antibody. * $p<0.001$, $p<0.01$, *$p<0.05$, NS: not significant.

The results are shown in FIG. 13 and indicate that BST2$^+$ cells (mainly plasmacytoid dendritic cells) are important for the immunogenicity of PapMV VLP ssRNA nanoparticles in mice. Specifically, it was observed that in mice in which BST2+ cells were depleted, activation of B cells, CD8+ cells and DCs was lost, suggesting that the activation is going through the plasmacytoid dendritic cells.

Example 8: Stimulation of Interferon-α Production of by PapMV VLPs #1

Two groups of C57BL/6 mice, as well as TLR-7 KO and MYD88 KO mice (4 mice per group) were immunized i.v. with 100 μg PapMV VLP ssRNA or 100 μl PBS. One group of C57BL/6 mice had first been treated with anti-BST2 antibody as described in Example 7. IFN-α production in serum and spleen was monitored by ELISA (VeriKine™ Mouse Interferon Alpha ELISA Kit; PBL InterferonSource) at either 6, 12, 24 and 48 h post-immunization (FIG. 14A) or at 6 h after the immunization (FIG. 14B).

Figure 14:
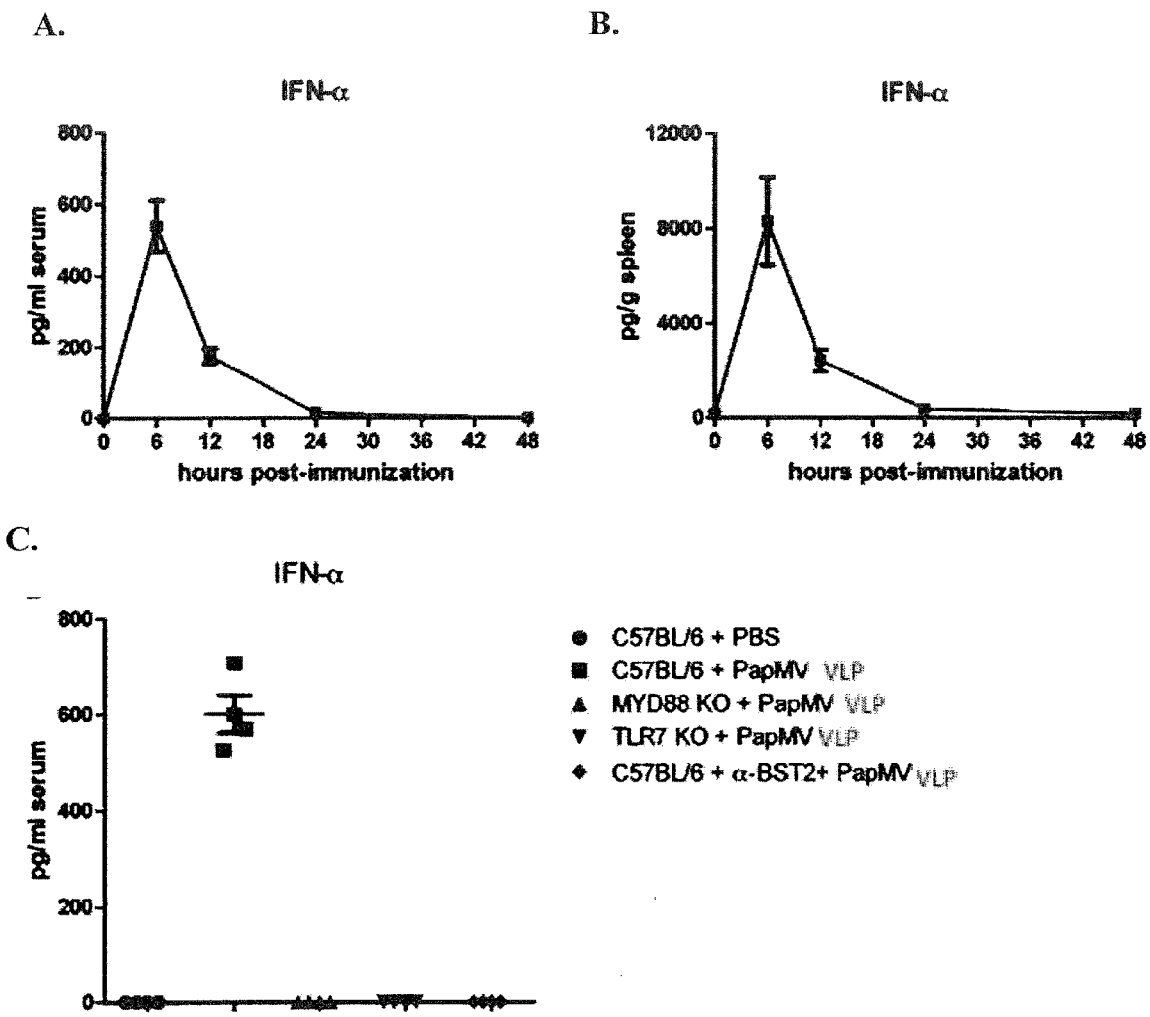
FIG. 14 presents graphs depicting (A) evaluation by ELISA of the kinetics of production of IFN-α in serum and (B) spleen of C57BL/6 mice following immunization with 100 μg PapMV VLP ssRNA, and (C) ELISA quantification of serum IFN-α in C57BL/6 and different knockout mice 6 h post-immunization with 100 μg PapMV VLP ssRNA or PBS.

The results are shown in FIG. 14 and indicate that IFN-α production stimulated by PapMV VLP ssRNA nanoparticles depends on MYD88, TLR7 and BST2$^+$ cells.

Example 9: Stimulation of Interferon-α Production of by PapMV VLPs #2

C57BL/6 and IFNAR KO mice (3 mice per group) were immunized i.v. with 100 μg PapMV VLP ssRNA or 100 μl PBS. CD86, MHC-I and CD69 expression in B lymphocytes and dendritic cells isolated from the spleens of the mice 24 h after immunization was assessed by flow cytometry.

Figure 15:
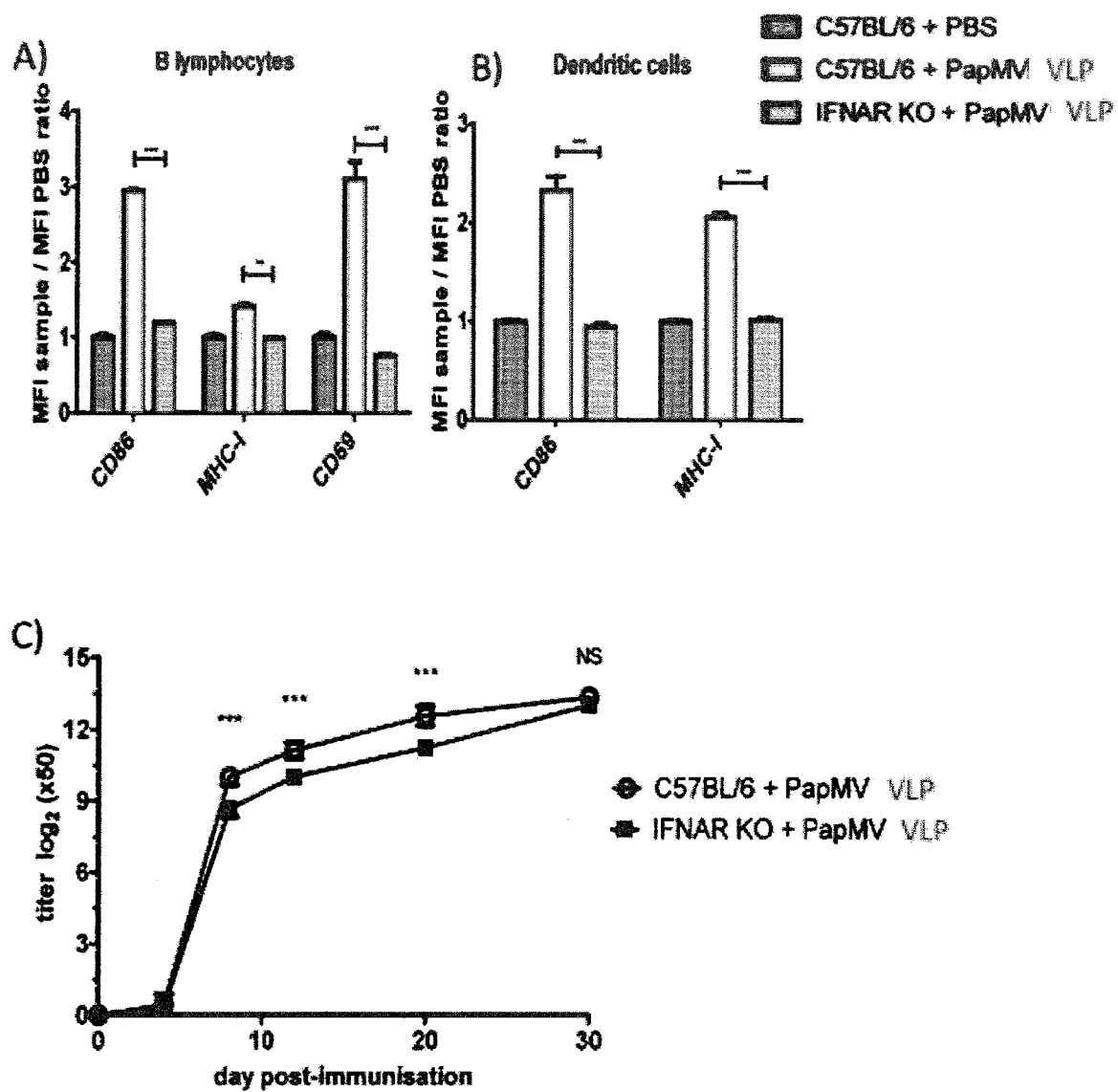
FIG. 15 presents graphs depicting a compilation of CD86, MHC-I and CD69 expression in (A) B lymphocytes and (B) dendritic cells from spleens of C57BL/6 and IFNAR KO mice 24 h after immunization with PapMV VLP ssRNA or PBS, and (C) quantification by ELISA of antibody against PapMV VLP ssRNA in serum of C57BL/6 and IFNAR KO mice at different time points after PapMV VLP ssRNA immunization.

The results are shown in FIGS. 15A and B, and indicate that the type I IFN receptor is necessary for the activation of murine immune cells by PapMV VLP ssRNA nanoparticles. Mice that were knockouts for the type I IFN receptor (IFNAR KO) did not show activation of the immune cells by PapMV VLP ssRNA nanoparticles.

Levels of antibody against PapMV VLP ssRNA in the serum of C57BL/6 and IFNAR KO mice (9 mice per group) at day 4, 8, 12, 20 and 30 after immunization with 100 μg PapMV VLP ssRNA were analyzed by indirect ELISA measuring total IgG binding to PapMV VLP ssRNA coated plate.

The results are shown in FIG. 15C and indicate that the absence of type I IFN signalling causes a significant delay in the antibody response against the PapMV VLP ssRNA nanoparticles.

Example 10: Pre-Treatment with PapMV VLPs Helps to Control Chronic Infection

LCMV is a relevant animal model of chronic infection (such as HCV infection). The clone 13 variant of LCMV establishes a persistent infection in mice. LCMV infection, like HCV infection, is largely controlled by CTLs and exhaustion of the CTL response is associated with PD-1 expression.

C57BL/6 and TLR7 knockout (KO) mice (3-6 mice per group) were treated i.v. with 100 μg PapMV VLP ssRNA, 100 μg R837 (a commercially available TLR-7 ligand) or 100 μl PBS 6 hours before infection (i.v.) with $2 \times 10^6$ PFU LCMV clone 13. Blood samples were taken at day 5, 11, 15, 25 and 45 to evaluate the viral titer by LCMV focus-forming assay. Mice were sacrificed 15 days or 45 days post-infection for analysis of the immune response in the spleen by FACS and of the viral titer in the spleen, liver, kidney and brain by LCMV focus-forming assay on MC57 fibroblasts using a rat anti-LCMV-NP monoclonal Ab (VL-4) as previously described (Lacasse et al., 2008, *J. Virology*, 82:785-794).

Figure 16:
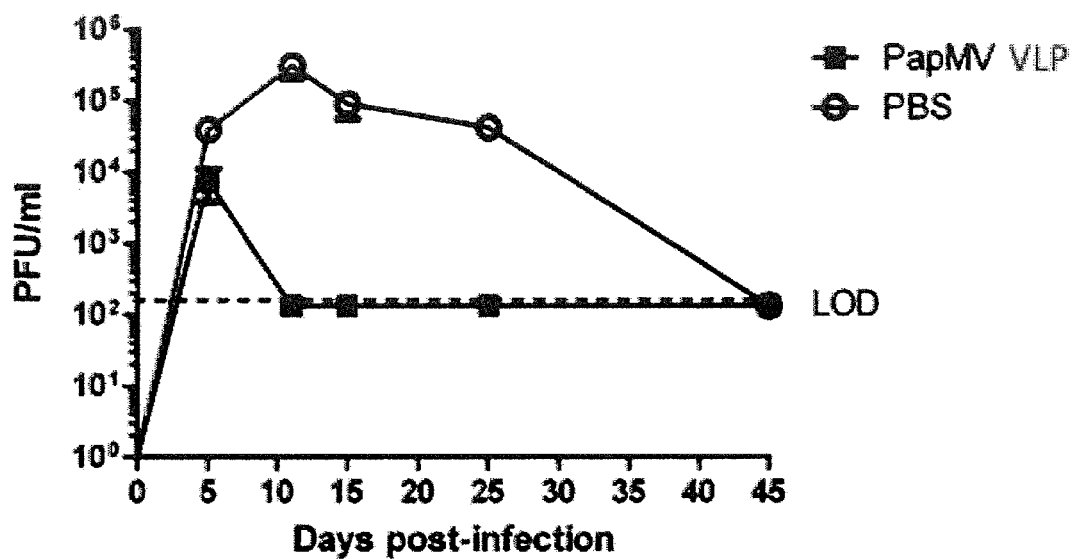
FIG. 16 presents a graph depicting the viral kinetics of LCMV clone 13 in blood of C57BL/6 mice treated with 100 μg PapMV VLP ssRNA (filled squares) or PBS (open circles) 6 hours before infection with $2\times10^6$ PFU LCMV clone 13 (titers are expressed in PFU per milliliter of blood; LOD: limit of detection).

The viral kinetics of LCMV clone 13 in the blood of the C57BL/6 mice are depicted in FIG. 16 and show that pre-treatment with PapMV VLP ssRNA nanoparticles control chronic infection induced by LCMV.

Figure 17:
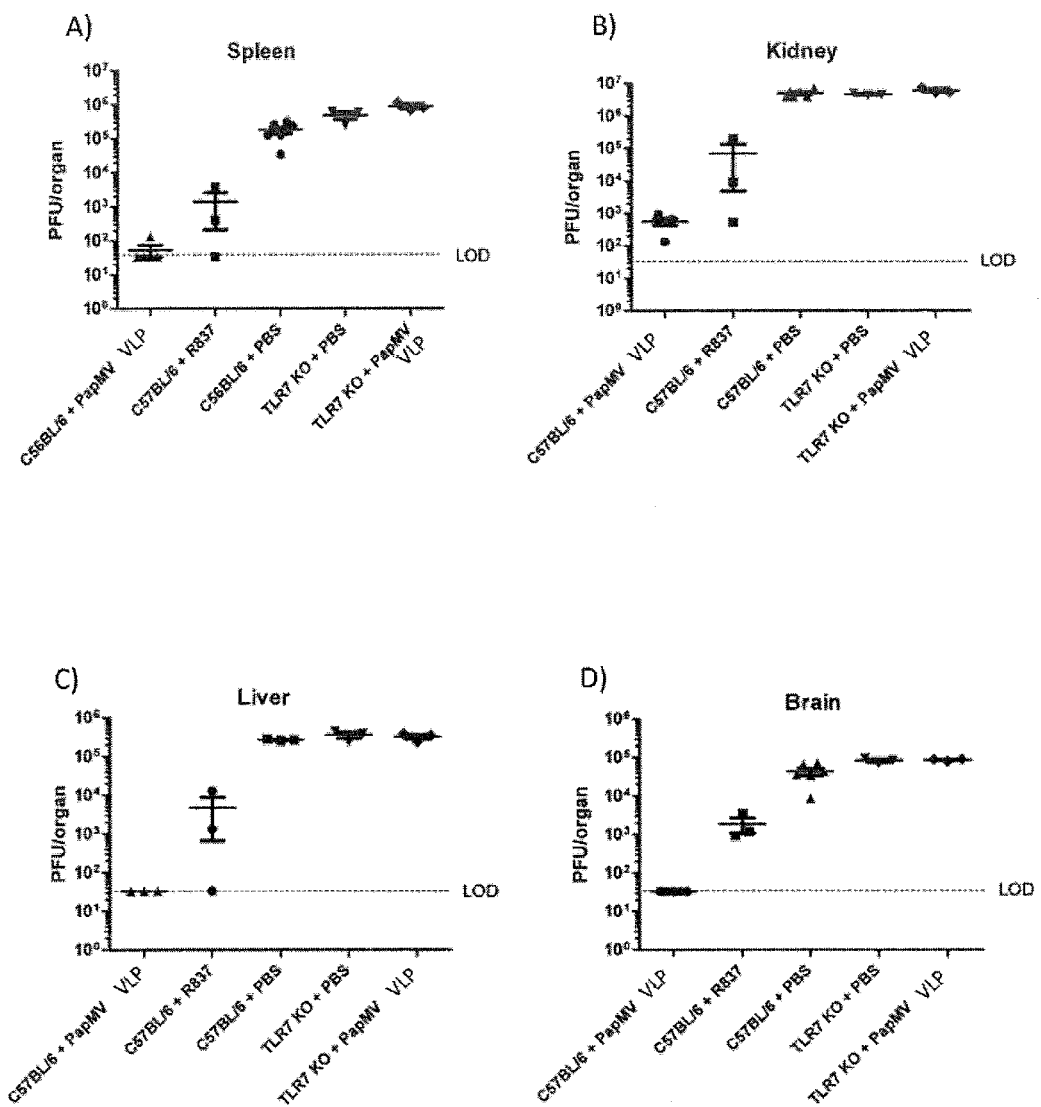
FIG. 17 presents graphs depicting the viral titers in (A) spleen, (B) kidney, (C) liver and (D) brain of C57BL/6 and TLR7 knockout (KO) mice 15 days after infection with $2\times10^6$ PFU LCMV clone 13; mice were treated with 100 μg PapMV VLP ssRNA, 100 μg R837 or PBS 6 hours before infection (titers are expressed in PFU per organ). LOD: limit of detection.

The viral titers in spleen, kidney, liver and brain of C57BL/6 and TLR7 KO mice at day 15 post-infection are shown in FIG. 17 and demonstrate that pre-treatment with PapMV VLP ssRNA nanoparticles decreases the viral load in different organs with greater efficiency than a commercial TLR7 ligand (R837) and in a TLR7 dependent manner. It is believed that the TLR-7 ligand in the PapMV VLP ssRNA nanoparticles is the ssRNA component, which represents approximately 5% of the molecule. As such, although 100 μg of each was administered to the mice, the PapMV VLP ssRNA nanoparticles are more than 20-fold more effective than R837 in reducing the LCMV viral load in the mice.

FIG. 18 shows that administration of PapMV VLP ssRNA nanoparticles before infection with LCMV clone 13 increases the functionality of GP33 specific CD8$^+$ T cells. Similar results were obtained for NP396 specific CD8$^+$ T cells. In particular, FIG. 14F shows that the amount of PD-1 expressed in GP33 specific CD8$^+$ T lymphocytes is significantly decreased by pre-treatment with PapMV VLP ssRNA nanoparticles. PD-1 is an indicator of immune exhaustion and its expression is a characteristic of LCMV clone 13 infection. Pre-treatment of the mice with PapMV VLP ssRNA nanoparticles resulted in the PD-1 level remaining as low as in the uninfected mice suggesting that the immune system is not exhausted in these mice, which is why they are able to resist infection.

Figure 19:
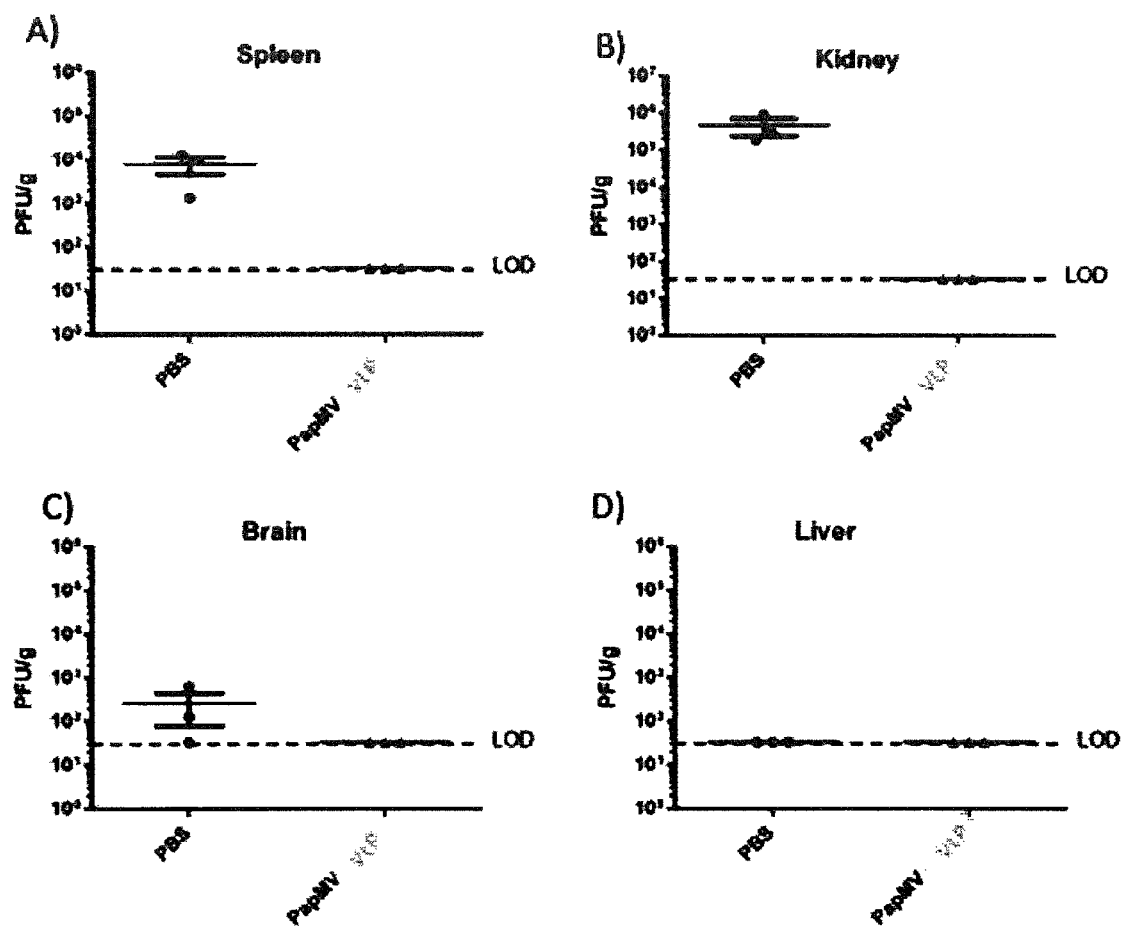
FIG. 19 presents graphs depicting the viral titers in (A) spleen, (B) kidney, (C) brain and (D) liver of C57BL/6 mice 45 days after infection with $2\times10^6$ PFU LCMV clone 13; mice were treated with 100 μg PapMV VLP ssRNA or PBS 6 hours before infection (titers are expressed in PFU per organ). LOD: limit of detection.

FIG. 19 shows the viral titers in spleen, kidney, liver and brain of C57BL/6 mice at day 45 post-infection. This result indicates that the decrease in viral load resulting from pre-treatment with PapMV VLP ssRNA nanoparticles is still evident several weeks after treatment.

Example 11: Activation of Human Monocytes In Vitro by PapMV VLPs

Human PBMCs were isolated by Ficoll gradient and treated with 100 μg/ml PapMV VLP ssRNA or PBS. At 18 h post-treatment, CD14$^+$CD11b$^+$ cell population (monocytes) were analyzed for CD86 expression by flow cytometry.

Figure 20:
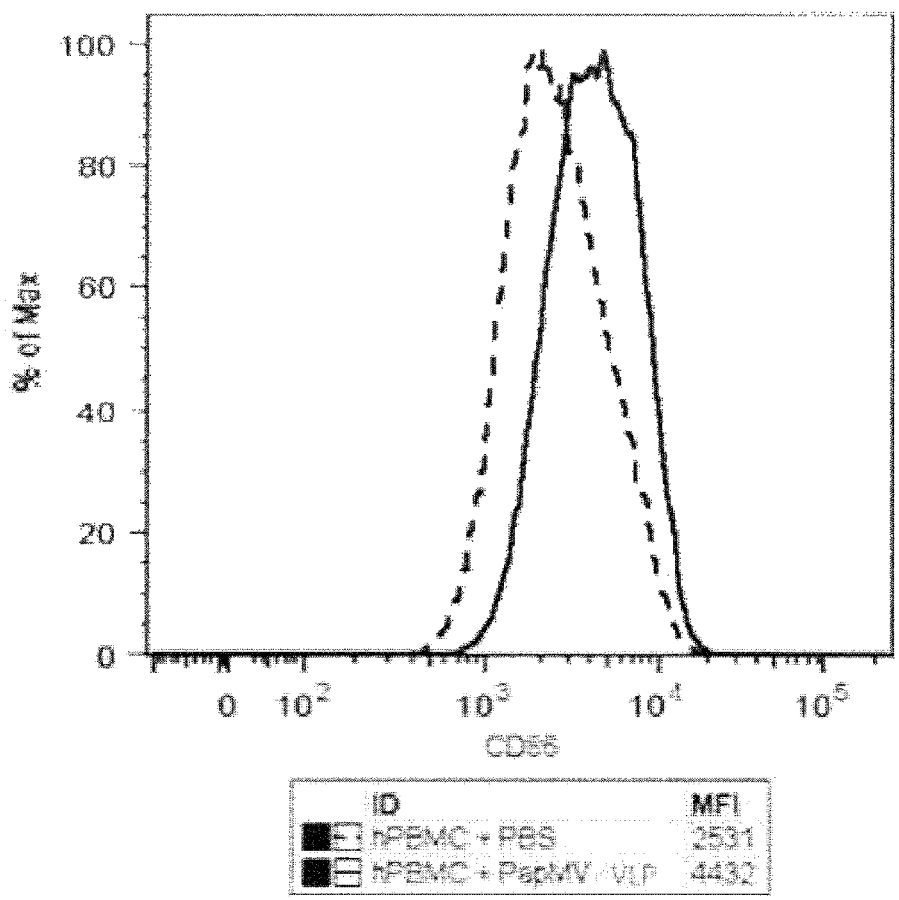
FIG. 20 presents a chart depicting flow cytometry analysis of CD86 expression in human PBMCs (CD14$^+$CD11b$^+$ cell population) 18 h after stimulation with PapMV VLP ssRNA (MFI: mean fluorescence intensity).

The results are shown in FIG. 20 and indicate that human monocytes are also activated by PapMV VLP ssRNA nanoparticles. These results are representative of three independent experiments.

Example 12: Induction of an Anti-Bacterial Response by PapMV VLPs

Mice, 10 per group, were treated twice at 7-day intervals via the intranasal route with buffer alone (10 mM Tris pH8) or with 60 μg of PapMV VLP ssRNA. At day 3 post-treatment, the mice were infected with 220 CFU (colony forming units) of a virulent *Streptococcus pneumoniae* strain.

Figure 21:
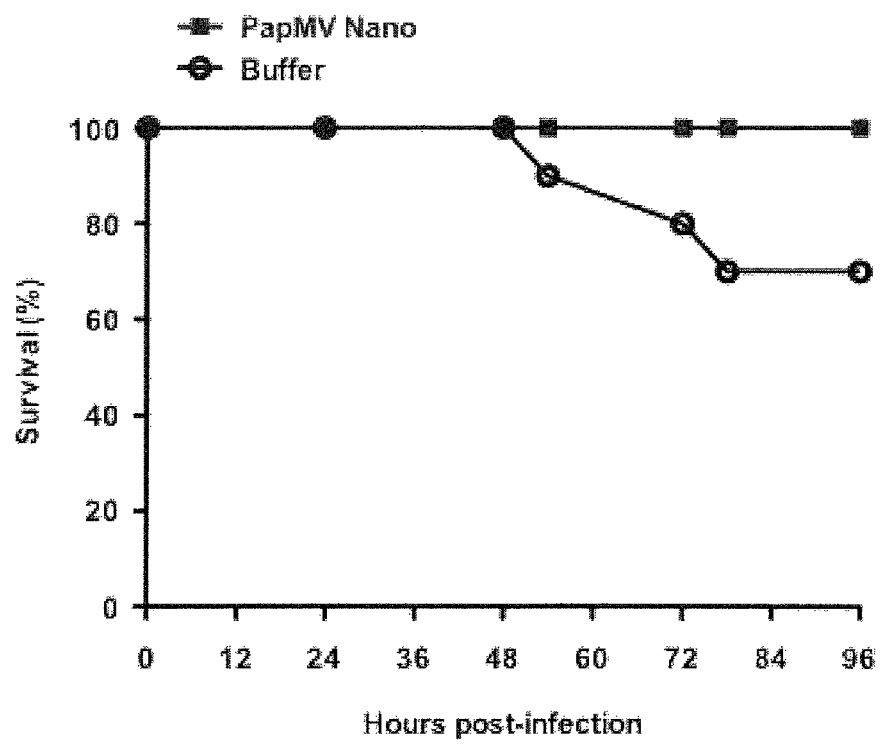
FIG. 21 presents a graph depicting survival of mice treated with 2 doses of PapMV VLP ssRNA at 2-week intervals prior to challenge with a sub-lethal dose of *Streptococcus pneumoniae*.

Survival was monitored closely every 12 hours over 4 days. The results are shown in FIG. 21. All mice in the group treated with PapMV VLP ssRNA nanoparticles survived the infection. The group treated with the buffer showed 70% survival.

Although the dose of *Streptococcus pneumoniae* used in this Example was a sub-lethal dose, the data strongly suggests that pre-treatment with PapMV nanoparticles will provide protection against a bacterial infection through the induction of an innate immune response in the lungs. This Example and the preceding Examples demonstrate that the protection conferred by the PapMV nanoparticles is non-specific as it is effective against infection with viruses and bacteria.

Example 13: Treatment of LCMV Chronic Infection Using PapMV VLPs

C57BL/6 Mice (3 per group) were infected i.v. at day 0 with $2 \times 10^6$ PFU LCMV clone 13 and treated i.v. once/day with 100 μg PapMV VLP ssRNA or 100 μl PBS either at days 1, 2, 3, 4 and 5 (Group A), or at days 6 and 7 only (Group B). Blood samples were taken at day 5, 10 and 15 and mice were sacrificed at day 15 post-infection for analysis of the viral titer by LCMV focus-forming assay in blood, spleen, kidney and brain.

Figure 22:
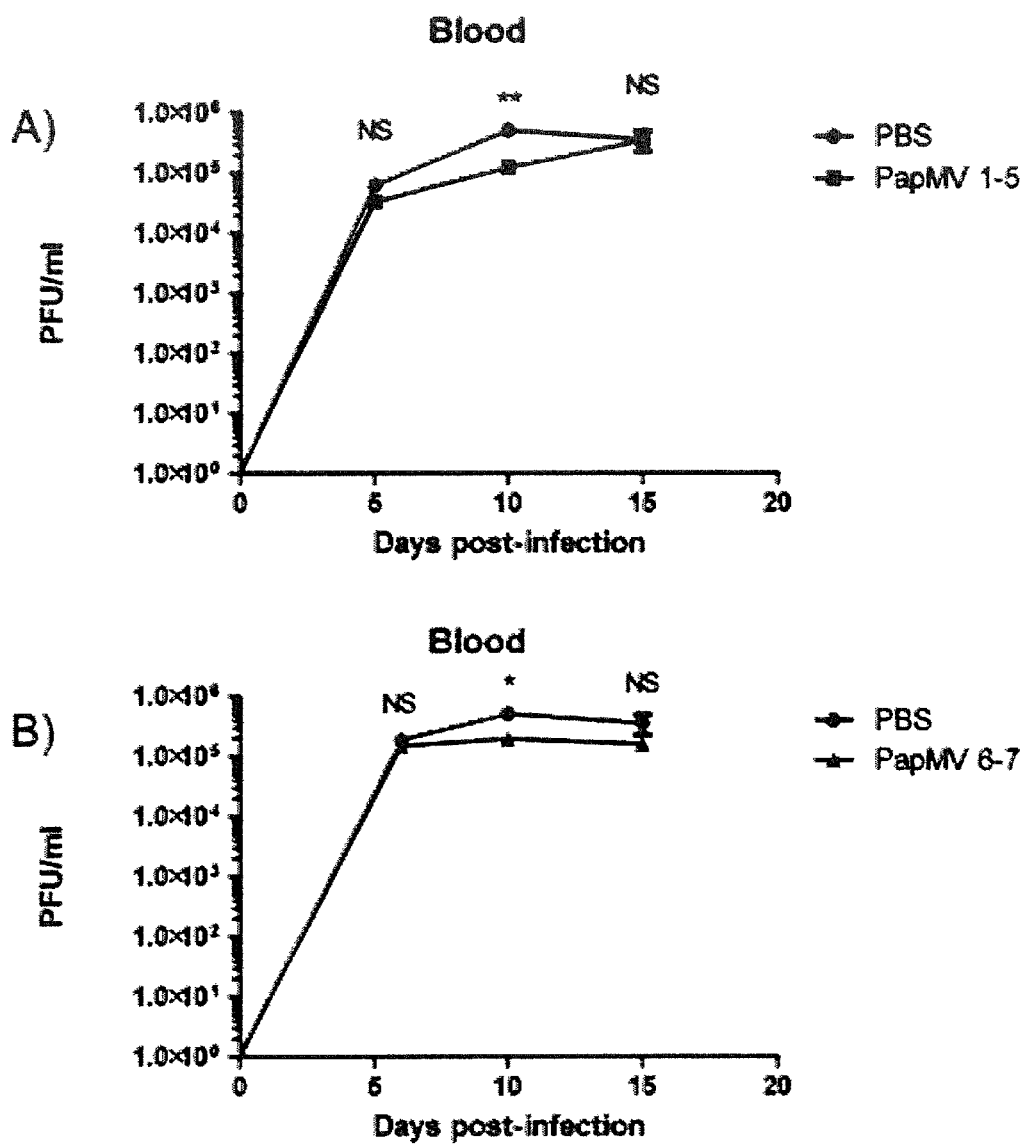
FIG. 22 presents graphs depicting viral load in mice chronically infected with LCMV and treated i.v. once/day with 100 μg PapMV VLP ssRNA (A) at day 1, 2, 3, 4 and 5 post-infection, and (B) at day 6 and 7 post-infection only (titers are expressed in PFU/mL).

Viral titers found in the blood of the animals are shown in FIG. 22. Although at day 15, mice treated with PapMV VLP ssRNA nanoparticles showed the same titers as the controls, a significant reduction of viral titers was observed at day 10 in both groups of mice (close to a log 10 reduction in the animals of Group A). This result strongly suggests that, with adjustment to the treatment regimen, further decreases in viral load in mice treated with PapMV VLP ssRNA nanoparticles will be achievable. For example, the number of treatments could be increased. As treatments provided at days 1 to 5 or 6 and 7 showed a decrease in LCMV titers, it is likely that an increase in the number of treatments after days 6 and 7 will provide a further decrease in viral load. Alternatively, or in addition, the amount of PapMV VLPs administered could be increased, for example, to 200 μg per dose.

Figure 23:
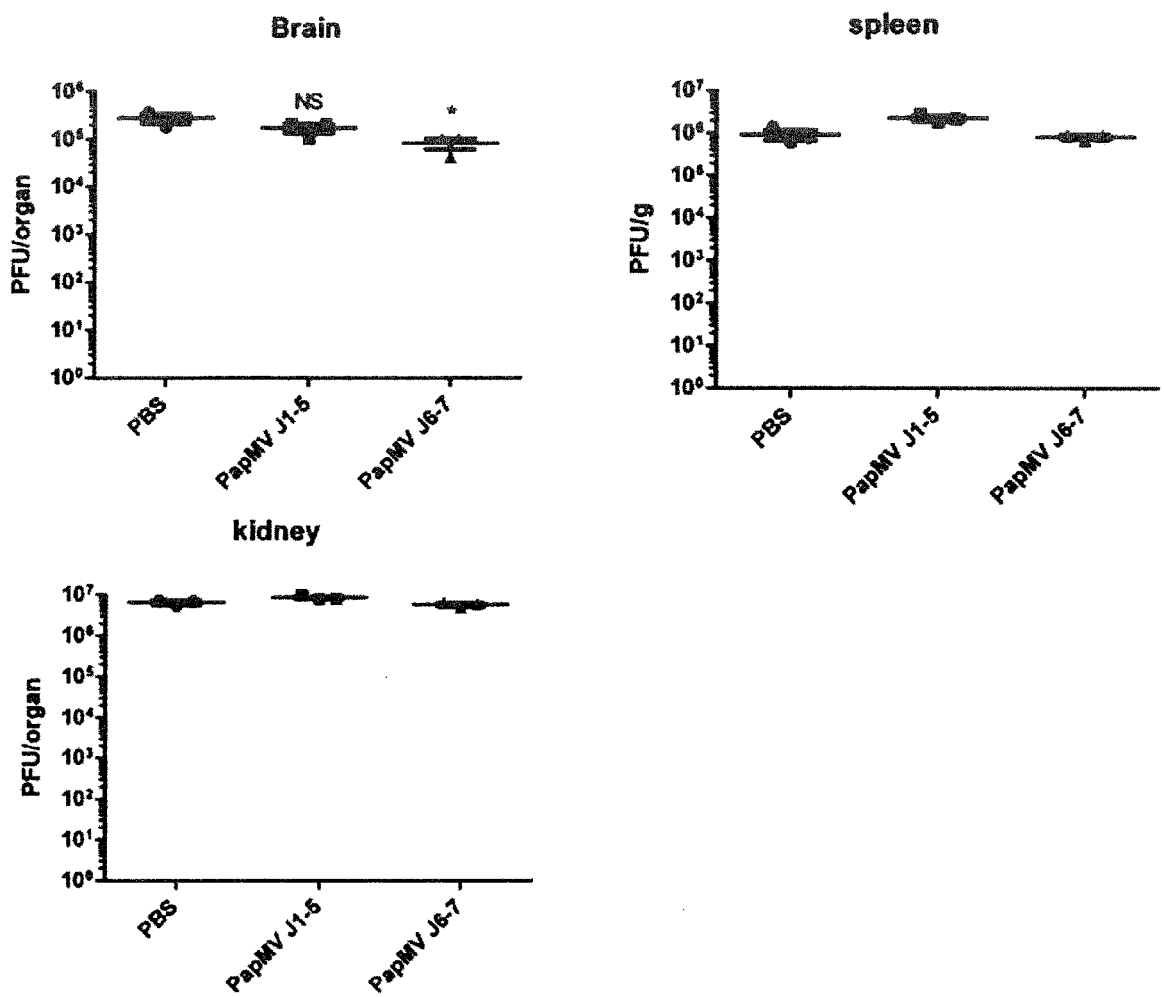
FIG. 23 presents graphs depicting the viral titers in different organs of mice treated as described for FIG. 22 at day 15 (end of the experiment).

Viral titers found in various organs of the animals are shown in FIG. 23. While the viral load in the brain of animals treated at days 6 and 7 (Group B) showed a significant reduction, viral loads in other organs of the treated mice did not show a significant reduction. This is most likely because the titers were measured at day 15, which allowed the infection sufficient time to 'kick back' after treatment. Subsequent treatments to days 6 and 7 would be anticipated to lead to a more significant decrease in viral loads.

Example 14: Multiple Treatments with PapMV VLPs Prolong the Protection Period

Protection induced by the treatment with PapMV VLPs has been shown to persist for a period of about 5 days. To investigate if treatment with multiple doses of PapMV VLPs could provide a longer period of protection, mice were inoculated intranasally with 60 μg of PapMV VLPs containing ssRNA once (1×), twice (2×), 5 times (5×) or 10 times (10×) at 1-week intervals. Three days after the final treatment, the mice were challenged with influenza WSN/33 virus (approximately 1 $LD_{50}$).

Figure 24:
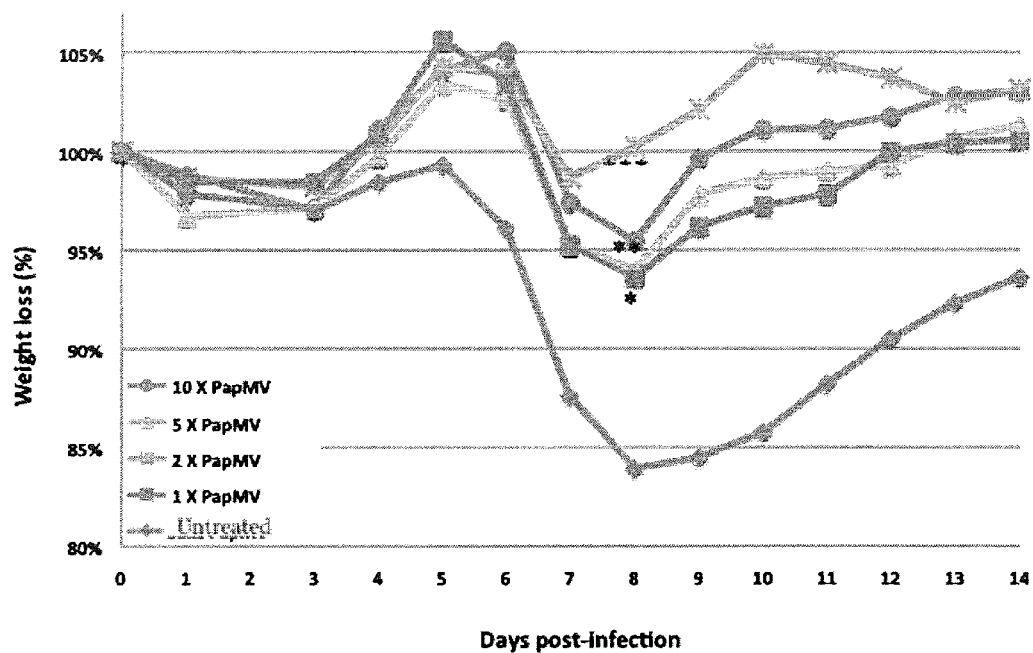
FIG. 24 presents a graph illustrating weight loss in mice treated once (1×), twice (2×), 5 times (5×) and 10 times (10×) at 1-week intervals with PapMV VLPs and challenged with the influenza WSN/33 virus 3 days after the last treatment.

The weight loss of the mice is shown in FIG. 24. It was also noted that the animals were not affected by the multiple treatments and gained weight normally during the treatment period in line with the control animals.

These results show that multiple treatments can extend the period of protection induced by the PapMV VLP nanoparticles to more than 10 weeks. The results also demonstrate that multiple treatments with PapMV VLPs do not exhaust the innate immunity of the animal. Finally, as it is known that antibodies to the PapMV VLPs appear 7 days after the first treatment and increase with booster treatments, these results demonstrate that the ability of the PapMV VLPs to trigger the innate immune response is not impacted by the production of antibodies.

Example 15: Induction of Neutrophil Recruitment by PapMV VLPs

Figure 25:
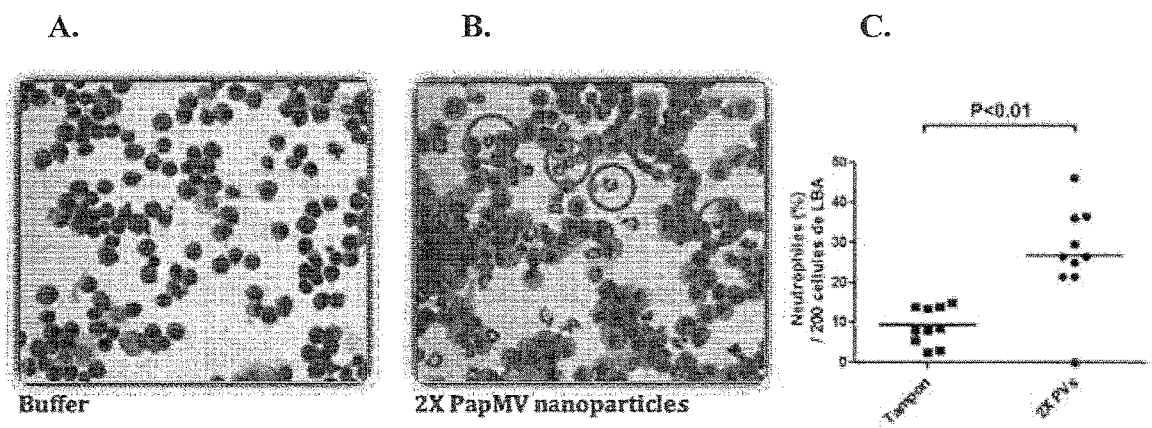
FIG. 25 presents electron micrographs showing cells found in broncho-alveolar lavage (BAL) from mice treated with (A) buffer and (B) PapMV VLPs (neutrophils are circled), and (C) a graph depicting numbers of neutrophils found in the BAL.

Mice were submitted to 2 instillations of PapMV VLPs containing ssRNA according to the protocol of Example 3 and broncho-alveolar lavage (BAL) was performed 6 hours after the second treatment. The results are shown in FIG. 25. Neutrophils found into the BAL of mice treated with PapMV VLPs are circled in FIG. 25B. Three times more neutrophils were observed in the treated mice compared to the control group.

Neutrophils represent the first line of defense. This Example demonstrates that neutrophils are recruited rapidly in mice treated with PapMV VLPs; just 6 hours after treatment. Neutrophils are known to play a key role in the control of bacterial and viral infection in the lungs and thus likely play a role in the protection observed in PapMV treated mice.

Example 16: Induction of a Mucosal Immune Response by PapMV VLPs Containing ssRNA Balb/C mice (10 per group) were treated with two instillations of 20 μg PapMV VLP ssRNA combined with 2 μg of the trivalent inactivated flu vaccine (TIV) at 14 day intervals. Bleedings were performed at day 0, 14 and 28. Following the same protocol, another group of mice were immunized animals by the s.c. route for comparison. Mice were challenged at day 15 with $1LD_{50}$ of the influenza WSN/33 virus and weight loss was followed over a 14 day period.

IgG titers were measured in the blood of the immunized animals by ELISA using antibodies to the TIV and the results are shown in FIG. 26. The addition of PapMV VLPs to the TIV increased significantly the total IgG and the IgG2a response as compared with the group immunized with TIV alone when the same route of immunization was used. Interestingly, the s.c. route was more efficient than the i.n. route for production of total IgG and IgG2a in the blood of the animal.

Figure 27:
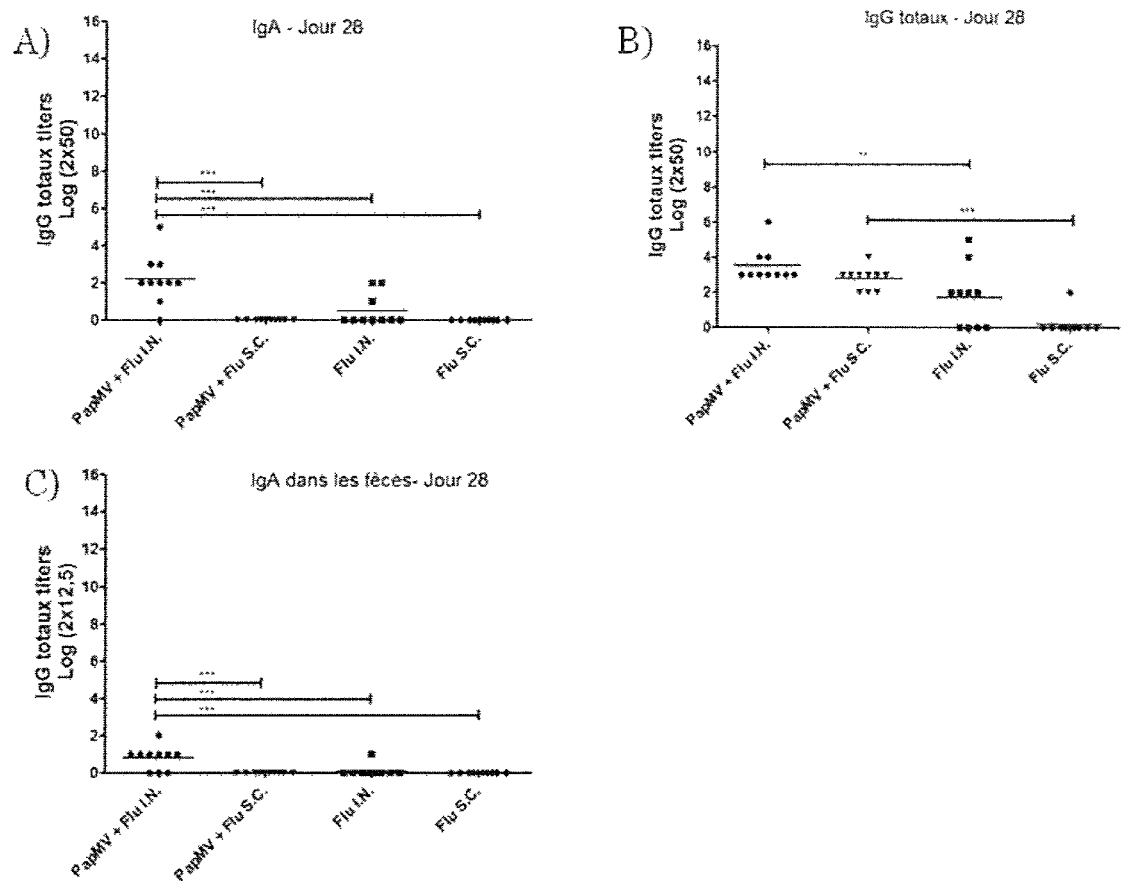
FIG. 27 presents graphs depicting the antibody titers measured in mice immunized as described for FIG. 23 after two immunizations, (A) IgA titers in the broncho-alveolar lavage (BAL), (B) total IgG titers in the BAL, and (C) IgA in the faeces.

Antibody titers were measured in the broncho-alveolar lavage (BAL) and in the faeces of the immunized animals by ELISA using antibodies to the TIV and the results are shown in FIG. 27. From these results, it is clear that only i.n. treatment triggers production of IgA in the BAL. The addition of PapMV VLPs to the TIV increased significantly the amount of IgA in the lungs as compared to instillation with TIV alone. Significantly higher total IgG in the BAL was also observed in the animals treated with PapMV VLPs in combination with the TIV, as compared to the TIV alone group. The amount of total IgG in the BAL obtained from mice treated intranasally with PapMV VLPs in combination with the TIV administered by i.n. was not significantly different from that in mice treated subcutaneously with the combination. Finally, it was interesting to note that a mucosal immune response was also observed in the intestines of the mice treated intranasally with the combination as shown by the presence of IgA directed to TIV in this organ (FIG. 27C).

Figure 28:
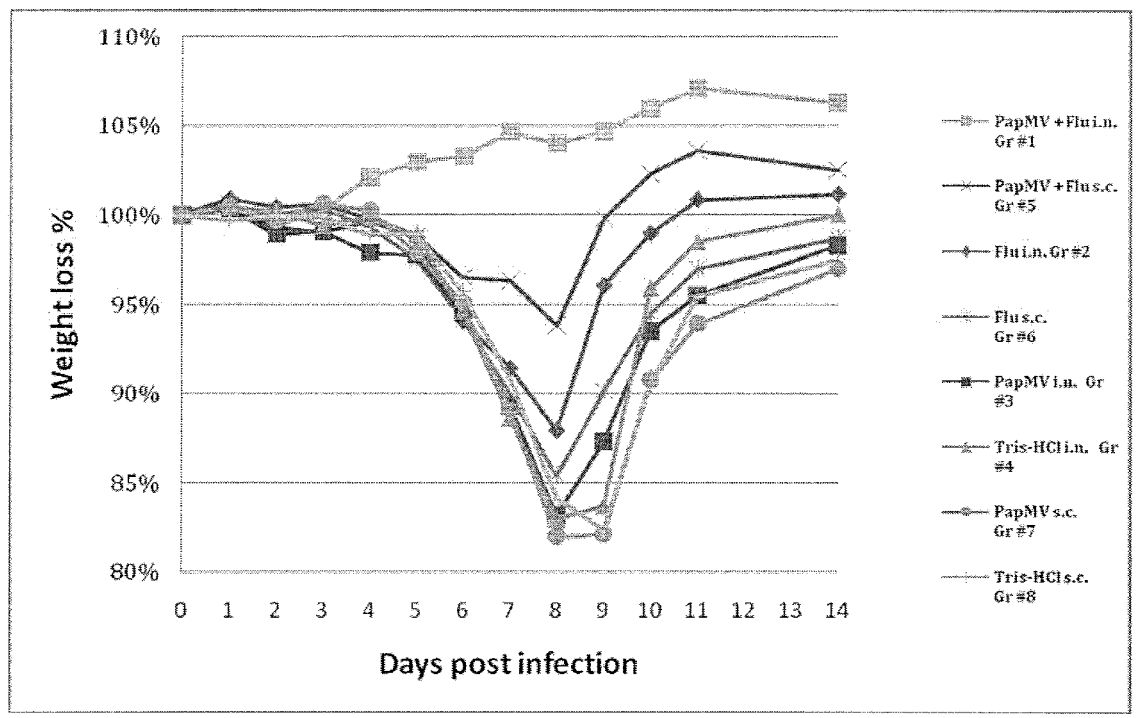
FIG. 28 presents a graph showing weight loss in mice immunized as described for FIG. 26 and challenged at day 15 with $1LD_{50}$ of the influenza WSN/33 virus; weight loss was followed over a 14 day period.

Weight loss in the mice after challenge with the influenza virus is shown in FIG. 28. The challenge revealed that immunization by the intranasal route is more robust and efficient in protecting mice to a heterosubtypic strain than immunization by the s.c. route. In the group immunized by the i.n. route with the combination of PapMV VLPs and TIV, the mice gained weight and did not show any symptoms. The combination administered s.c. provided only a partial protection. Complete protection can, however, be achieved using s.c. administration of 3 μg of TIV with 30 μg of PapMV VLPs. All the other groups that were immunized with TIV alone (by either route), PapMV VLPs alone or the control buffer were not protected, showed symptoms of disease and lost significant amounts of weight.

The results from this experiment demonstrate that PapMV VLPs can act as a mucosal adjuvant. The ability of an adjuvant to trigger a mucosal immune response is important for effective prevention or treatment of infections and diseases caused by micro-organisms that gain access to the body via mucosal membranes, including influenza, tuberculosis, and *H. pylori* infections. The presence of IgG in the faeces of the immunized animals suggests that i.n. vaccinations using PapMV VLPs as adjuvant could be used to protect against bacterial or viral infection in the intestine. In addition, since the mucosal immune response triggered by the PapMV VLPs is general, i.n. vaccinations using PapMV VLPs as adjuvant could potentially also be used to protect against bacterial or viral infection (such as HIV-1) in the vaginal mucosa.

Although in this experiment no protection was seen in mice treated i.n. with PapMV VLPs alone, this is consistent with the results in the previous examples which indicate that the non-specific protection induced by PapMV VLPs lasts only for a period of about 5 days. In this experiment, the challenge was performed 14 days after the second instillation of VLPs.

Example 17: Activation of TLR-2 and CD14 by PapMV VLPs

As demonstrated in the preceding Examples, PapMV VLPs prepared in bacterial host cells and PapMV VLPs prepared by in vitro self-assembly with ssRNA are both able to stimulate the innate immune response. However, VLPs prepared by the two different methods, activate different TLRs. As shown above, PapMV VLPs prepared by in vitro self-assembly with ssRNA activate TLR-7. In contrast, PapMV VLPs prepared by expression of the PapMV coat protein and self-assembly in *E. coli* cells as previously described (Tremblay et al., 2006, ibid.), activate TLR-2 and CD14.

In brief, THP1-XBlue™-CD14 cells (InvivoGen, San Diego, Calif.) were treated with 100 µg PapMV VLPs (prepared according to Tremblay et al.) or a known TLR ligand (100 µg lipoteichoic acid from *S. aureus* (LTA): TLR2 and CD14 ligand; 1 µg Pam3SCK4: TLR2 ligand; or 10 µg TLR5 ligand) and either an anti-CD14, anti-TLR2 or anti-TLR5 antibody. THP1-XBlue™-CD14 cells harbour several TLRs (including TLR2, 4, 5) and have been modified to produce a blue colour when a TLR is engaged with a ligand. Upon engagement, the cells become blue and the strength of the engagement can be readily evaluated using a spectrophotometer. Measurements were made after a 24 hour incubation of the cells at 37° C.

Figure 29:
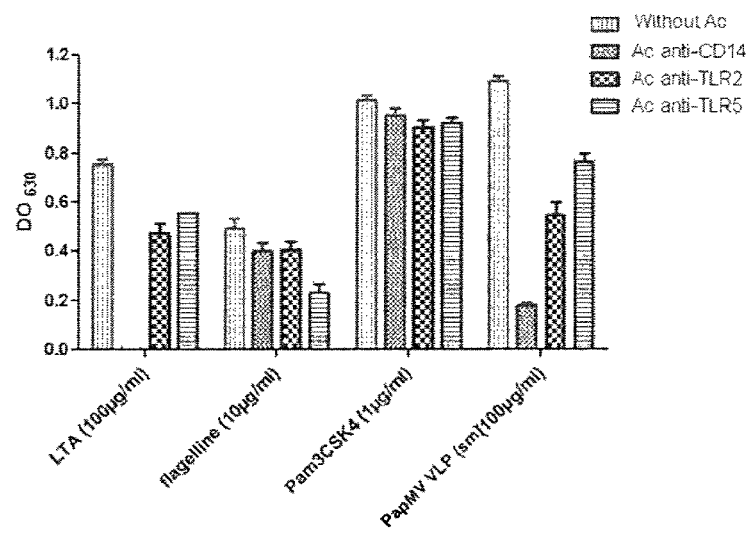
FIG. 29 presents a graph demonstrating that PapMV VLPs produced in bacterial cells interact with TLR-2 and CD14 in a human monocyte cell line (THP-1) and that this interaction is blocked with antibodies (Ac) to TLR-2 and CD14.

The results are shown in FIG. 29. Antibodies (Ac) directed to CD14, TLR2 or TLR5 blocked engagement of the respective TLR or CD14 and revealed what interactions were being made by each test molecule. A significant decrease in optical density was observed when the anti-TLR2 antibody was used with the PapMV VLPs, and a strong decrease observed when the anti-CD14 antibody was used. In this experiment, the antibody to TLR2 did not work as well as expected as a higher decrease should have been observed when Pam3CSK4 (a known TLR2 ligand) was used. It is likely the amount of Pam3CSK4 used in the experiment was too high.

The difference in TLR activation seen with the PapMV VLPs assembled in bacteria may be due to the detergent treatment that the VLPs undergo after isolation from the bacterial cells. This treatment may affect the surface of the PapMV VLPs, for example to expose hydrophobic residues, and result in the VLPs becoming a ligand of TLR2. In contrast to TLR7, which is present in the endosome, both TLR2 and CD14 are surface exposed on immune cells.

Example 18: Adjuvant Activity of PapMV VLPs Containing ssRNA

The nucleoprotein (NP) from the H1N1 pandemic influenza virus strain A/california/7/2009 was expressed in *E. coli* as a His-tag protein and purified on a nickel affinity column. The NP antigen (10 µg) was mixed with 10, 30, 60 or 90 µg of PapMV VLPs prepared as described in Example 2 and used to inoculate Balb/C mice (10 per group) 21 days after inoculation, blood samples were collected and analyzed by ELISA using GST-NP antigen in order to evaluate the humoral response.

Figure 30:
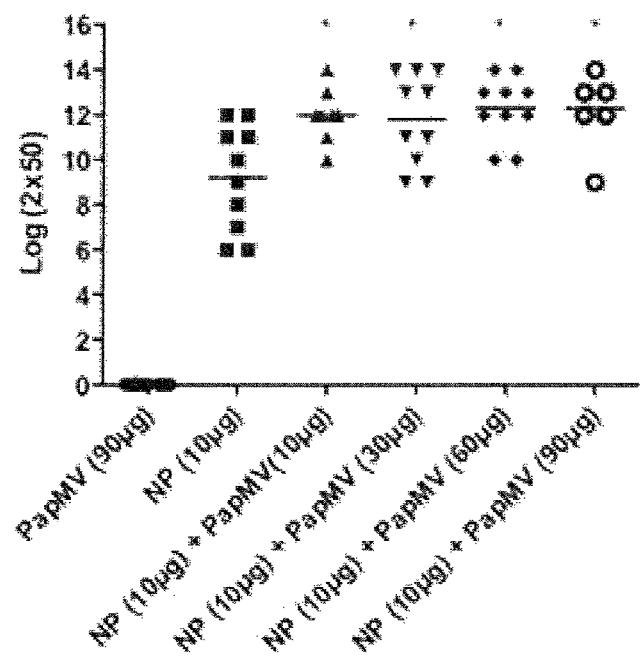
FIG. 30 presents a graph showing the IgG2 levels in mice inoculated with 10 µg NP from influenza virus H1N1 A/california/7/2009 in combination with varying amounts of PapMV VLPs as adjuvant (*p<0.05 as compared to the NP (10 µg) alone).

The results are shown in FIG. 30, and demonstrate that the use of a combination of 10 µg NP and 10 µg PapMV VLPs was sufficient to saturate the humoral response to NP.

In a separate experiment, Balb/C mice (10 per group) were immunized s.c. 3 times at 14 day intervals with a formulation containing 10 µg NP (from H1N1 strain A/california/7/2009) alone or mixed with PapMV VLPs as adjuvant (10, 30, 60 or 90 µg). The mice were challenged at 14 days after the final immunization with the heterosubtypic influenza strain H1N1 WSN/33 (approximately 1 $LD_{50}$). Symptoms were followed for 14 days after challenge. Weight loss and symptoms were scored every day.

The results are shown in FIG. 31 and show that mice immunized with the adjuvanted formulations showed the best protection to the influenza challenge. The group inoculated with NP (10 µg)+90 µg of PapMV showed the lowest symptoms and the lowest weight loss. The observed protection against an heterosubtypic strain of influenza suggests strongly that a CTL response directed to the highly conserved protein NP was induced with the PapMV adjuvant providing a better protection against infection. Antibodies to NP as shown in FIG. 30 are unlikely to neutralise the infection since NP is found at the interior of the virus, thus implying the involvement of a CTL response in the protection observed in the challenged mice. The presence of the IgG2a isotype directed to NP when mixed with the PapMV VLP adjuvant indicates that a $T_{H1}$ response was induced, which is consistent with the triggering of a CTL response.

This result thus indicates that the use of the PapMV VLPs containing ssRNA as an adjuvant enhances both the induction of antibodies and the CTL response.

Example 19: Adjuvant Activity of PapMV VLPs Containing ssRNA and PapMV SM VLPs

This Example compares the adjuvant activity of PapMV VLPs prepared by the process according to the present invention and PapMV VLPs (PapMV sm) prepared by the method described in Tremblay et al. (2006, ibid). Both types of VLPs have the same appearance under the electron microscope.

Briefly, Balb/C mice (10/group) were immunized by the subcutaneous route with the commercial trivalent inactivated flu vaccine (TIV) (2009-2010) alone or adjuvanted with 30 µg of either PapMV sm or PapMV VLPs prepared according to the process described in Example 2. Blood was collected from the mice 14 days after injection and serum was obtained by standard protocols. ELISA directed to the TIV and total IgG or the IgG2a titers were performed using the serum.

The results are shown in FIG. 32 and demonstrate that after a single injection, the PapMV VLPs prepared according to the process described in Example 2 resulted in total IgG and IgG2a titers that are significantly higher than those observed with TIV alone. The titers obtained the PapMV VLPs prepared according to the process described in Example 2 were also superior to those observed in the group that received TIV adjuvanted with PapMV sm.

This result strongly suggests that PapMV VLPs prepared by the process according to the present invention are capable of providing a more potent adjuvant effect than PapMV sm, even though they are structurally similar.

Experiments in which the PapMV VLPs were injected alone (without TIV) also indicated that the IgG2 response to the VLPs was stronger for the VLPs prepared according to the process described in Example 2 than for PapMV sm.

The disclosure of all patents, publications, including published patent applications, and database entries referenced in this specification are expressly incorporated by reference in their entirety to the same extent as if each such individual patent, publication, and database entry were expressly and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

The embodiments of the invention in which an exclusive property or privilege is claimed are defined as follows:

1. An in vitro process for preparing *papaya* mosaic virus (PapMV) virus-like particles (VLPs), comprising the steps of:
   a) combining recombinant PapMV coat protein and ssRNA at a protein:RNA ratio of between about 1:1 and 50:1 by weight, at a pH between about 6.0 and about 9.0, and a temperature between about 2° C. and about 37° C., for a time sufficient to allow assembly of VLPs, wherein the recombinant PapMV coat protein is predominantly in the form of low molecular weight species of less than 20-mers, and wherein the ssRNA is between about 250 nucleotides and about 5000 nucleotides in length and comprises a sequence identical to a reference sequence of about 250 nucleotides of the PapMV 5'-end genome, except wherein said sequence is polymutated in that all AUG codons originally present in the reference sequence have been mutated to UAA stop codons;
   b) treating the VLPs with nuclease to remove any RNA protruding from the particles, and
   c) separating the VLPs from other process components.

2. The process according to claim 1, wherein the recombinant PapMV coat protein is a genetically modified coat protein.

3. The process according to claim 1, wherein the recombinant coat protein is fused to one or more antigenic peptides.

4. The process according to claim 1, wherein the protein:RNA ratio is between about 5:1 and 50:1 by weight.

5. The process according to claim 1, wherein the protein:RNA ratio is between about 10:1 and 50:1 by weight.

6. The process according to claim 1, wherein the pH is between about pH6.5 and pH8.5.

7. The process according to claim 1, wherein the pH is between about pH7.0 and pH8.5.

8. The process according to claim 1, wherein the temperature is between about 5° C. and about 37° C.

9. The process according to claim 1, wherein the temperature is between about 10° C. and about 37° C.

10. The process according to claim 1, wherein the temperature is between about 20° C. and about 37° C.

11. The process according to claim 1, wherein the recombinant PapMV coat protein is produced in *E. coli*.

12. The process according to claim 1, wherein the ssRNA is between about 500 nucleotides and about 3000 nucleotides in length.

13. The process according to claim 1, wherein the ssRNA is between about 1000 and about 3000 nucleotides in length.

14. The process according to claim 1, wherein the reference sequence comprises:
   (a) a sequence identical to nucleotides 17 to 54 of SEQ ID NO: 5;
   (b) a sequence identical to the nucleic acid sequence as set forth in SEQ ID NO: 5; or
   (c) a sequence identical to the nucleic acid sequence as set forth in SEQ ID NO: 6.

15. The process according to claim 1, wherein the protein:RNA ratio is between about 5:1 and 40:1 by weight, the pH is between about 6.5 and about 8.5, and the temperature is between about 22° C. and about 37° C.

16. A *papaya* mosaic virus (PapMV) virus-like particle (VLP) prepared by an in vitro process comprising the steps of:
   a) combining recombinant PapMV coat protein and ssRNA at a protein:RNA ratio of between about 1:1 and 50:1 by weight, at a pH between about 6.0 and about 9.0, and a temperature between about 2° C. and about 37° C., for a time sufficient to allow assembly of VLPs, wherein the recombinant PapMV coat protein is predominantly in the form of low molecular weight species of less than 20-mers, and wherein the ssRNA is between about 250 nucleotides and about 5000 nucleotides in length and comprises a sequence identical to a reference sequence of about 250 nucleotides of the PapMV 5'-end genome, except wherein said sequence is polymutated in that all AUG codons originally present in the reference sequence have been mutated to UAA stop codons;

b) treating the VLPs with nuclease to remove any RNA protruding from the particles, and c) separating the VLPs from other process components, wherein said PapMV VLP delivers said ssRNA to endosomally-located TLR7 to stimulate the innate immune response in a subject.

17. A *papaya* mosaic virus (PapMV) virus-like particle (VLP) comprising recombinant PapMV coat protein and ssRNA, wherein the ssRNA is between about 250 nucleotides and about 5000 nucleotides in length and comprises:

a. a sequence identical to the nucleic acid sequence as set forth in SEQ ID NO:5, or b. a sequence identical to the nucleic acid as set forth in SEQ ID NO: 6, or c. a sequence identical to a fragment of at least about 250 nucleotides from the 5' end of SEQ ID NO: 5 or 6, wherein every thymine (T) residue in said sequence is replaced by a uracil (U) residue, and wherein said PapMV VLP delivers said ssRNA to endosomally-located TLR7 to stimulate the innate immune response in a subject.

18. The PapMV VLP according to claim 17, wherein the ssRNA is between about 500 and about 3000 nucleotides in length or is between about 1000 and about 3000 nucleotides in length.

19. The PapMV VLP according to claim 17, wherein the ssRNA comprises the sequence identical to the nucleic acid sequence as set forth in SEQ ID NO:5.

20. A pharmaceutical composition comprising the PapMV VLP according to claim 17 and a pharmaceutically acceptable carrier or diluent.

21. The PapMV VLP according to claim 17, wherein the recombinant PapMV coat protein comprises one or more antigenic peptides fused at the N-terminus or the C-terminus of the coat protein.

22. The pharmaceutical composition according to claim 20 further comprising one or more antigens.

23. The pharmaceutical composition according to claim 22, wherein the one or more antigens are one or more influenza antigens, one or more cancer-associated antigens, or one or more allergens.

24. A method of enhancing an immune response to an antigen in a subject comprising administering to the subject an adjuvant comprising the VLP according to claim 17.

25. The method according to claim 24, wherein the immune response is a humoral or CTL immune response.

26. The method according to claim 24, wherein the immune response is a mucosal immune response.

27. A method of stimulating the innate immune response in a subject and thereby prevent, or decrease the severity of, a microbial infection in the subject, comprising administering to the subject the VLP according to claim 17.

28. A method of stimulating an immune response in a subject comprising administering to the subject the VLP according to claim 17 in combination with one or more antigens.

29. The method according to claim 28, wherein the one or more antigens are one or more influenza antigens, one or more cancer-associated antigens, or one or more allergens.

30. An in vitro process for preparing the *papaya* mosaic virus (PapMV) virus-like particles (VLPs) according to claim 17 comprising the steps of:

a) combining recombinant PapMV coat protein and ssRNA at a protein:RNA ratio of between about 1:1 and 50:1 by weight, at a pH between about 6.0 and about 9.0, and a temperature between about 2° C. and about 37° C., for a time sufficient to allow assembly of VLPs, wherein the recombinant PapMV coat protein is predominantly in the form of low molecular weight species of less than 20-mers, wherein the ssRNA is between about 250 nucleotides and about 5000 nucleotides in length and comprises:

i. a sequence identical to the nucleic acid sequence as set forth in SEQ ID NO:5, ii. a sequence identical to the nucleic acid sequence as set forth in SEQ ID NO: 6, or iii. a fragment of at least about 250 nucleotides from the 5' end of SEQ ID NO: 5 or 6, wherein every thymine (T) residue in said sequence is replaced by a uracil (U) residue;

b) treating the VLPs with nuclease to remove any RNA protruding from the particles, and c) separating the VLPs from other process components.

31. The process according to claim 30, wherein the recombinant PapMV coat protein is fused to one or more antigenic peptides.

32. The process according to claim 31, wherein the one or more antigenic peptides are fused at the N-terminus or the C-terminus of the coat protein.

* * * * *